US007157085B2

(12) United States Patent
Lowman et al.

(10) Patent No.: US 7,157,085 B2

(45) Date of Patent: Jan. 2, 2007

(54) METHOD FOR TREATING IGE-MEDIATED DISORDERS

(75) Inventors: Henry B. Lowman, El Granada, CA (US); Leonard G. Presta, San Francisco, CA (US); Paula M. Jardieu, San Mateo, CA (US); John Lowe, Daly City, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 10/791,619

(22) Filed: Mar. 2, 2004

(65) Prior Publication Data

US 2004/0259077 A1 Dec. 23, 2004

Related U.S. Application Data

(60) Continuation of application No. 09/716,028, filed on Nov. 17, 2000, now Pat. No. 6,723,833, which is a division of application No. 09/109,207, filed on Jun. 30, 1998, now Pat. No. 6,172,213.

(60) Provisional application No. 60/051,554, filed on Jul. 2, 1997.

(51) Int. Cl.
*A61K 39/395* (2006.01)

(52) U.S. Cl. .............................. 424/133.1; 424/139.1; 424/141.1; 424/145.1; 530/387.3; 530/387.9; 530/388.25

(58) Field of Classification Search ............ 424/133.1, 424/139.1, 145.1; 530/387.3, 388.73
See application file for complete search history.

(56) References Cited

U.S. PATENT DOCUMENTS

| | | | |
|---|---|---|---|
| 4,255,519 | A | 3/1981 | Terada et al. |
| 4,275,149 | A | 6/1981 | Litman et al. |
| 4,816,567 | A | 3/1989 | Cabilly et al. |
| 5,534,617 | A | 7/1996 | Cunningham et al. |
| 5,561,053 | A | 10/1996 | Crowley |
| 5,622,700 | A | 4/1997 | Jardieu et al. |
| 5,705,154 | A | 1/1998 | Dalie et al. |
| 5,750,373 | A | 5/1998 | Garrard et al. |
| 5,821,337 | A | 10/1998 | Carter et al. |
| 5,965,709 | A | 10/1999 | Presta et al. |
| 5,994,511 | A | 11/1999 | Lowman et al. |
| 6,037,453 | A | 3/2000 | Jardieu et al. |
| 6,054,297 | A | 4/2000 | Carter et al. |
| 6,329,509 | B1 | 12/2001 | Jardieu et al. |
| 6,407,213 | B1 | 6/2002 | Carter et al. |

FOREIGN PATENT DOCUMENTS

| | | |
|---|---|---|
| EP | 239 400 B1 | 8/1994 |
| WO | WO 92/17207 | 10/1992 |
| WO | WO 93/04173 | 3/1993 |
| WO | WO 9311161 A1 * | 6/1993 |
| WO | WO 93/16185 | 8/1993 |
| WO | WO 94/20533 | 9/1994 |
| WO | WO 95/24481 | 9/1995 |
| WO | WO 97/06822 | 2/1997 |

OTHER PUBLICATIONS

Chang, T W. "The pharmacological basis of anti-IgE therapy" (2000) Nature Biotechnology, 18:157-162.*

Tortora et al., "Microbiology, an Introduction" 5th edition, (1995) Benjamin-Cummings Publishing Company, Inc., pp. 466-469.*

Kipriyanov et al., "Generation of recombinant antibodies" (1999) Molecular Biotechnology, 12:173-201.*

Leung et al., N Engl J Med, 2003, 348:986-993.*

Webster's New World Dictionary, third college edition, 1988, Simon & Schuster, Inc., p. 1067.*

Wadee et al., J Allergy Clin Immunol, 1987, 80:695-698.*

Reimers et al., Clin Exp Allergy, 2000, 30:276-82.*

Alberts et al., "The Immune System" *Molecular Biology of The Cell*, 3d edition, New York and London:Garland Publishing, Inc., Chapter 23, pp. G-15 and 1232, 1994.

Amit et al., "Three-Dimensional Structure of an Antigen-antibody Complex at 2.8 A Resolution" *Science* 233:747-753 (Aug. 1986).

Barbas III et al., "In Vitro Evolution of a Neutralizing Human Antibody to Human Immunodeficiency Virus Type 1 to Enhance Affinity and Broaden Strain Cross-Reactivity." *Proc. Natl. Acad. Sci. USA* 91(9):3809-3813 (Apr. 26, 1994).

Brennan et al., "Preparation of bispecific antibodies by chemical recombination of monoclonal immunoglobulin $G_1$ fragments" *Science* 229:81-83 (Jul. 1985).

Cacia et al., "Isomerization of an aspartic acid residue in the complementarity-determining regions of a recombinant antibody to human IgE: identification and effect on binding affinity" *Biochemistry* 35(6):1897-1903 (Feb. 13, 1996).

(Continued)

*Primary Examiner*—G. R. Ewoldt
*Assistant Examiner*—Michael Szperka
(74) *Attorney, Agent, or Firm*—Craig G. Svoboda

(57) ABSTRACT

The present invention relates to a method for adjusting the affinity of a polypeptide to a target molecule by a combination of steps, including: (1) the identification of aspartyl residues which are prone to isomerization; (2) the substitution of alternative residues and screening the resulting mutants for affinity against the target molecule. In a preferred embodiment, the method of subtituting residues is affinity maturation with phage display (AMPD). In a further preferred embodiment the polypeptide is an antibody and the target molecule is an antigen. In a further preferred embodiment, the antibody is anti-IgE and the target molecule is IgE. In another embodiment, the invention relates to an anti-IgE antibody having improved affinity to IgE.

18 Claims, 19 Drawing Sheets

OTHER PUBLICATIONS

Carter et al., "High Level *Escherichia coli* Expression and Production of a Bivalent Humanized Antibody Fragment." *Bio/Technology*. 10(2):163-167 (Feb. 1992).
Carter et al., "Humanization of an Anti-p185$^{HER2}$ Antibody For Human Cancer Therapy" *Proc. Natl. Acad. Sci. USA* 89:4285-4289 (May 1992).
Champe et al., "Monoclonal antibodies that block the activity of leukocyte function-associated antigen 1 recognize three discrete epitopes in the inserted domain of CD11a" *Journal of Biological Chemistry* 270:1388-1394 (1995).
Chothia and Lesk, "Canonical Structures for the Hypervariable Regions of Immunoglobins" *J. Mol. Biol.* 196:901-917 (1987).
Chothia et al., "Domain Association in Immunoglobulin Molecules. The Packing of Variable Domains" *Journal of Molecular Biology* 186:651-663 (1985).
Chothia, C. et al., "Conformations of immunoglobin hypervariable regions" *Nature* 342(6252):877-883 (1989).
Clackson et al., "Making Antibody Fragments Using Phage Display Libraries" *Nature* 352:624-628 (1991).
Co et al., "Humanized antibodies for antiviral therapy" *Proc. Natl. Acad. Sci. USA* 88:2869-2873 (Apr. 1991).
Cunningham et al., "Production of an Atrial Natriuretic Peptide Variant that is Specific for Type A Receptor" *EMBO Journal* 13(11):2508-2515 (1994).
Geiger and Clarke, "Deamidation, isomerization, and racemization at asparaginyl and aspartyl residues in peptides. Succinimide-linked reactions that contribute to protein degradation" *Journal of Biological Chemistry* 262(2):785-794 (Jan. 15, 1987).
Goding, J.W., "Conjugation of antibodies with fluorochromes: modifications to the standard methods" *Journal of Immunological Methods* 13(3-4):215-226 (1976).
Hakimi et al., "The α subunit of the human IgE receptor (FcERI) is sufficient for high affinity IgE binding" *Journal of Biological Chemistry* 265(336):22079-22081 (1990).
Hawkins et al., "Selection of Phage antibodies by Binding Affinity Mimicking Affinity Maturation" *J. Mol. Biol*, 226:889-896 (1992).
Herbert et al. *Directory of Immunology*, 3rd edition, Blackwell Scientific Publications pp. 77 (1985).
Holliger et al., ""Diabodies": Small Bivalent and Bispecific Antibody Fragments." *Proc. Natl. Acad. Sci. USA* 90:6444-6448 (Jul. 1993).
Jones et al., "Replacing the Complementarity-Determining Regions in a Human Antibody with Those From a Mouse." *Nature*, 321:522-525 (May 29, 1986).
Kabat et al. *Sequences of Proteins of Immunological Interest*, Bethesda, MD:National Institute of Health (1987).
Kabat *Sequences of Proteins of Immunological Interest* (Fourth Ed:), 4th edition pp. 41-42, 167-168 (1987).
Kabat *Sequences of Proteins of Immunological Interest* (pp. 662-663, 671-672, 680-681, 697, 701-702, 710, 719-720, 2275-2276), 5th edition'1 (1991).
Kettleborough et al., "Humanization of a Mouse Monoclonal Antibody by CDR-grafting: the Importance of Framework Residues on Loop Conformation" *Protein Engineering* 4(7):773-783 (1991).
Kohler and Milstein., "Continuous Cultures of Fused Cells Secreting Antibody of Predefined Specificity." *Nature*, 256:495-497 (Aug. 7, 1975).
Konig et al., "Chemical and Biological Properties of Porcine Secretin and Secretin Analogues Modified in Positions 3 and 4" *Gastroenterology* 72:797-800 (1977).
Kunkel et al., "Efficient site-directed mutagenesis using uracil-containing DNA" *Methods in Enzymology* 204:125-139 (1991).
Lowe et al., "Allergen-induced Histamine Release in Rat Mast Cells Transfected with the α Subunits of FcεRI" *J. Immunological Methods* 184:113-122 (1995).
Lowenson and Clarke, "Identification of isoaspartyl-containing sequences in peptides and proteins that are unusually poor substrates for the class II protein carboxyl methyltransferase" *Journal of Biological Chemistry* 265(6):3106-3110 (Feb. 25, 1990).
Lowman and Wells, "Affinity Maturation of Human Growth Hormone by Monovalent Phage Display" *J. Mol. Biol*. 234:564-578 (1993).
Lowman et al., "Selecting High-Affinity Binding Proteins by Monovalent Phage Display" *Biochemistry* 30(45):10832-10838 (1991).
Marks et al., "By-Passing Immunization: Building High Affinity Human Antibodies by Chain Shuffling" *Bio/Technology* 10:779-783 (1992).
Marks et al., "By-Passing Immunization: Human Antibodies From V-gene Libraries Displayed On Phage" *J. Mol. Biol*.222:581-597 (1991).
McCafferty et al., "Phage antibodies: filamentous phage displaying antibody variable domains" *Nature* 348:552-554 (1990).
Metzger and Kinet, "How Antibodies Work: Focus on Fc Receptors" *FASEB J* 2(1):3-11 (Jan. 1988).
Morimoto et al., "Single-step purification of F(ab' )$_2$ fragments of mouse monoclonal antibodies (immunoglobulins G1) by hydrophobic interaction high performance liquid chromatography using TSKgel Phenyl-5PW" *Journal of Biochemical and Biophysical Methods* 24:107-117 (1992).
Morrison et al., "Chimeric Human Antibody Molecules: Mouse Antigen-Binding Domains with Human Constant Region Domains" *Proc. Natl. Acad. Sci. USA* 81:6851-6855 (Nov. 1984).
Novotny et al., "Structural invariants of antigen binding: comparison of Immunoglobulin $V_L$-$V_H$ and $V_L$-$V_L$ domain dimers" *Proc. Natl. Acad. Sci. USA* 82(14):4592-4596 (Jul. 1985).
Oliyai and Borchardt, "Chemical pathways of peptide degradation. IV. Pathways, kinetics, and mechanism of degradation of an aspartyl residue in a model hexapeptide" *Pharmaceutical Research* 10(1):95-102 (Jan. 1993).
Pluckthun., "Antibodies From *Escherichia coli*." *The Pharmacology of Monoclonal Antibodies: Handbook of Experimental Pharmacology*., Rosenberg and Moore, eds., Berlin:Springer-Verlag, Chapter 11, vol. 113:269-315 (1994).
Presta et al., "Humanization of an Antibody Directed Against IgE" *J. Immunol*. 151(5):2623-2632 (Sep. 1, 1993).
Presta, L., "Antibody Engineering" *Curr. Op. Struct. Biol*. 2:593-596 (1992).
Riechmann et al., "Reshaping Human Antibodies for Therapy" *Nature* 332:323-327 (Mar. 24, 1988).
Routledge et al., "A Humanized Monovalent CD3 Antibody which Can Activate Homologous Complement" *European Journal of Immunology* 21:2717-2725 (1991).
Shearman et al., "Construction, Expression and Characterization of Humanized Antibodies Directed Against the Human α/β T Cell Receptor" *J. Immunol*. 147(12):4366-4373 (Dec. 15, 1991).
Shields et al., "Inhibition of Allergic Reactions with Antibodies to IgE" *International Archives of Allergy and Immunology* 107(1-3):308-312 (May 1995).
Sims et al., "A Humanized CD18 Antibody Can Block Function Without Cell Destruction" *The Journal of Immunological* 151(4):2296-2308 (Aug. 1993).
Suresh et al., "Bispecific Monoclonal Antibodies from Hybrid Hybridomas" *Methods in Enzymology* 121:210-228 (1986).
Tempest et al., "Reshaping a Human Monclonal Antibody to Inhibit Human Respiratory Syncytial Virus Infection In Vivo" *Bio/Technology* 9:266-271 (Mar. 1991).
Tutt et al., "Trispecific F(ab')3 Derivatives That Use Cooperative Signaling Vis the TCR/CD3 Complex and CD2 to Activate and Redirect Resting Cytotoxic T Cells" *J. Immunol*. 147(1):60-69 (1991).
Verhoeyen et al., "Reshaping Human Antibodies: Grafting an Antilysozyme Activity" *Science* 239:1534-1536 (Mar. 25, 1988).
Waterhouse et al., "Combinatorial infection and in vivo recombination: a strategy for making large phage antibody repertoires" *Nucleic Acids Research* 21:2265-2266 (1993).
Yang et al., "CDR walking mutagenesis for the affinity maturation of a potent human anti-HIV-1 antibody into the picomolar range" *Journal of Molecular Biology* 254(3):392-403 (Dec. 1, 1995).

* cited by examiner

VH DOMAIN

```
                10          20            30             40
MaE11    DVQLQESGPG  LVKPSQSLSL  ACSVTGYSITS  [GYSWN]WIRQF
         *   *   *    * **   *   * * *              *
F(ab)-2  EVQLVESGGG  LVQPGGSLRL  SCAVSGYSITS  [GYSWN]WIRQA
                                    * ****     * ***   *
humIII   EVQLVESGGG  LVQPGGSLRL  SCAASGFTF-S  [DYAMS]WVRQA

                49            60         70          80
MaE11    PGNKLEWMG   [SITYDGSSNYN PSLKN]RISVT  RDTSQNQFFL
           **   **          *   *  * * * * ****   * * * **
F(ab)-2  PGKGLEWVA   [SITYDGSTNYA DSVKG]RFTIS  RDDSKNTFYL
                      * ***** *
humIII   PGKGLEWVA   [VISNGSDTYYA DSVKG]RFTIS  RDDSKNTLYL

         82abc     90        100abcd    103        113
MaE11    KLNSATAEDTATY  YCAR[GSHYFGHWHFAV]  WGAGTTVT  VSS
         **  **     *               *  *
F(ab)-2  QMNSLRAEDTAVY  YCAR[GSHYFGHWHFAV]  WGQGTLVT  VSS
                              * ** ******
humIII   QMNSLRAEDTAVY  YCAR[DSRFF-----DV]  WGQGTLVT  VSS
```

VL DOMAIN

```
                10          20            30 32abcd        40
MaE11    DIQLTQSPAS  LAVSLGQRAT  ISC[KASQSVD YDGDSYMN]WYQQKP
                  *   ** * * *   *   *
F(ab)-2  DIQLTQSPSS  LSASVGDRVT  ITC[RASQSVD YDGDSYMN]WYQQKP
                                             ****  *
humk1    DIQMTQSPSS  LSASVGDRVT  ITC[RASQSVD IS--SYLN]WYQQKP

                49             60        70          80
MaE11    GQPPILLIY   [AASYLGS]EIPA RFSGSGSGTD  FTLNIHPVEE
           ** *           *  ** *                * *****
F(ab)-2  GKAPKLLIY   [AASYLES]GVPS RFSGSGSGTD  FTLTISSLQP
                         *
humkI    GKAPKLLIY   [AASSLES]GVPS RFSGSGSGTD  FTLTISSLQP

                88          97          107
MaE11    EDAATFYC    [QQSHEDPYT]  FGAGTKLEIK
           *   *                   *    *
F(ab)-2  EDFATYYC    [QQSHEDPYT]  FGQGTKVEIK
                        ****
humk1    EDFATYYC    [QQYNSLPYT]  FGQGTKVEIK
```

*FIG._1*

LIGHT CHAIN

```
                10          20          30          40
e27     DIQLTQSPSS  LSASVGDRVT  ITCRASKPVD  GEGDSYLNWY
e26     DIQLTQSPSS  LSASVGDRVT  ITCRASKPVD  GEGDSYLNWY
e426    DIQLTQSPSS  LSASVGDRVT  ITCRASQSVD  YEGDSYLNWY
e25     DIQLTQSPSS  LSASVGDRVT  ITCRASQSVD  YDGDSYMNWY
                                        CDR-L1

                50          60          70          80
e27     QQKPGKAPKL  LIYAASYLES  GVPSRFSGSG  SGTDFTLTIS
e26     QQKPGKAPKL  LIYAASYLES  GVPSRFSGSG  SGTDFTLTIS
e426    QQKPGKAPKL  LIYAASYLES  GVPSRFSGSG  SGTDFTLTIS
e25     QQKPGKAPKL  LIYAASYLES  GVPSRFSGSG  SGTDFTLTIS
                          CDR-L2

                90          100         110
e27     SLQPEDFATY  YCQQSHEDPY  TFGQGTKVEI  KRTV
e26     SLQPEDFATY  YCQQSHEDPY  TFGQGTKVEI  KRTV
e426    SLQPEDFATY  YCQQSHEDPY  TFGQGTKVEI  KRTV
e25     SLQPEDFATY  YCQQSHEDPY  TFGQGTKVEI  KRTV
                      CDR-L3
```

HEAVY CHAIN

```
                10          20          30          40
e27     EVQLVESGGG  LVQPGGSLRL  SCAVSGYSIT  SGYSWNWIRQ
e26     EVQLVESGGG  LVQPGGSLRL  SCAVSGYSIT  SGYSWNWIRQ
e426    EVQLVESGGG  LVQPGGSLRL  SCAVSGYSIT  SGYSWNWIRQ
e25     EVQLVESGGG  LVQPGGSLRL  SCAVSGYSIT  SGYSWNWIRQ
                                        CDR-H1

                50          60          70          80
e27     APGKGLEWVA  SIKYSGETKY  NPSVKGRITI  SRDDSKNTFY
e26     APGKGLEWVA  SITYDGSTNY  NPSVKGRITI  SRDDSKNTFY
e426    APGKGLEWVA  SITYDGSTNY  NPSVKGRITI  SRDDSKNTFY
e25     APGKGLEWVA  SITYDGSTNY  NPSVKGRITI  SRDDSKNTFY
                          CDR-H2

                90          100         110
e27     LQMNSLRAED  TAVYYCARGS  HYFGHWHFAV  WGQG
e26     LQMNSLRAED  TAVYYCARGS  HYFGHWHFAV  WGQG
e426    LQMNSLRAED  TAVYYCARGS  HYFGHWHFAV  WGQG
e25     LQMNSLRAED  TAVYYCARGS  HYFGHWHFAV  WGQG
                                CDR-H3
```

FIG._2

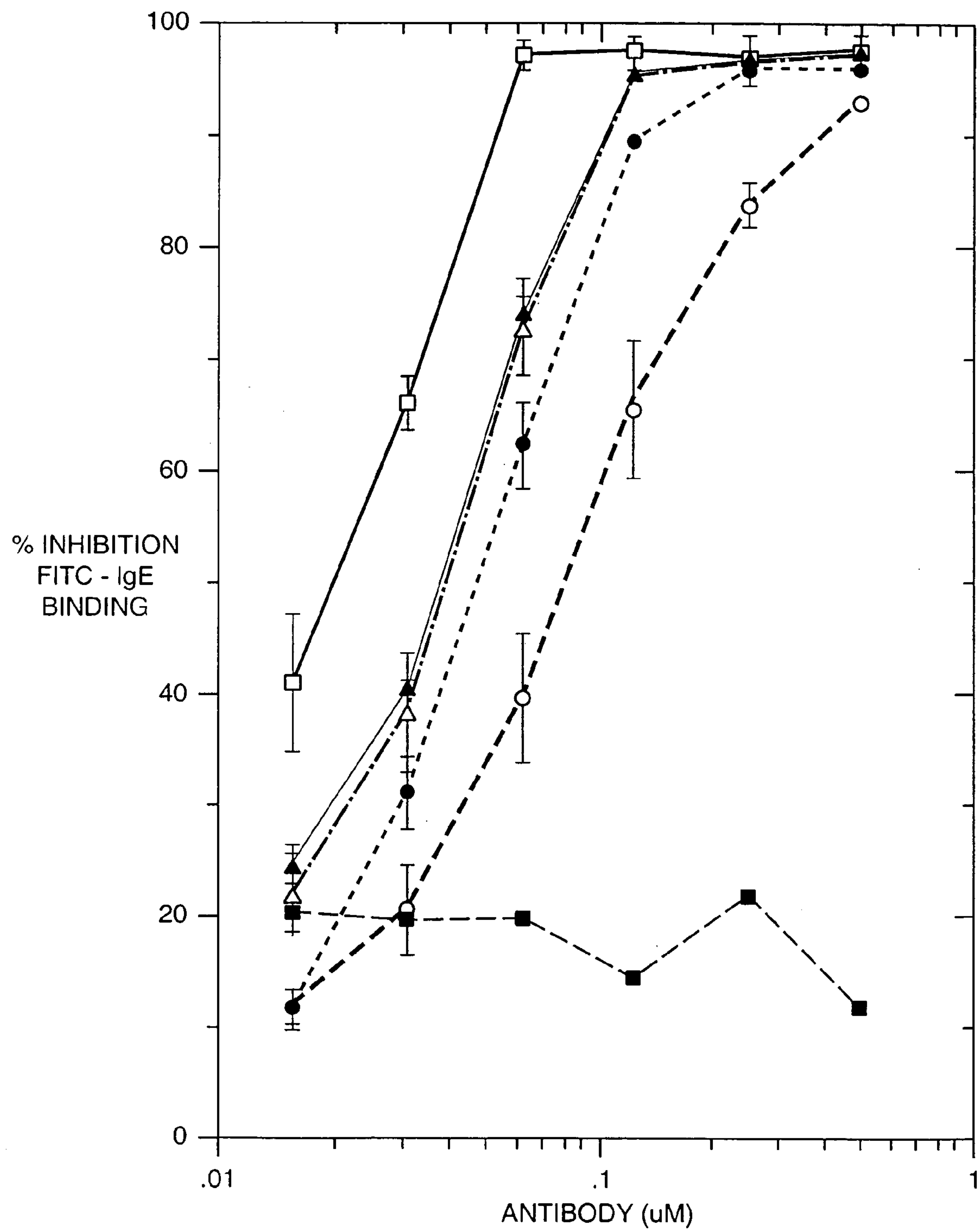
FIG._3

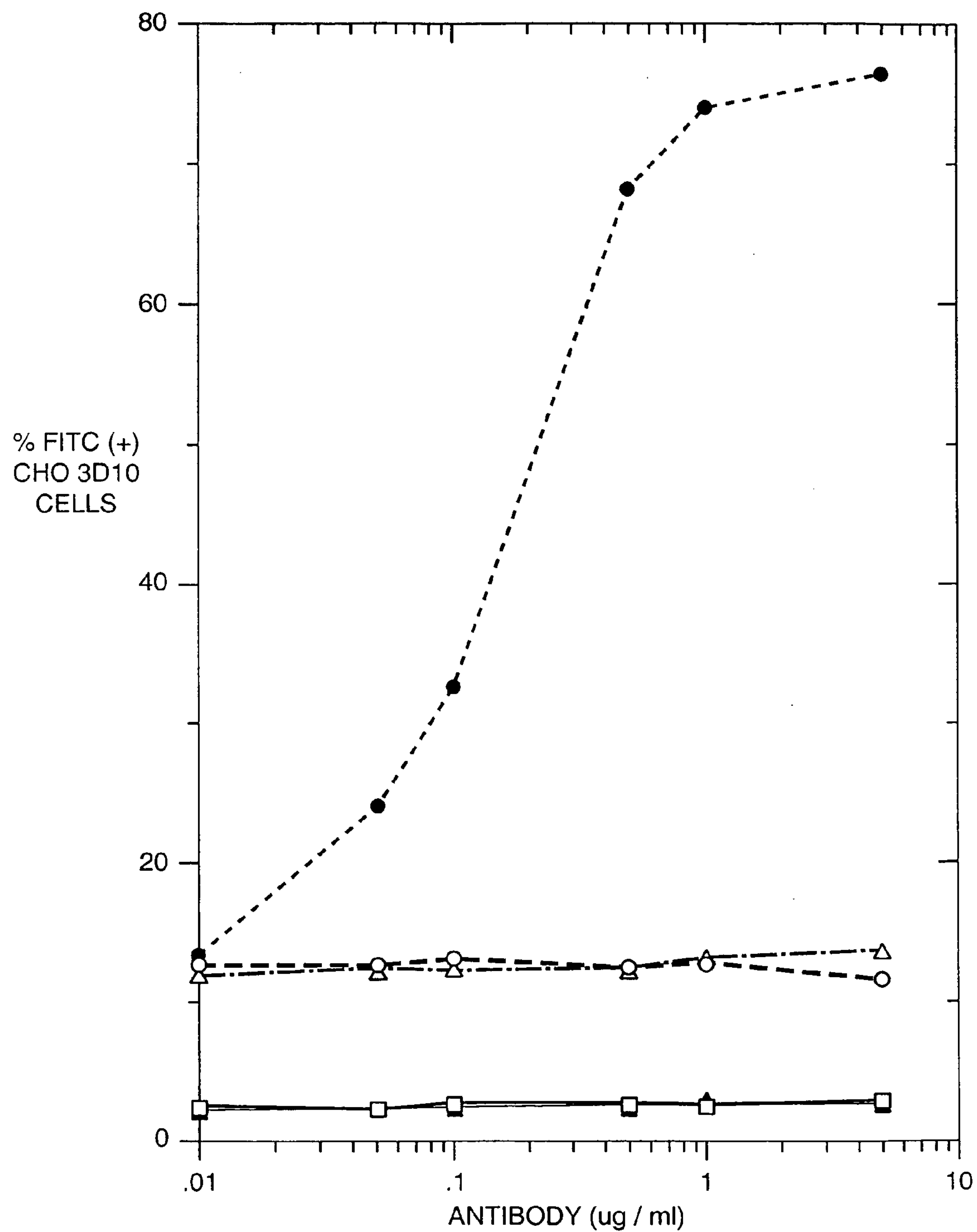
FIG._4

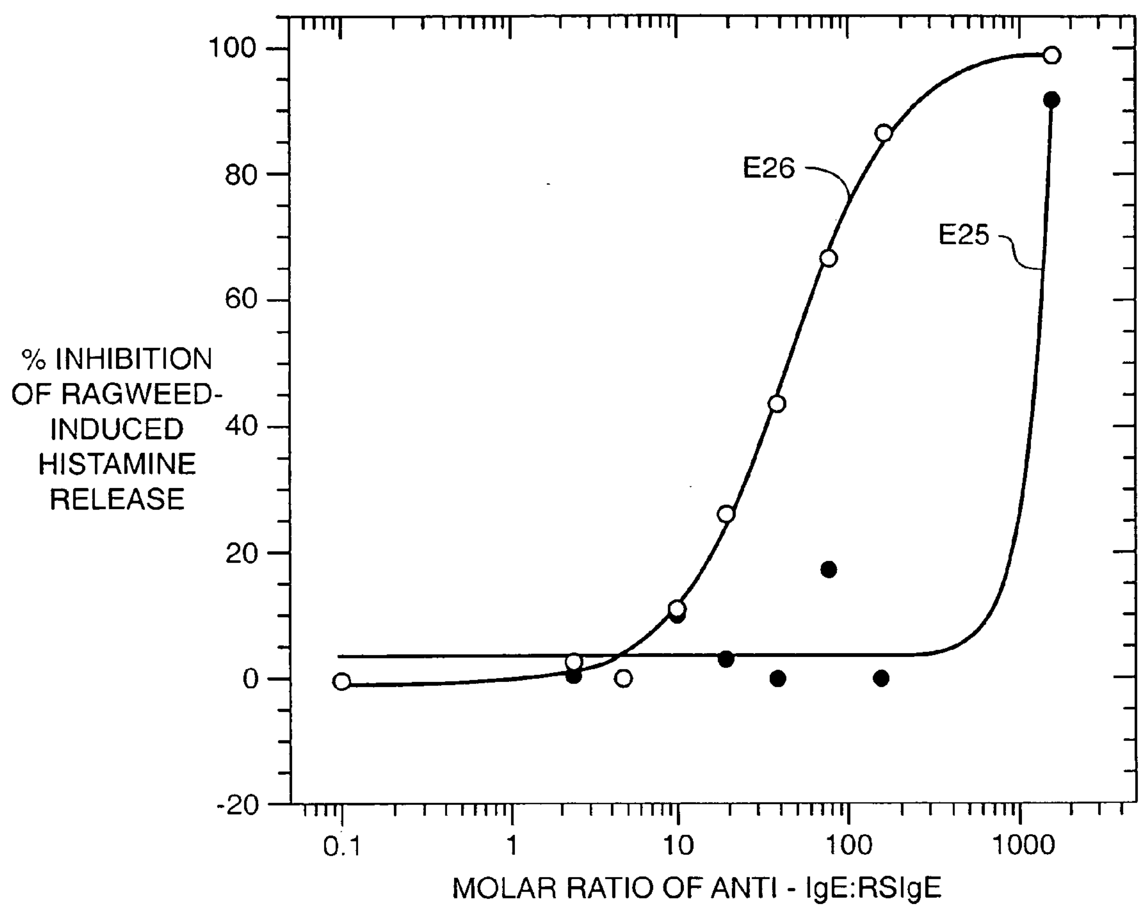
y = ((m1 - m4) / (1 + (m0 / m3)^m2))...
| | VALUE | ERROR |
|---|---|---|
| m1 | 3.7289 | 3.2575 |
| m2 | 3.2312 | 2044.6 |
| m3 | 3421.3 | 7.095e+07 |
| m4 | 1226.5 | 7.4139e+07 |
| Chisq | 293.26 | NA |
| R | 0.97929 | NA |
y = ((m1 - m4) / (1 + (m0 / m3)^m2))...
| | VALUE | ERROR |
|---|---|---|
| m1 | -0.78645 | 1.7681 |
| m2 | 1.3544 | 0.11267 |
| m3 | 44.486 | 3.1931 |
| m4 | 100.07 | 2.6239 |
| Chisq | 31.442 | NA |
| R | 0.99867 | NA |
*FIG._5*

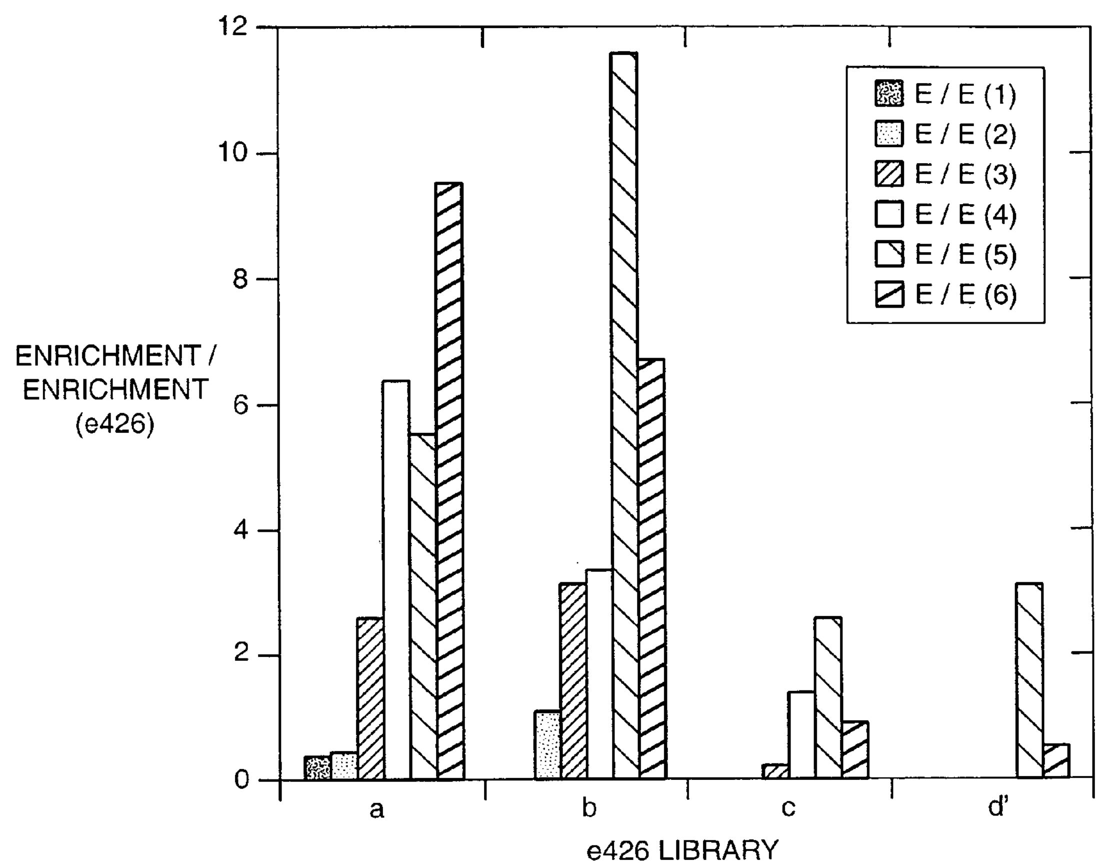
FIG._6

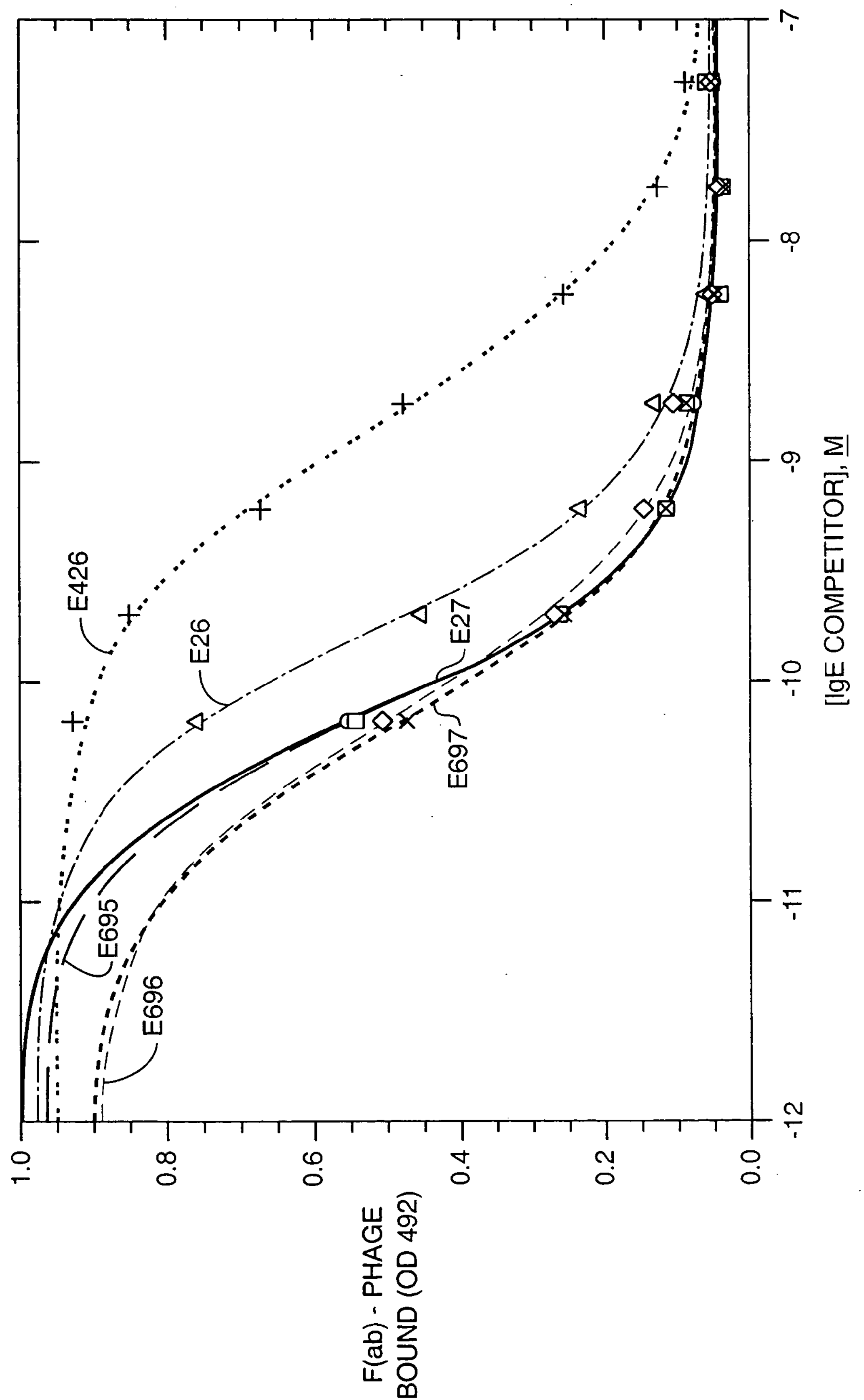
FIG._7

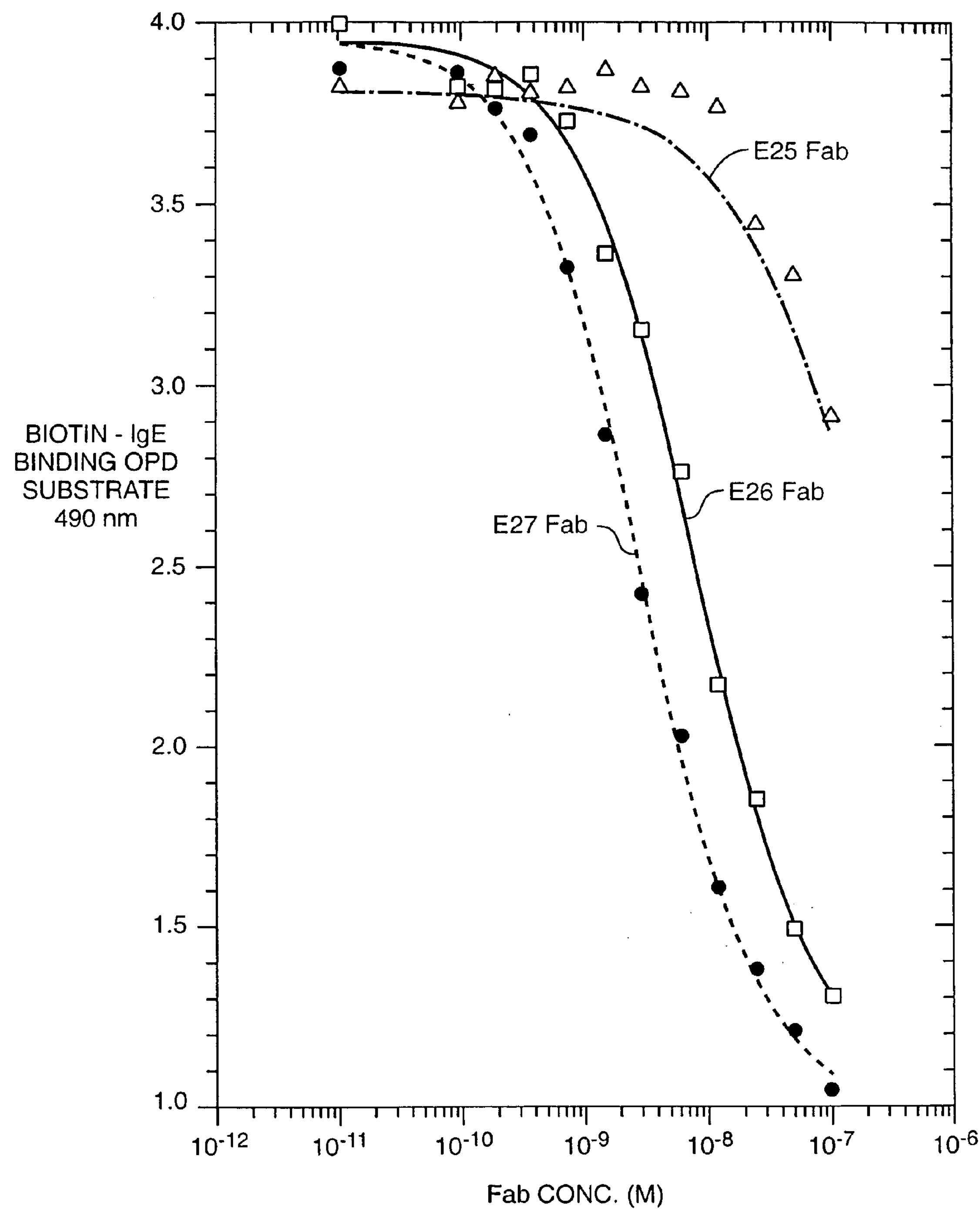
FIG._8

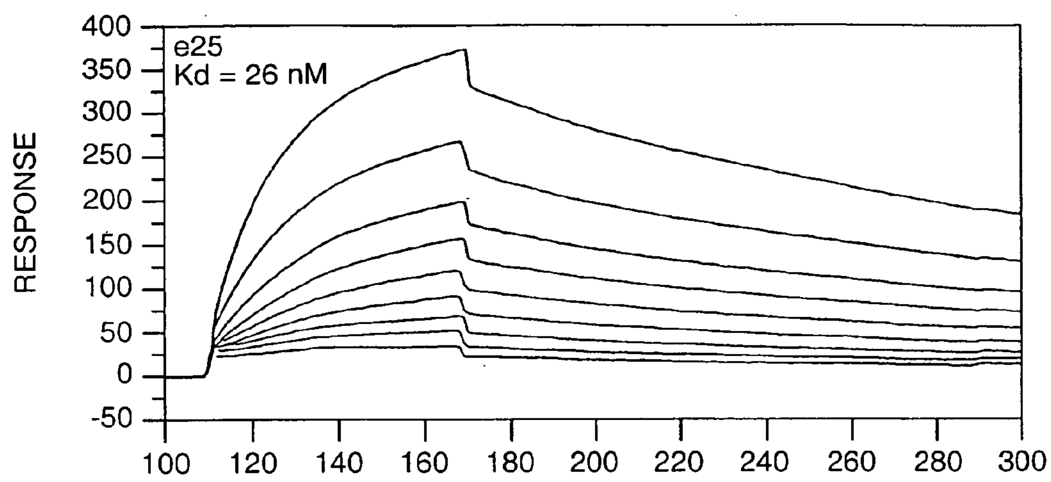
FIG._9A
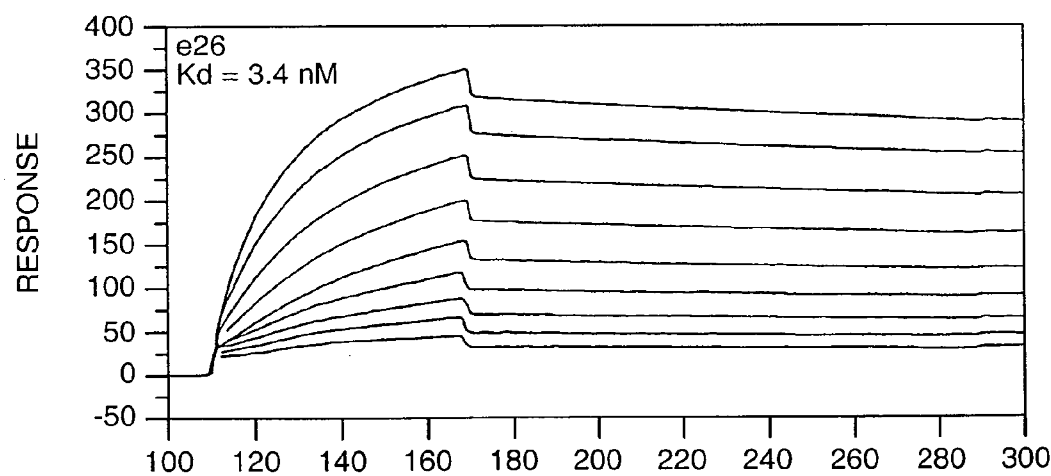
FIG._9B
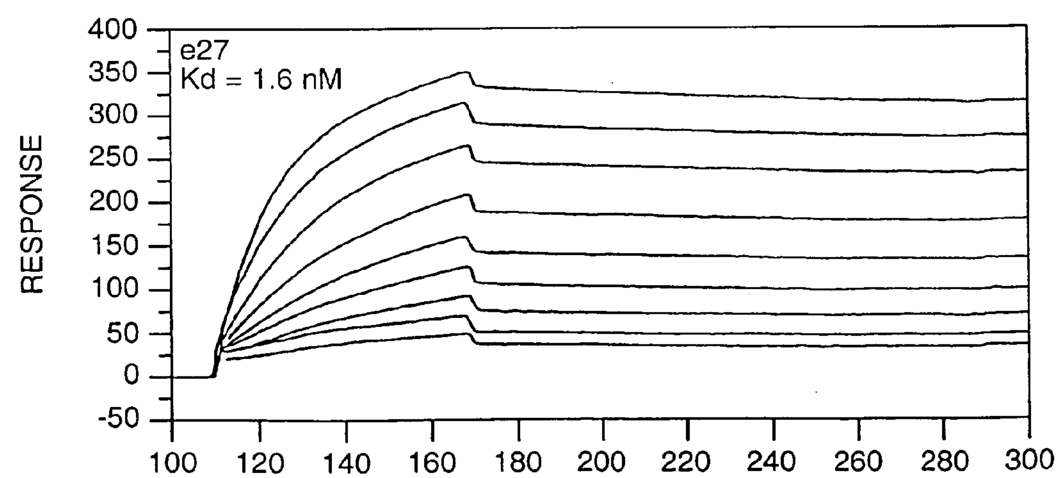
FIG._9C

```
  1 GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
    CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

101 GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
    CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

201 GGGCGCTGTA CGAGGTAAAG CCCGATGCCA GCATTCCTGA CGACGATACG GAGCTGCTGC GCGATTACGT AAAGAAGTTA TTGAAGCATC CTCGTCAGTA
    CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GCTGTCATAA AGTTGTCACG GCCGAGACTT ATAGTCGCTT TGTTTTTATT TTTTAATGTA TTTGTAACTA GAATTCGAGC
    TTTTCAATTA GAAAAGTTGT CGACAGTATT TCAACAGTGC CGGCTCTGAA TATCAGCGAA ACAAAAATAA AAAATTACAT AAACATTGAT CTTAAGCTCG

401 TCGGTACCCG GGGATCCTCT CGAGGTTGAG GTGATTTTAT GAAAAAGAAT ATCGCATTTC TTCTTGCATC TATGTTCGTT TTTTCTATTG CTACAAACGC
    AGCCATGGGC CCCTAGGAGA GCTCCAACTC CACTAAAATA CTTTTTCTTA TAGCGTAAAG AAGAACGTAG ATACAAGCAA AAAAGATAAC GATGTTTGCG

501 GTACGCTGAT ATCCAGCTGA CCCAGTCCCC GAGCTCCCTG TCCGCCTCTG TGGGCGATAG GGTCACCATC ACCTGCCGTG CCAGTCAGAG CGTCGATTAC
    CATGCGACTA TAGGTCGACT GGGTCAGGGG CTCGAGGGAC AGGCGGAGAC ACCCGCTATC CCAGTGGTAG TGGACGGCAC GGTCAGTCTC GCAGCTAATG
  1     AlaAsp IleGlnLeuT hrGlnSerPr oSerSerLeu SerAlaSerV alGlyAspAr gValThrIle ThrCysArgA laSerGlnSe rValAspTyr
        Begin light chain

601 GAAGGTGATA GCTACCTGAA CTGGTATCAA CAGAAACCAG GAAAAGCTCC GAAACTACTG ATTTACGCGG CCTCGTACCT GGAGTCTGGA GTCCCTTCTC
    CTTCCACTAT CGATGGACTT GACCATAGTT GTCTTTGGTC CTTTTCGAGG CTTTGATGAC TAAATGCGCC GGAGCATGGA CCTCAGACCT CAGGGAAGAG
 33 GluGlyAspS erTyrLeuAs nTrpTyrGln GlnLysProG lyLysAlaPr oLysLeuLeu IleTyrAlaA laSerTyrLe uGluSerGly ValProSerArg

701 GCTTCTCTGG ATCCGGTTCT GGGACGGATT TCACTCTGAC CATCAGCAGT CTGCAGCCAG AAGACTTCGC AACTTATTAC TGTCAGCAAA GTCACGAGGA
    CGAAGAGACC TAGGCCAAGA CCCTGCCTAA AGTGAGACTG GTAGTCGTCA GACGTCGGTC TTCTGAAGCG TTGAATAATG ACAGTCGTTT CAGTGCTCCT
 67   PheSerGl ySerGlySer GlyThrAspP heThrLeuTh rIleSerSer LeuGlnProG luAspPheAl aThrTyrTyr CysGlnGlnS erHisGluAsp

801 TCCGTACACA TTTGGACAGG GTACCAAGGT GGAGATCAAA CGAACTGTGG CTGCACCATC TGTCTTCATC TTCCCGCCAT CTGATGAGCA GTTGAAATCT
    AGGCATGTGT AAACCTGTCC CATGGTTCCA CCTCTAGTTT GCTTGACACC GACGTGGTAG ACAGAAGTAG AAGGGCGGTA GACTACTCGT CAACTTTAGA
100  ProTyrThr PheGlyGlnG lyThrLysVa lGluIleLys ArgThrValA laAlaProSe rValPheIle PheProProS erAspGluGl nLeuLysSer

901 GGAACTGCTT CTGTTGTGTG CCTGCTGAAT AACTTCTATC CCAGAGAGGC CAAAGTACAG TGGAAGGTGG ATAACGCCCT CCAATCGGGT AACTCCCAGG
    CCTTGACGAA GACAACACAC GGACGACTTA TTGAAGATAG GGTCTCTCCG GTTTCATGTC ACCTTCCACC TATTGCGGGA GGTTAGCCCA TTGAGGGTCC
133 GlyThrAlaS erValValCy sLeuLeuAsn AsnPheTyrP roArgGluAl aLysValGln TrpLysValA spAsnAlaLe uGlnSerGly AsnSerGlnGlu
```

FIG._10A

```
1001 AGAGTGTCAC AGAGCAGGAC AGCAAGGACA GCACCTACAG CCTCAGCAGC ACCCTGACGC TGAGCAAAGC AGACTACGAG AAACACAAAG TCTACGCCTG
     TCTCACAGTG TCTCGTCCTG TCGTTCCTGT CGTGGATGTC GGAGTCGTCG TGGGACTGCG ACTCGTTTCG TCTGATGCTC TTTGTGTTTC AGATGCGGAC
 167  SerValTh rGluGlnAsp SerLysAspS erThrTyrSe rLeuSerSer ThrLeuThrL euSerLysAl aAspTyrGlu LysHisLysV alTyrAlaCys

1101 CGAAGTCACC CATCAGGGCC TGAGCTCGCC CGTCACAAAG AGCTTCAACA GGGGAGAGTG TTAAGCTGAT CCTCTACGCC GGACGCATCG TGGCCCTAGT
     GCTTCAGTGG GTAGTCCCGG ACTCGAGCGG GCAGTGTTTC TCGAAGTTGT CCCCTCTCAC AATTCGACTA GGAGATGCGG CCTGCGTAGC ACCGGGATCA
 200  GluValThr HisGlnGlyL euSerSerPr oValThrLys SerPheAsnA rgGlyGluCy sOC*
                                                                 end light chain

1201 ACGCAAGTTC ACGTAAAAAG GGTATCTAGA GGTTGAGGTG ATTTTATGAA AAAGAATATC GCATTTCTTC TTGCATCTAT GTTCGTTTTT TCTATTGCTA
     TGCGTTCAAG TGCATTTTTC CCATAGATCT CCAACTCCAC TAAAATACTT TTTCTTATAG CGTAAAGAAG AACGTAGATA CAAGCAAAAA AGATAACGAT

1301 CAAACGCGTA CGCTGAGGTT CAGCTGGTGG AGTCTGGCGG TGGCCTGGTG CAGCCAGGGG GCTCACTCCG TTTGTCCTGT GCAGTTTCTG GCTACTCCAT
     GTTTGCGCAT GCGACTCCAA GTCGACCACC TCAGACCGCC ACCGGACCAC GTCGGTCCCC CGAGTGAGGC AAACAGGACA CGTCAAAGAC CGATGAGGTA
   1                  GluVal GlnLeuValG luSerGlyGl yGlyLeuVal GlnProGlyG lySerLeuAr gLeuSerCys AlaValSerG lyTyrSerIle
                      Begin heavy chain

1401 CACCTCCGGA TACAGCTGGA ACTGGATCCG TCAGGCCCCG GGTAAGGGCC TGGAATGGGT TGCATCGATT ACGTATGACG GATCGACTAA CTATAACCCT
     GTGGAGGCCT ATGTCGACCT TGACCTAGGC AGTCCGGGGC CCATTCCCGG ACCTTACCCA ACGTAGCTAA TGCATACTGC CTAGCTGATT GATATTGGGA
  30  ThrSerGly TyrSerTrpA snTrpIleAr gGlnAlaPro GlyLysGlyL euGluTrpVa lAlaSerIle ThrTyrAspG lySerThrAs nTyrAsnPro

1501 AGCGTCAAGG GCCGTATCAC TATAAGTCGC GACGATTCCA AAAACACATT CTACCTGCAG ATGAACAGCC TGCGTGCTGA GGACACTGCC GTCTATTATT
     TCGCAGTTCC CGGCATAGTG ATATTCAGCG CTGCTAAGGT TTTTGTGTAA GATGGACGTC TACTTGTCGG ACGCACGACT CCTGTGACGG CAGATAATAA
  63 SerValLysG lyArgIleTh rIleSerArg AspAspSerL ysAsnThrPh eTyrLeuGln MetAsnSerL euArgAlaGl uAspThrAla ValTyrTyrCys

1601 GTGCTCGAGG CAGCCACTAT TTCGGTCACT GGCACTTCGC CGTGTGGGGT CAAGGAACCC TGGTCACCGT CTCCTCGGCC TCCACCAAGG GCCCATCGGT
     CACGAGCTCC GTCGGTGATA AAGCCAGTGA CCGTGAAGCG GCACACCCCA GTTCCTTGGG ACCAGTGGCA GAGGAGCCGG AGGTGGTTCC CGGGTAGCCA
  97  AlaArgGl ySerHisTyr PheGlyHisT rpHisPheAl aValTrpGly GlnGlyThrL euValThrVa lSerSerAla SerThrLysG lyProSerVal

1701 CTTCCCCCTA GCACCCTCCT CCAAGAGCAC CTCTGGGGGC ACAGCGGCCC TGGGCTGCCT GGTCAAGGAC TACTTCCCCG AACCGGTGAC GGTGTCGTGG
     GAAGGGGGAT CGTGGGAGGA GGTTCTCGTG GAGACCCCCG TGTCGCCGGG ACCCGACGGA CCAGTTCCTG ATGAAGGGGC TTGGCCACTG CCACAGCACC
 130  PheProLeu AlaProSerS erLysSerTh rSerGlyGly ThrAlaAlaL euGlyCysLe uValLysAsp TyrPheProG luProValTh rValSerTrp

1801 AACTCAGGCG CCCTGACCAG CGGCGTGCAC ACCTTCCCGG CTGTCCTACA GTCCTCAGGA CTCTACTCCC TCAGCAGCGT GGTGACCGTG CCCTCCAGCA
     TTGAGTCCGC GGGACTGGTC GCCGCACGTG TGGAAGGGCC GACAGGATGT CAGGAGTCCT GAGATGAGGG AGTCGTCGCA CCACTGGCAC GGGAGGTCGT
 163 AsnSerGlyA laLeuThrSe rGlyValHis ThrPheProA laValLeuGl nSerSerGly LeuTyrSerL euSerSerVa lValThrVal ProSerSerSer
```

FIG._10B

```
1901 GCTTGGGCAC CCAGACCTAC ATCTGCAACG TGAATCACAA GCCCAGCAAC ACCAAGGTGG ACAAGAAAGT TGAGCCCAAA TCTTGTGACA AAACTCACAC
     CGAACCCGTG GGTCTGGATG TAGACGTTGC ACTTAGTGTT CGGGTCGTTG TGGTTCCACC TGTTCTTTCA ACTCGGGTTT AGAACACTGT TTTGAGTGTG
 197  LeuGlyTh rGlnThrTyr IleCysAsnV alAsnHisLy sProSerAsn ThrLysValA spLysLysVa lGluProLys SerCysAspL ysThrHisThr
                                                                                                  end of heavy chain

2001 CTAGAGTGGC GGTGGCTCTG GTTCCGGTGA TTTTGATTAT GAAAAGATGG CAAACGCTAA TAAGGGGGCT ATGACCGAAA ATGCCGATGA AAACGCGCTA
     GATCTCACCG CCACCGAGAC CAAGGCCACT AAAACTAATA CTTTTCTACC GTTTGCGATT ATTCCCCCGA TACTGGCTTT TACGGCTACT TTTGCGCGAT
 230  AM*SerGly GlyGlySerG lySerGlyAs pPheAspTyr GluLysMetA laAsnAlaAs nLysGlyAla MetThrGluA snAlaAspGl uAsnAlaLeu
      fusion to g3p C-terminal domain

2101 CAGTCTGACG CTAAAGGCAA ACTTGATTCT GTCGCTACTG ATTACGGTGC TGCTATCGAT GGTTTCATTG GTGACGTTTC CGGCCTTGCT AATGGTAATG
     GTCAGACTGC GATTTCCGTT TGAACTAAGA CAGCGATGAC TAATGCCACG ACGATAGCTA CCAAAGTAAC CACTGCAAAG GCCGGAACGA TTACCATTAC
 263 GlnSerAspA laLysGlyLy sLeuAspSer ValAlaThrA spTyrGlyAl aAlaIleAsp GlyPheIleG lyAspValSe rGlyLeuAla AsnGlyAsnGly

2201 GTGCTACTGG TGATTTTGCT GGCTCTAATT CCCAAATGGC TCAAGTCGGT GACGGTGATA ATTCACCTTT AATGAATAAT TTCCGTCAAT ATTTACCTTC
     CACGATGACC ACTAAAACGA CCGAGATTAA GGGTTTACCG AGTTCAGCCA CTGCCACTAT TAAGTGGAAA TTACTTATTA AAGGCAGTTA TAAATGGAAG
 297  AlaThrGl yAspPheAla GlySerAsnS erGlnMetAl aGlnValGly AspGlyAspA snSerProLe uMetAsnAsn PheArgGlnT yrLeuProSer

2301 CCTCCCTCAA TCGGTTGAAT GTCGCCCTTT TGTCTTTAGC GCTGGTAAAC CATATGAATT TTCTATTGAT TGTGACAAAA TAAACTTATT CCGTGGTGTC
     GGAGGGAGTT AGCCAACTTA CAGCGGGAAA ACAGAAATCG CGACCATTTG GTATACTTAA AAGATAACTA ACACTGTTTT ATTTGAATAA GGCACCACAG
 330  LeuProGln SerValGluC ysArgProPh eValPheSer AlaGlyLysP roTyrGluPh eSerIleAsp CysAspLysI leAsnLeuPh eArgGlyVal

2401 TTTGCGTTTC TTTTATATGT TGCCACCTTT ATGTATGTAT TTTCTACGTT TGCTAACATA CTGCGTAATA AGGAGTCTTA ATCATGCCAG TTCTTTTGGC
     AAACGCAAAG AAAATATACA ACGGTGGAAA TACATACATA AAAGATGCAA ACGATTGTAT GACGCATTAT TCCTCAGAAT TAGTACGGTC AAGAAAACCG
 363 PheAlaPheL euLeuTyrVa lAlaThrPhe MetTyrValP heSerThrPh eAlaAsnIle LeuArgAsnL ysGluSerOC *
                                                                                end of g3p domain

2501 TAGCGCCGCC CTATACCTTG TCTGCCTCCC CGCGTTGCGT CGCGGTGCAT GGAGCCGGGC CACCTCGACC TGAATGGAAG CCGGCGGCAC CTCGCTAACG
     ATCGCGGCGG GATATGGAAC AGACGGAGGG GCGCAACGCA GCGCCACGTA CCTCGGCCCG GTGGAGCTGG ACTTACCTTC GGCCGCCGTG GAGCGATTGC

2601 GATTCACCAC TCCAAGAATT GGAGCCAATC AATTCTTGCG GAGAACTGTG AATGCGCAAA CCAACCCTTG GCAGAACATA TCCATCGCGT CCGCCATCTC
     CTAAGTGGTG AGGTTCTTAA CCTCGGTTAG TTAAGAACGC CTCTTGACAC TTACGCGTTT GGTTGGGAAC CGTCTTGTAT AGGTAGCGCA GGCGGTAGAG

2701 CAGCAGCCGC ACGCGGCGCA TCTCGGGCAG CGTTGGGTCC TGGCCACGGG TGCGCATGAT CGTGCTCCTG TCGTTGAGGA CCCGGCTAGG CTGGCGGGGT
     GTCGTCGGCG TGCGCCGCGT AGAGCCCGTC GCAACCCAGG ACCGGTGCCC ACGCGTACTA GCACGAGGAC AGCAACTCCT GGGCCGATCC GACCGCCCCA
```

FIG._10C

```
2801 TGCCTTACTG GTTAGCAGAA TGAATCACCG ATACGCGAGC GAACGTGAAG CGACTGCTGC TGCAAAACGT CTGCGACCTG AGCAACAACA TGAATGGTCT
     ACGGAATGAC CAATCGTCTT ACTTAGTGGC TATGCGCTCG CTTGCACTTC GCTGACGACG ACGTTTTGCA GACGCTGGAC TCGTTGTTGT ACTTACCAGA

2901 TCGGTTTCCG TGTTTCGTAA AGTCTGGAAA CGCGGAAGTC AGCGCCCTGC ACCATTATGT TCCGGATCTG CATCGCAGGA TGCTGCTGGC TACCCTGTGG
     AGCCAAAGGC ACAAAGCATT TCAGACCTTT GCGCCTTCAG TCGCGGGACG TGGTAATACA AGGCCTAGAC GTAGCGTCCT ACGACGACCG ATGGGACACC

3001 AACACCTACA TCTGTATTAA CGAAGCGCTG GCATTGACCC TGAGTGATTT TTCTCTGGTC CCGCCGCATC CATACCGCCA GTTGTTTACC CTCACAACGT
     TTGTGGATGT AGACATAATT GCTTCGCGAC CGTAACTGGG ACTCACTAAA AAGAGACCAG GGCGGCGTAG GTATGGCGGT CAACAAATGG GAGTGTTGCA

3101 TCCAGTAACC GGGCATGTTC ATCATCAGTA ACCCGTATCG TGAGCATCCT CTCTCGTTTC ATCGGTATCA TTACCCCCAT GAACAGAAAT TCCCCCTTAC
     AGGTCATTGG CCCGTACAAG TAGTAGTCAT TGGGCATAGC ACTCGTAGGA GAGAGCAAAG TAGCCATAGT AATGGGGGTA CTTGTCTTTA AGGGGGAATG

3201 ACGGAGGCAT CAAGTGACCA AACAGGAAAA AACCGCCCTT AACATGGCCC GCTTTATCAG AAGCCAGACA TTAACGCTTC TGGAGAAACT CAACGAGCTG
     TGCCTCCGTA GTTCACTGGT TTGTCCTTTT TTGGCGGGAA TTGTACCGGG CGAAATAGTC TTCGGTCTGT AATTGCGAAG ACCTCTTTGA GTTGCTCGAC

3301 GACGCGGATG AACAGGCAGA CATCTGTGAA TCGCTTCACG ACCACGCTGA TGAGCTTTAC CGCAGGATCC GGAAATTGTA AACGTTAATA TTTTGTTAAA
     CTGCGCCTAC TTGTCCGTCT GTAGACACTT AGCGAAGTGC TGGTGCGACT ACTCGAAATG GCGTCCTAGG CCTTTAACAT TTGCAATTAT AAAACAATTT

3401 ATTCGCGTTA AATTTTTGTT AAATCAGCTC ATTTTTTAAC CAATAGGCCG AAATCGGCAA AATCCCTTAT AAATCAAAAG AATAGACCGA GATAGGGTTG
     TAAGCGCAAT TTAAAAACAA TTTAGTCGAG TAAAAAATTG GTTATCCGGC TTTAGCCGTT TTAGGGAATA TTTAGTTTTC TTATCTGGCT CTATCCCAAC

3501 AGTGTTGTTC CAGTTTGGAA CAAGAGTCCA CTATTAAAGA ACGTGGACTC CAACGTCAAA GGGCGAAAAA CCGTCTATCA GGGCTATGGC CCACTACGTG
     TCACAACAAG GTCAAACCTT GTTCTCAGGT GATAATTTCT TGCACCTGAG GTTGCAGTTT CCCGCTTTTT GGCAGATAGT CCCGATACCG GGTGATGCAC

3601 AACCATCACC CTAATCAAGT TTTTTGGGGT CGAGGTGCCG TAAAGCACTA AATCGGAACC CTAAAGGGAG CCCCCGATTT AGAGCTTGAC GGGGAAAGCC
     TTGGTAGTGG GATTAGTTCA AAAAACCCCA GCTCCACGGC ATTTCGTGAT TTAGCCTTGG GATTTCCCTC GGGGGCTAAA TCTCGAACTG CCCCTTTCGG

3701 GGCGAACGTG GCGAGAAAGG AAGGGAAGAA AGCGAAAGGA GCGGGCGCTA GGGCGCTGGC AAGTGTAGCG GTCACGCTGC GCGTAACCAC CACACCCGCC
     CCGCTTGCAC CGCTCTTTCC TTCCCTTCTT TCGCTTTCCT CGCCCGCGAT CCCGCGACCG TTCACATCGC CAGTGCGACG CGCATTGGTG GTGTGGGCGG

3801 GCGCTTAATG CGCCGCTACA GGGCGCGTCC GGATCCTGCC TCGCGCGTTT CGGTGATGAC GGTGAAAACC TCTGACACAT GCAGCTCCCG GAGACGGTCA
     CGCGAATTAC GCGGCGATGT CCCGCGCAGG CCTAGGACGG AGCGCGCAAA GCCACTACTG CCACTTTTGG AGACTGTGTA CGTCGAGGGC CTCTGCCAGT

3901 CAGCTTGTCT GTAAGCGGAT GCCGGGAGCA GACAAGCCCG TCAGGGCGCG TCAGCGGGTG TTGGCGGGTG TCGGGGCGCA GCCATGACCC AGTCACGTAG
     GTCGAACAGA CATTCGCCTA CGGCCCTCGT CTGTTCGGGC AGTCCCGCGC AGTCGCCCAC AACCGCCCAC AGCCCCGCGT CGGTACTGGG TCAGTGCATC
```

FIG._10D

```
4001 CGATAGCGGA GTGTATACTG GCTTAACTAT GCGGCATCAG AGCAGATTGT ACTGAGAGTG CACCATATGC GGTGTGAAAT ACCGCACAGA TGCGTAAGGA
     GCTATCGCCT CACATATGAC CGAATTGATA CGCCGTAGTC TCGTCTAACA TGACTCTCAC GTGGTATACG CCACACTTTA TGGCGTGTCT ACGCATTCCT

4101 GAAAATACCG CATCAGGCGC TCTTCCGCTT CCTCGCTCAC TGACTCGCTG CGCTCGGTCG TTCGGCTGCG GCGAGCGGTA TCAGCTCACT CAAAGGCGGT
     CTTTTATGGC GTAGTCCGCG AGAAGGCGAA GGAGCGAGTG ACTGAGCGAC GCGAGCCAGC AAGCCGACGC CGCTCGCCAT AGTCGAGTGA GTTTCCGCCA

4201 AATACGGTTA TCCACAGAAT CAGGGGATAA CGCAGGAAAG AACATGTGAG CAAAAGGCCA GCAAAAGGCC AGGAACCGTA AAAAGGCCGC GTTGCTGGCG
     TTATGCCAAT AGGTGTCTTA GTCCCCTATT GCGTCCTTTC TTGTACACTC GTTTTCCGGT CGTTTTCCGG TCCTTGGCAT TTTTCCGGCG CAACGACCGC

4301 TTTTTCCATA GGCTCCGCCC CCCTGACGAG CATCACAAAA ATCGACGCTC AAGTCAGAGG TGGCGAAACC CGACAGGACT ATAAAGATAC CAGGCGTTTC
     AAAAAGGTAT CCGAGGCGGG GGGACTGCTC GTAGTGTTTT TAGCTGCGAG TTCAGTCTCC ACCGCTTTGG GCTGTCCTGA TATTTCTATG GTCCGCAAAG

4401 CCCCTGGAAG CTCCCTCGTG CGCTCTCCTG TTCCGACCCT GCCGCTTACC GGATACCTGT CCGCCTTTCT CCCTTCGGGA AGCGTGGCGC TTTCTCATAG
     GGGGACCTTC GAGGGAGCAC GCGAGAGGAC AAGGCTGGGA CGGCGAATGG CCTATGGACA GGCGGAAAGA GGGAAGCCCT TCGCACCGCG AAAGAGTATC

4501 CTCACGCTGT AGGTATCTCA GTTCGGTGTA GGTCGTTCGC TCCAAGCTGG GCTGTGTGCA CGAACCCCCC GTTCAGCCCG ACCGCTGCGC CTTATCCGGT
     GAGTGCGACA TCCATAGAGT CAAGCCACAT CCAGCAAGCG AGGTTCGACC CGACACACGT GCTTGGGGGG CAAGTCGGGC TGGCGACGCG GAATAGGCCA

4601 AACTATCGTC TTGAGTCCAA CCCGGTAAGA CACGACTTAT CGCCACTGGC AGCAGCCACT GGTAACAGGA TTAGCAGAGC GAGGTATGTA GGCGGTGCTA
     TTGATAGCAG AACTCAGGTT GGGCCATTCT GTGCTGAATA GCGGTGACCG TCGTCGGTGA CCATTGTCCT AATCGTCTCG CTCCATACAT CCGCCACGAT

4701 CAGAGTTCTT GAAGTGGTGG CCTAACTACG GCTACACTAG AAGGACAGTA TTTGGTATCT GCGCTCTGCT GAAGCCAGTT ACCTTCGGAA AAAGAGTTGG
     GTCTCAAGAA CTTCACCACC GGATTGATGC CGATGTGATC TTCCTGTCAT AAACCATAGA CGCGAGACGA CTTCGGTCAA TGGAAGCCTT TTTCTCAACC

4801 TAGCTCTTGA TCCGGCAAAC AAACCACCGC TGGTAGCGGT GGTTTTTTTG TTTGCAAGCA GCAGATTACG CGCAGAAAAA AAGGATCTCA AGAAGATCCT
     ATCGAGAACT AGGCCGTTTG TTTGGTGGCG ACCATCGCCA CCAAAAAAAC AAACGTTCGT CGTCTAATGC GCGTCTTTTT TTCCTAGAGT TCTTCTAGGA
4901 TTGATCTTTT CTACGGGGTC TGACGCTCAG TGGAACGAAA ACTCACGTTA AGGGATTTTG GTCATGAGAT TATCAAAAAG GATCTTCACC TAGATCCTTT
     AACTAGAAAA GATGCCCCAG ACTGCGAGTC ACCTTGCTTT TGAGTGCAAT TCCCTAAAAC CAGTACTCTA ATAGTTTTTC CTAGAAGTGG ATCTAGGAAA

5001 TAAATTAAAA ATGAAGTTTT AAATCAATCT AAAGTATATA TGAGTAAACT TGGTCTGACA GTTACCAATG CTTAATCAGT GAGGCACCTA TCTCAGCGAT
     ATTTAATTTT TACTTCAAAA TTTAGTTAGA TTTCATATAT ACTCATTTGA ACCAGACTGT CAATGGTTAC GAATTAGTCA CTCCGTGGAT AGAGTCGCTA

5101 CTGTCTATTT CGTTCATCCA TAGTTGCCTG ACTCCCCGTC GTGTAGATAA CTACGATACG GGAGGGCTTA CCATCTGGCC CCAGTGCTGC AATGATACCG
     GACAGATAAA GCAAGTAGGT ATCAACGGAC TGAGGGGCAG CACATCTATT GATGCTATGC CCTCCCGAAT GGTAGACCGG GGTCACGACG TTACTATGGC
```

FIG._10E

```
5201 CGAGACCCAC GCTCACCGGC TCCAGATTTA TCAGCAATAA ACCAGCCAGC CGGAAGGGCC GAGCGCAGAA GTGGTCCTGC AACTTTATCC GCCTCCATCC
     GCTCTGGGTG CGAGTGGCCG AGGTCTAAAT AGTCGTTATT TGGTCGGTCG GCCTTCCCGG CTCGCGTCTT CACCAGGACG TTGAAATAGG CGGAGGTAGG

5301 AGTCTATTAA TTGTTGCCGG GAAGCTAGAG TAAGTAGTTC GCCAGTTAAT AGTTTGCGCA ACGTTGTTGC CATTGCTGCA GGCATCGTGG TGTCACGCTC
     TCAGATAATT AACAACGGCC CTTCGATCTC ATTCATCAAG CGGTCAATTA TCAAACGCGT TGCAACAACG GTAACGACGT CCGTAGCACC ACAGTGCGAG

5401 GTCGTTTGGT ATGGCTTCAT TCAGCTCCGG TTCCCAACGA TCAAGGCGAG TTACATGATC CCCCATGTTG TGCAAAAAAG CGGTTAGCTC CTTCGGTCCT
     CAGCAAACCA TACCGAAGTA AGTCGAGGCC AAGGGTTGCT AGTTCCGCTC AATGTACTAG GGGGTACAAC ACGTTTTTTC GCCAATCGAG GAAGCCAGGA

5501 CCGATCGTTG TCAGAAGTAA GTTGGCCGCA GTGTTATCAC TCATGGTTAT GGCAGCACTG CATAATTCTC TTACTGTCAT GCCATCCGTA AGATGCTTTT
     GGCTAGCAAC AGTCTTCATT CAACCGGCGT CACAATAGTG AGTACCAATA CCGTCGTGAC GTATTAAGAG AATGACAGTA CGGTAGGCAT TCTACGAAAA

5601 CTGTGACTGG TGAGTACTCA ACCAAGTCAT TCTGAGAATA GTGTATGCGG CGACCGAGTT GCTCTTGCCC GGCGTCAACA CGGGATAATA CCGCGCCACA
     GACACTGACC ACTCATGAGT TGGTTCAGTA AGACTCTTAT CACATACGCC GCTGGCTCAA CGAGAACGGG CCGCAGTTGT GCCCTATTAT GGCGCGGTGT

5701 TAGCAGAACT TTAAAAGTGC TCATCATTGG AAAACGTTCT TCGGGGCGAA AACTCTCAAG GATCTTACCG CTGTTGAGAT CCAGTTCGAT GTAACCCACT
     ATCGTCTTGA AATTTTCACG AGTAGTAACC TTTTGCAAGA AGCCCCGCTT TTGAGAGTTC CTAGAATGGC GACAACTCTA GGTCAAGCTA CATTGGGTGA

5801 CGTGCACCCA ACTGATCTTC AGCATCTTTT ACTTTCACCA GCGTTTCTGG GTGAGCAAAA ACAGGAAGGC AAAATGCCGC AAAAAAGGGA ATAAGGGCGA
     GCACGTGGGT TGACTAGAAG TCGTAGAAAA TGAAAGTGGT CGCAAAGACC CACTCGTTTT TGTCCTTCCG TTTTACGGCG TTTTTTCCCT TATTCCCGCT

5901 CACGGAAATG TTGAATACTC ATACTCTTCC TTTTTCAATA TTATTGAAGC ATTTATCAGG GTTATTGTCT CATGAGCGGA TACATATTTG AATGTATTTA
     GTGCCTTTAC AACTTATGAG TATGAGAAGG AAAAAGTTAT AATAACTTCG TAAATAGTCC CAATAACAGA GTACTCGCCT ATGTATAAAC TTACATAAAT

6001 GAAAAATAAA CAAATAGGGG TTCCGCGCAC ATTTCCCCGA AAAGTGCCAC CTGACGTCTA AGAAACCATT ATTATCATGA CATTAACCTA TAAAAATAGG
     CTTTTTATTT GTTTATCCCC AAGGCGCGTG TAAAGGGGCT TTTCACGGTG GACTGCAGAT TCTTTGGTAA TAATAGTACT GTAATTGGAT ATTTTTATCC

6101 CGTATCACGA GGCCCTTTCG TCTTCAA
     GCATAGTGCT CCGGGAAAGC AGAAGTT
```

FIG._10F

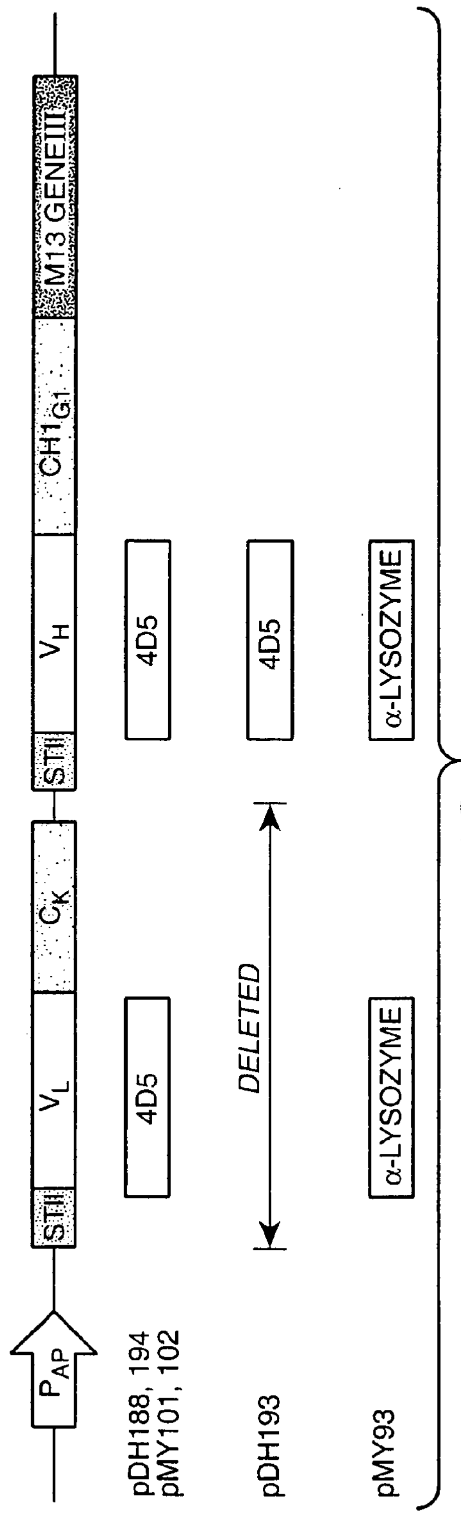
FIG._11A
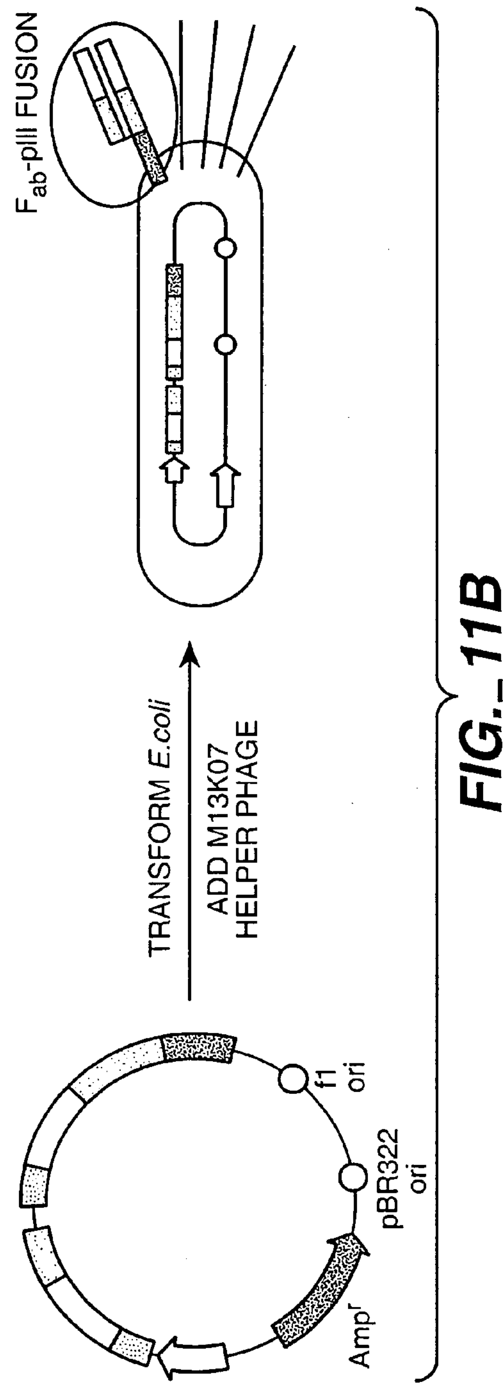
FIG._11B (E25) - LIGHT CHAIN

DIQLTQSPSS LSASVGDRVT ITCRASQSVD YDGDSYMNWY QQKPGKAPKL LIYAASYLES GVPSRFSGSG
SGTDFTLTIS SLQPEDFATY YCQQSHEDPY TFGQGTKVEI KRTVAAPSVF IFPPSDEQLK SGTASVVCLL
NNFYPREAKV QWKVDNALQS GNSQESVTEQ DSKDSTYSLS STLTLSKADY EKHKVYACEV THQGLSSPVT
KSFNRGEC (E25) - HEAVY CHAIN

EVQLVESGGG LVQPGGSLRL SCAVSGYSIT SGYSWNWIRQ APGKGLEWVA SITYDGSTNY NPSVKGRITI
SRDDSKNTFY LQMNSLRAED TAVYYCARGS HYFGHWHFAV WGQGTLVTVS SASTKGPSVF PLAPSSKSTS
GGTAALGCLV KDYFPEPVTV SWNSGALTSG VHTFPAVLQS SGLYSLSSVV TVPSSSLGTQ TYICNVNHKP
SNTKVDKKVE PKSCDKTHTC PPCPAPELLG GPSVFLFPPK PKDTLMISRT PEVTCVVVDV SHEDPEVKFN
WYVDGVEVHN AKTKPREEQY NSTYRVVSVL TVLHQDWLNG KEYKCKVSNK ALPAPIEKTI SKAKGQPREP
QVYTLPPSRE EMTKNQVSLT CLVKGFYPSD IAVEWESNGQ PENNYKTTPP VLDSDGSFFL YSKLTVDKSR
WQQGNVFSCS VMHEALHNHY TQKSLSLSPG K (E26) - LIGHT CHAIN

DIQLTQSPSS LSASVGDRVT ITCRASKPVD GEGDSYLNWY QQKPGKAPKL LIYAASYLES GVPSRFSGSG
SGTDFTLTIS SLQPEDFATY YCQQSHEDPY TFGQGTKVEI KRTVAAPSVF IFPPSDEQLK SGTASVVCLL
NNFYPREAKV QWKVDNALQS GNSQESVTEQ DSKDSTYSLS STLTLSKADY EKHKVYACEV THQGLSSPVT
KSFNRGEC (E26) - HEAVY CHAIN

EVQLVESGGG LVQPGGSLRL SCAVSGYSIT SGYSWNWIRQ APGKGLEWVA SITYDGSTNY NPSVKGRITI
SRDDSKNTFY LQMNSLRAED TAVYYCARGS HYFGHWHFAV WGQGTLVTVS SASTKGPSVF PLAPSSKSTS
GGTAALGCLV KDYFPEPVTV SWNSGALTSG VHTFPAVLQS SGLYSLSSVV TVPSSSLGTQ TYICNVNHKP
SNTKVDKKVE PKSCDKTHTC PPCPAPELLG GPSVFLFPPK PKDTLMISRT PEVTCVVVDV SHEDPEVKFN
WYVDGVEVHN AKTKPREEQY NSTYRVVSVL TVLHQDWLNG KEYKCKVSNK ALPAPIEKTI SKAKGQPREP
QVYTLPPSRE EMTKNQVSLT CLVKGFYPSD IAVEWESNGQ PENNYKTTPP VLDSDGSFFL YSKLTVDKSR
WQQGNVFSCS VMHEALHNHY TQKSLSLSPG K (E27) - LIGHT CHAIN

DIQLTQSPSS LSASVGDRVT ITCRASKPVD GEGDSYLNWY QQKPGKAPKL LIYAASYLES GVPSRFSGSG
SGTDFTLTIS SLQPEDFATY YCQQSHEDPY TFGQGTKVEI KRTVAAPSVF IFPPSDEQLK SGTASVVCLL
NNFYPREAKV QWKVDNALQS GNSQESVTEQ DSKDSTYSLS STLTLSKADY EKHKVYACEV THQGLSSPVT
KSFNRGEC (E27) - HEAVY CHAIN

EVQLVESGGG LVQPGGSLRL SCAVSGYSIT SGYSWNWIRQ APGKGLEWVA SIKYSGETKY NPSVKGRITI
SRDDSKNTFY LQMNSLRAED TAVYYCARGS HYFGHWHFAV WGQGTLVTVS SASTKGPSVF PLAPSSKSTS
GGTAALGCLV KDYFPEPVTV SWNSGALTSG VHTFPAVLQS SGLYSLSSVV TVPSSSLGTQ TYICNVNHKP
SNTKVDKKVE PKSCDKTHTC PPCPAPELLG GPSVFLFPPK PKDTLMISRT PEVTCVVVDV SHEDPEVKFN
WYVDGVEVHN AKTKPREEQY NSTYRVVSVL TVLHQDWLNG KEYKCKVSNK ALPAPIEKTI SKAKGQPREP
QVYTLPPSRE EMTKNQVSLT CLVKGFYPSD IAVEWESNGQ PENNYKTTPP VLDSDGSFFL YSKLTVDKSR
WQQGNVFSCS VMHEALHNHY TQKSLSLSPG K

FIG._12

LIGHT CHAIN

E26

DIQLTQSPSS LSASVGDRVT ITCRASKPVD GEGDSYLNWY QQKPGKAPKL LIYAASYLES
GVPSRFSGSG SGTDFTLTIS SLQPEDFATY YCQQSHEDPY TFGQGTKVEI KRTVAAPSVF
IFPPSDEQLK SGTASVVCLL NNFYPREAKV QWKVDNALQS GNSQESVTEQ DSKDSTYSLS
STLTLSKADY EKHKVYACEV THQGLSSPVT KSFNRGEC

E27

DIQLTQSPSS LSASVGDRVT ITCRASKPVD GEGDSYLNWY QQKPGKAPKL LIYAASYLES
GVPSRFSGSG SGTDFTLTIS SLQPEDFATY YCQQSHEDPY TFGQGTKVEI KRTVAAPSVF
IFPPSDEQLK SGTASVVCLL NNFYPREAKV QWKVDNALQS GNSQESVTEQ DSKDSTYSLS
STLTLSKADY EKHKVYACEV THQGLSSPVT KSFNRGEC

HEAVY CHAIN

E26

EVQLVESGGG LVQPGGSLRL SCAVSGYSIT SGYSWNWIRQ APGKGLEWVA SITYDGSTNY
NPSVKGRITI SRDDSKNTFY LQMNSLRAED TAVYYCARGS HYFGHWHFAV WGQGTLVTVS
SASTKGPSVF PLAPSSKSTS GGTAALGCLV KDYFPEPVTV SWNSGALTSG VHTFPAVLQS
SGLYSLSSVV TVPSSSLGTQ TYICNVNHKP SNTKVDKKVE PKSCDKTHT

E27

EVQLVESGGG LVQPGGSLRL SCAVSGYSIT SGYSWNWIRQ APGKGLEWVA SIKYSGETKY
NPSVKGRITI SRDDSKNTFY LQMNSLRAED TAVYYCARGS HYFGHWHFAV WGQGTLVTVS
SASTKGPSVF PLAPSSKSTS GGTAALGCLV KDYFPEPVTV SWNSGALTSG VHTFPAVLQS
SGLYSLSSVV TVPSSSLGTQ TYICNVNHKP SNTKVDKKVE PKSCDKTHT

EVQLVESGGG LVQPGGSLRL SCAVSGYSIT SGYSWNWIRQ APGKGLEWVA SITYDGSTNY
NPSVKGRITI SRDDSKNTFY LQMNSLRAED TAVYYCARGS HYFGHWHFAV WGQGTLVTVS
SEGGGSEGGG SEGGGSDIQL TQSPSSLSAS VGDRVTITCR ASKPVDGEGD SYLNWYQQKP
GKAPKLLIYA ASYLESGVPS RFSGSGSGTD FTLTISSLQP EDFATYYCQQ SHEDPYTFGQ
GTKVEIKR

E27

EVQLVESGGG LVQPGGSLRL SCAVSGYSIT SGYSWNWIRQ APGKGLEWVA SIKYSGETKY
NPSVKGRITI SRDDSKNTFY LQMNSLRAED TAVYYCARGS HYFGHWHFAV WGQGTLVTVS
SEGGGSEGGG SEGGGSDIQL TQSPSSLSAS VGDRVTITCR ASKPVDGEGD SYLNWYQQKP
GKAPKLLIYA ASYLESGVPS RFSGSGSGTD FTLTISSLQP EDFATYYCQQ SHEDPYTFGQ
GTKVEIKR

*FIG._14*

LIGHT CHAIN

E26

DIQLTQSPSS LSASVGDRVT ITCRASKPVD GEGDSYLNWY QQKPGKAPKL LIYAASYLES
GVPSRFSGSG SGTDFTLTIS SLQPEDFATY YCQQSHEDPY TFGQGTKVEI KRTVAAPSVF
IFPPSDEQLK SGTASVVCLL NNFYPREAKV QWKVDNALQS GNSQESVTEQ DSKDSTYSLS
STLTLSKADY EKHKVYACEV THQGLSSPVT KSFNRGEC

E27

DIQLTQSPSS LSASVGDRVT ITCRASKPVD GEGDSYLNWY QQKPGKAPKL LIYAASYLES
GVPSRFSGSG SGTDFTLTIS SLQPEDFATY YCQQSHEDPY TFGQGTKVEI KRTVAAPSVF
IFPPSDEQLK SGTASVVCLL NNFYPREAKV QWKVDNALQS GNSQESVTEQ DSKDSTYSLS
STLTLSKADY EKHKVYACEV THQGLSSPVT KSFNRGEC

HEAVY CHAIN

E26

EVQLVESGGG LVQPGGSLRL SCAVSGYSIT SGYSWNWIRQ APGKGLEWVA SITYDGSTNY
NPSVKGRITI SRDDSKNTFY LQMNSLRAED TAVYYCARGS HYFGHWHFAV WGQGTLVTVS
SASTKGPSVF PLAPSSKSTS GGTAALGCLV KDYFPEPVTV SWNSGALTSG VHTFPAVLQS
SGLYSLSSVV TVPSSSLGTQ TYICNVNHKP SNTKVDKKVE PKSCDKTHTC PPC

E27

EVQLVESGGG LVQPGGSLRL SCAVSGYSIT SGYSWNWIRQ APGKGLEWVA SIKYSGETKY
NPSVKGRITI SRDDSKNTFY LQMNSLRAED TAVYYCARGS HYFGHWHFAV WGQGTLVTVS
SASTKGPSVF PLAPSSKSTS GGTAALGCLV KDYFPEPVTV SWNSGALTSG VHTFPAVLQS
SGLYSLSSVV TVPSSSLGTQ TYICNVNHKP SNTKVDKKVE PKSCDKTHTC PPC

*FIG._15*

SEQUENCE LISTING

<160> NUMBER OF SEQ ID NOS: 44

<210> SEQ ID NO 1
<211> LENGTH: 6127
<212> TYPE: DNA
<213> ORGANISM: Artificial
<220> FEATURE:
<221> NAME/KEY: Artificial
<222> LOCATION: 1-6127
<223> OTHER INFORMATION: Expression plasmid

<400> SEQUENCE: 1

```
gaattcaact tctccatact ttggataagg aaatacagac atgaaaaatc          50

tcattgctga gttgttattt aagcttgccc aaaaagaaga agagtcgaat         100

gaactgtgtg cgcaggtaga agctttggag attatcgtca ctgcaatgct         150

tcgcaatatg gcgcaaaatg accaacagcg gttgattgat caggtagagg         200

gggcgctgta cgaggtaaag cccgatgcca gcattcctga cgacgatacg         250

gagctgctgc gcgattacgt aaagaagtta ttgaagcatc ctcgtcagta         300

aaaagttaat cttttcaaca gctgtcataa agttgtcacg gccgagactt         350

atagtcgctt tgtttttatt ttttaatgta tttgtaacta gaattcgagc         400

tcggtacccg gggatcctct cgaggttgag gtgattttat gaaaaagaat         450

atcgcatttc ttcttgcatc tatgttcgtt ttttctattg ctacaaacgc         500

gtacgctgat atccagctga cccagtcccc gagctccctg tccgcctctg         550

tgggcgatag ggtcaccatc acctgccgtg ccagtcagag cgtcgattac         600

gaaggtgata gctacctgaa ctggtatcaa cagaaaccag gaaaagctcc         650

gaaactactg atttacgcgg cctcgtacct ggagtctgga gtcccttctc         700

gcttctctgg atccggttct gggacggatt tcactctgac catcagcagt         750

ctgcagccag aagacttcgc aacttattac tgtcagcaaa gtcacgagga         800

tccgtacaca tttggacagg gtaccaaggt ggagatcaaa cgaactgtgg         850

ctgcaccatc tgtcttcatc ttcccgccat ctgatgagca gttgaaatct         900
```

-continued

```
ggaactgctt ctgttgtgtg cctgctgaat aacttctatc ccagagaggc         950
caaagtacag tggaaggtgg ataacgccct ccaatcgggt aactcccagg        1000
agagtgtcac agagcaggac agcaaggaca gcacctacag cctcagcagc        1050
accctgacgc tgagcaaagc agactacgag aaacacaaag tctacgcctg        1100
cgaagtcacc catcagggcc tgagctcgcc cgtcacaaag agcttcaaca        1150
ggggagagtg ttaagctgat cctctacgcc ggacgcatcg tggccctagt        1200
acgcaagttc acgtaaaaag ggtatctaga ggttgaggtg attttatgaa        1250
aaagaatatc gcatttcttc ttgcatctat gttcgttttt tctattgcta        1300
caaacgcgta cgctgaggtt cagctggtgg agtctggcgg tggcctggtg        1350
cagccagggg gctcactccg tttgtcctgt gcagtttctg gctactccat        1400
cacctccgga tacagctgga actggatccg tcaggccccg ggtaagggcc        1450
tggaatgggt tgcatcgatt acgtatgacg gatcgactaa ctataaccct        1500
agcgtcaagg gccgtatcac tataagtcgc gacgattcca aaaacacatt        1550
ctacctgcag atgaacagcc tgcgtgctga ggacactgcc gtctattatt        1600
gtgctcgagg cagccactat ttcggtcact ggcacttcgc cgtgtggggt        1650
caaggaaccc tggtcaccgt ctcctcggcc tccaccaagg gcccatcggt        1700
cttcccccta gcaccctcct ccaagagcac ctctgggggc acagcggccc        1750
tgggctgcct ggtcaaggac tacttccccg aaccggtgac ggtgtcgtgg        1800
aactcaggcg ccctgaccag cggcgtgcac accttcccgg ctgtcctaca        1850
gtcctcagga ctctactccc tcagcagcgt ggtgaccgtg ccctccagca        1900
gcttgggcac ccagacctac atctgcaacg tgaatcacaa gcccagcaac        1950
accaaggtgg acaagaaagt tgagcccaaa tcttgtgaca aaactcacac        2000
ctagagtggc ggtggctctg gttccggtga ttttgattat gaaaagatgg        2050
caaacgctaa taagggggct atgaccgaaa atgccgatga aaacgcgcta        2100
cagtctgacg ctaaaggcaa acttgattct gtcgctactg attacggtgc        2150
tgctatcgat ggtttcattg gtgacgtttc cggccttgct aatggtaatg        2200
gtgctactgg tgattttgct ggctctaatt cccaaatggc tcaagtcggt        2250
gacggtgata attcaccttt aatgaataat ttccgtcaat atttaccttc        2300
cctccctcaa tcggttgaat gtcgcccttt tgtctttagc gctggtaaac        2350
catatgaatt ttctattgat tgtgacaaaa taaacttatt ccgtggtgtc        2400
tttgcgtttc ttttatatgt tgccaccttt atgtatgtat tttctacgtt        2450
tgctaacata ctgcgtaata aggagtctta atcatgccag ttcttttggc        2500
tagcgccgcc ctataccttg tctgcctccc cgcgttgcgt cgcggtgcat        2550
ggagccgggc cacctcgacc tgaatggaag ccggcggcac ctcgctaacg        2600
gattcaccac tccaagaatt ggagccaatc aattcttgcg gagaactgtg        2650
aatgcgcaaa ccaacccttg gcagaacata tccatcgcgt ccgccatctc        2700
cagcagccgc acgcggcgca tctcgggcag cgttgggtcc tggccacggg        2750
tgcgcatgat cgtgctcctg tcgttgagga cccggctagg ctggcggggt        2800
tgccttactg gttagcagaa tgaatcaccg atacgcgagc gaacgtgaag        2850
cgactgctgc tgcaaaacgt ctgcgacctg agcaacaaca tgaatggtct        2900
```

-continued

```
tcggtttccg tgtttcgtaa agtctggaaa cgcggaagtc agcgccctgc      2950
accattatgt tccggatctg catcgcagga tgctgctggc taccctgtgg      3000
aacacctaca tctgtattaa cgaagcgctg gcattgaccc tgagtgattt      3050
ttctctggtc ccgccgcatc cataccgcca gttgtttacc ctcacaacgt      3100
tccagtaacc gggcatgttc atcatcagta acccgtatcg tgagcatcct      3150
ctctcgtttc atcggtatca ttacccccat gaacagaaat tcccccttac      3200
acggaggcat caagtgacca aacaggaaaa aaccgccctt aacatggccc      3250
gctttatcag aagccagaca ttaacgcttc tggagaaact caacgagctg      3300
gacgcggatg aacaggcaga catctgtgaa tcgcttcacg accacgctga      3350
tgagctttac cgcaggatcc ggaaattgta aacgttaata ttttgttaaa      3400
attcgcgtta aatttttgtt aaatcagctc attttttaac caataggccg      3450
aaatcggcaa aatcccttat aaatcaaaag aatagaccga gatagggttg      3500
agtgttgttc cagtttggaa caagagtcca ctattaaaga acgtggactc      3550
caacgtcaaa gggcgaaaaa ccgtctatca gggctatggc ccactacgtg      3600
aaccatcacc ctaatcaagt tttttggggt cgaggtgccg taaagcacta      3650
aatcggaacc ctaaagggag cccccgattt agagcttgac ggggaaagcc      3700
ggcgaacgtg gcgagaaagg aagggaagaa agcgaaagga gcgggcgcta      3750
gggcgctggc aagtgtagcg gtcacgctgc gcgtaaccac cacacccgcc      3800
gcgcttaatg cgccgctaca gggcgcgtcc ggatcctgcc tcgcgcgttt      3850
cggtgatgac ggtgaaaacc tctgacacat gcagctcccg gagacggtca      3900
cagcttgtct gtaagcggat gccgggagca gacaagcccg tcagggcgcg      3950
tcagcgggtg ttggcgggtg tcggggcgca gccatgaccc agtcacgtag      4000
cgatagcgga gtgtatactg gcttaactat gcggcatcag agcagattgt      4050
actgagagtg caccatatgc ggtgtgaaat accgcacaga tgcgtaagga      4100
gaaaataccg catcaggcgc tcttccgctt cctcgctcac tgactcgctg      4150
cgctcggtcg ttcggctgcg gcgagcggta tcagctcact caaaggcggt      4200
aatacggtta tccacagaat caggggataa cgcaggaaag aacatgtgag      4250
caaaaggcca gcaaaaggcc aggaaccgta aaaaggccgc gttgctggcg      4300
tttttccata ggctccgccc ccctgacgag catcacaaaa atcgacgctc      4350
aagtcagagg tggcgaaacc cgacaggact ataaagatac caggcgtttc      4400
cccctggaag ctccctcgtg cgctctcctg ttccgaccct gccgcttacc      4450
ggatacctgt ccgcctttct cccttcggga agcgtggcgc tttctcatag      4500
ctcacgctgt aggtatctca gttcggtgta ggtcgttcgc tccaagctgg      4550
gctgtgtgca cgaacccccc gttcagcccg accgctgcgc cttatccggt      4600
aactatcgtc ttgagtccaa cccggtaaga cacgacttat cgccactggc      4650
agcagccact ggtaacagga ttagcagagc gaggtatgta ggcggtgcta      4700
cagagttctt gaagtggtgg cctaactacg gctacactag aaggacagta      4750
tttggtatct gcgctctgct gaagccagtt accttcggaa aaagagttgg      4800
tagctcttga tccggcaaac aaaccaccgc tggtagcggt ggtttttttg      4850
```

-continued

```
tttgcaagca gcagattacg cgcagaaaaa aaggatctca agaagatcct           4900

ttgatctttt ctacggggtc tgacgctcag tggaacgaaa actcacgtta           4950

agggattttg gtcatgagat tatcaaaaag gatcttcacc tagatccttt           5000

taaattaaaa atgaagtttt aaatcaatct aaagtatata tgagtaaact           5050

tggtctgaca gttaccaatg cttaatcagt gaggcaccta tctcagcgat           5100

ctgtctattt cgttcatcca tagttgcctg actccccgtc gtgtagataa           5150

ctacgatacg ggagggctta ccatctggcc ccagtgctgc aatgataccg           5200

cgagacccac gctcaccggc tccagattta tcagcaataa accagccagc           5250

cggaagggcc gagcgcagaa gtggtcctgc aactttatcc gcctccatcc           5300

agtctattaa ttgttgccgg gaagctagag taagtagttc gccagttaat           5350

agtttgcgca acgttgttgc cattgctgca ggcatcgtgg tgtcacgctc           5400

gtcgtttggt atggcttcat tcagctccgg ttcccaacga tcaaggcgag           5450

ttacatgatc ccccatgttg tgcaaaaaag cggttagctc cttcggtcct           5500

ccgatcgttg tcagaagtaa gttggccgca gtgttatcac tcatggttat           5550

ggcagcactg cataattctc ttactgtcat gccatccgta agatgctttt           5600

ctgtgactgg tgagtactca accaagtcat tctgagaata gtgtatgcgg           5650

cgaccgagtt gctcttgccc ggcgtcaaca cgggataata ccgcgccaca           5700

tagcagaact ttaaaagtgc tcatcattgg aaaacgttct tcggggcgaa           5750

aactctcaag gatcttaccg ctgttgagat ccagttcgat gtaacccact           5800

cgtgcaccca actgatcttc agcatctttt actttcacca gcgtttctgg           5850

gtgagcaaaa acaggaaggc aaaatgccgc aaaaaaggga ataagggcga           5900

cacggaaatg ttgaatactc atactcttcc tttttcaata ttattgaagc           5950

atttatcagg gttattgtct catgagcgga tacatatttg aatgtattta           6000

gaaaaataaa caaatagggg ttccgcgcac atttccccga aaagtgccac           6050

ctgacgtcta agaaaccatt attatcatga cattaaccta taaaaatagg           6100

cgtatcacga ggccctttcg tcttcaa                                     6127


<210> SEQ ID NO 2
<211> LENGTH: 121
<212> TYPE: PRT
<213> ORGANISM: Mus musculus

<400> SEQUENCE: 2

Asp Val Gln Leu Gln Glu Ser Gly Pro Gly Leu Val Lys Pro Ser
  1               5                  10                  15

Gln Ser Leu Ser Leu Ala Cys Ser Val Thr Gly Tyr Ser Ile Thr
                 20                  25                  30

Ser Gly Tyr Ser Trp Asn Trp Ile Arg Gln Phe Pro Gly Asn Lys
                 35                  40                  45

Leu Glu Trp Met Gly Ser Ile Thr Tyr Asp Gly Ser Ser Asn Tyr
                 50                  55                  60

Asn Pro Ser Leu Lys Asn Arg Ile Ser Val Thr Arg Asp Thr Ser
                 65                  70                  75

Gln Asn Gln Phe Phe Leu Lys Leu Asn Ser Ala Thr Ala Glu Asp
                 80                  85                  90

Thr Ala Thr Tyr Tyr Cys Ala Arg Gly Ser His Tyr Phe Gly His
```

```
                95                  100                 105

Trp His Phe Ala Val Trp Gly Ala Gly Thr Thr Val Thr Val Ser
                110                 115                 120

Ser


<210> SEQ ID NO 3
<211> LENGTH: 121
<212> TYPE: PRT
<213> ORGANISM: Artificial
<220> FEATURE:
<221> NAME/KEY: Artificial
<222> LOCATION: 1-121
<223> OTHER INFORMATION: F(ab) sequence derived from MAE11

<400> SEQUENCE: 3

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Thr Tyr Asp Gly Ser Thr Asn Tyr
                 50                  55                  60

Ala Asp Ser Val Lys Gly Arg Phe Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser


<210> SEQ ID NO 4
<211> LENGTH: 121
<212> TYPE: PRT
<213> ORGANISM: Homo sapiens
<220> FEATURE:
<221> NAME/KEY: unsure
<222> LOCATION: 30, 104-108
<223> OTHER INFORMATION: unknown amino acid

<400> SEQUENCE: 4

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Xaa
                 20                  25                  30

Ser Asp Tyr Ala Met Ser Trp Val Arg Gln Ala Pro Gly Lys Gly
                 35                  40                  45

Leu Glu Trp Val Ala Val Ile Ser Asn Gly Ser Asp Thr Tyr Tyr
                 50                  55                  60

Ala Asp Ser Val Lys Gly Arg Phe Thr Ile Ser Arg Asp Asp Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Asp Ser Arg Phe Phe Xaa Xaa
                 95                 100                 105

Xaa Xaa Xaa Asp Val Trp Gly Gln Gly Thr Leu Val Thr Val Ser
```

-continued

```
            110                 115                 120

Ser


<210> SEQ ID NO 5
<211> LENGTH: 111
<212> TYPE: PRT
<213> ORGANISM: Mus musculus

<400> SEQUENCE: 5

Asp Ile Gln Leu Thr Gln Ser Pro Ala Ser Leu Ala Val Ser Leu
  1               5                  10                  15

Gly Gln Arg Ala Thr Ile Ser Cys Lys Ala Ser Gln Ser Val Asp
                 20                  25                  30

Tyr Asp Gly Asp Ser Tyr Met Asn Trp Tyr Gln Gln Lys Pro Gly
                 35                  40                  45

Gln Pro Pro Ile Leu Leu Ile Tyr Ala Ala Ser Tyr Leu Gly Ser
                 50                  55                  60

Glu Ile Pro Ala Arg Phe Ser Gly Ser Gly Ser Gly Thr Asp Phe
                 65                  70                  75

Thr Leu Asn Ile His Pro Val Glu Glu Glu Asp Ala Ala Thr Phe
                 80                  85                  90

Tyr Cys Gln Gln Ser His Glu Asp Pro Tyr Thr Phe Gly Ala Gly
                 95                 100                 105

Thr Lys Leu Glu Ile Lys
                110


<210> SEQ ID NO 6
<211> LENGTH: 111
<212> TYPE: PRT
<213> ORGANISM: Artificial
<220> FEATURE:
<221> NAME/KEY: Artificial
<222> LOCATION: 1-111
<223> OTHER INFORMATION: F(ab) light chain sequence derived from MAE11

<400> SEQUENCE: 6

Asp Ile Gln Leu Thr Gln Ser Pro Ser Ser Leu Ser Ala Ser Val
  1               5                  10                  15

Gly Asp Arg Val Thr Ile Thr Cys Arg Ala Ser Gln Ser Val Asp
                 20                  25                  30

Tyr Asp Gly Asp Ser Tyr Met Asn Trp Tyr Gln Gln Lys Pro Gly
                 35                  40                  45

Lys Ala Pro Lys Leu Leu Ile Tyr Ala Ala Ser Tyr Leu Glu Ser
                 50                  55                  60

Gly Val Pro Ser Arg Phe Ser Gly Ser Gly Ser Gly Thr Asp Phe
                 65                  70                  75

Thr Leu Thr Ile Ser Ser Leu Gln Pro Glu Asp Phe Ala Thr Tyr
                 80                  85                  90

Tyr Cys Gln Gln Ser His Glu Asp Pro Tyr Thr Phe Gly Gln Gly
                 95                 100                 105

Thr Lys Val Glu Ile Lys
                110


<210> SEQ ID NO 7
<211> LENGTH: 111
<212> TYPE: PRT
<213> ORGANISM: Homo sapiens
<220> FEATURE:
<221> NAME/KEY: unsure
```

<222> LOCATION: 33-34
<223> OTHER INFORMATION: unknown amino acid

<400> SEQUENCE: 7

```
Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Val Asp
                 20                  25                  30

Ile Ser Xaa Xaa Ser Tyr Leu Asn Trp Tyr Gln Gln Lys Pro Gly
                 35                  40                  45

Lys Ala Pro Lys Leu Leu Ile Tyr Ala Ala Ser Ser Leu Glu Ser
                 50                  55                  60

Gly Val Pro Ser Arg Phe Ser Gly Ser Gly Ser Gly Thr Asp Phe
                 65                  70                  75

Thr Leu Thr Ile Ser Ser Leu Gln Pro Glu Asp Phe Ala Thr Tyr
                 80                  85                  90

Tyr Cys Gln Gln Tyr Asn Ser Leu Pro Tyr Thr Phe Gly Gln Gly
                 95                 100                 105

Thr Lys Val Glu Ile Lys
                110
```

<210> SEQ ID NO 8
<211> LENGTH: 114
<212> TYPE: PRT
<213> ORGANISM: Artificial
<220> FEATURE:
<221> NAME/KEY: Artificial
<222> LOCATION: 1-114
<223> OTHER INFORMATION: Light chain sequence derived from MAE11

<400> SEQUENCE: 8

```
Asp Ile Gln Leu Thr Gln Ser Pro Ser Ser Leu Ser Ala Ser Val
  1               5                  10                  15

Gly Asp Arg Val Thr Ile Thr Cys Arg Ala Ser Lys Pro Val Asp
                 20                  25                  30

Gly Glu Gly Asp Ser Tyr Leu Asn Trp Tyr Gln Gln Lys Pro Gly
                 35                  40                  45

Lys Ala Pro Lys Leu Leu Ile Tyr Ala Ala Ser Tyr Leu Glu Ser
                 50                  55                  60

Gly Val Pro Ser Arg Phe Ser Gly Ser Gly Ser Gly Thr Asp Phe
                 65                  70                  75

Thr Leu Thr Ile Ser Ser Leu Gln Pro Glu Asp Phe Ala Thr Tyr
                 80                  85                  90

Tyr Cys Gln Gln Ser His Glu Asp Pro Tyr Thr Phe Gly Gln Gly
                 95                 100                 105

Thr Lys Val Glu Ile Lys Arg Thr Val
                110
```

<210> SEQ ID NO 9
<211> LENGTH: 114
<212> TYPE: PRT
<213> ORGANISM: Artificial
<220> FEATURE:
<221> NAME/KEY: Artificial
<222> LOCATION: 1-114
<223> OTHER INFORMATION: Light chain sequence derived from MAE11

<400> SEQUENCE: 9

```
Asp Ile Gln Leu Thr Gln Ser Pro Ser Ser Leu Ser Ala Ser Val
  1               5                  10                  15
```

```
Gly Asp Arg Val Thr Ile Thr Cys Arg Ala Ser Gln Ser Val Asp
                20                  25                  30

Tyr Glu Gly Asp Ser Tyr Leu Asn Trp Tyr Gln Gln Lys Pro Gly
                35                  40                  45

Lys Ala Pro Lys Leu Leu Ile Tyr Ala Ala Ser Tyr Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser His Glu Asp Pro Tyr Thr Phe Gly Gln Gly
                95                 100                 105

Thr Lys Val Glu Ile Lys Arg Thr Val
               110


<210> SEQ ID NO 10
<211> LENGTH: 114
<212> TYPE: PRT
<213> ORGANISM: Artificial
<220> FEATURE:
<221> NAME/KEY: Artificial
<222> LOCATION: 1-114
<223> OTHER INFORMATION: Light chain sequence derived from MAE11

<400> SEQUENCE: 10

Asp Ile Gln Leu Thr Gln Ser Pro Ser Ser Leu Ser Ala Ser Val
  1               5                  10                  15

Gly Asp Arg Val Thr Ile Thr Cys Arg Ala Ser Gln Ser Val Asp
                20                  25                  30

Tyr Asp Gly Asp Ser Tyr Met Asn Trp Tyr Gln Gln Lys Pro Gly
                35                  40                  45

Lys Ala Pro Lys Leu Leu Ile Tyr Ala Ala Ser Tyr Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser His Glu Asp Pro Tyr Thr Phe Gly Gln Gly
                95                 100                 105

Thr Lys Val Glu Ile Lys Arg Thr Val
               110


<210> SEQ ID NO 11
<211> LENGTH: 114
<212> TYPE: PRT
<213> ORGANISM: Artificial
<220> FEATURE:
<221> NAME/KEY: Artificial
<222> LOCATION: 1-114
<223> OTHER INFORMATION: Heavy chain sequence derived from MAE11

<400> SEQUENCE: 11

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                20                  25                  30

Ser Gly Tyr Ser Trp Asn Trp Ile Arg Gln Ala Pro Gly Lys Gly
                35                  40                  45
```

```
Leu Glu Trp Val Ala Ser Ile Lys Tyr Ser Gly Glu Thr Lys Tyr
                50                  55                  60

Asn Pro Ser Val Lys Gly Arg Ile Thr Ile Ser Arg Asp Asp Ser
                65                  70                  75

Lys Asn Thr Phe Tyr Leu Gln Met Asn Ser Leu Arg Ala Glu Asp
                80                  85                  90

Thr Ala Val Tyr Tyr Cys Ala Arg Gly Ser His Tyr Phe Gly His
                95                 100                 105

Trp His Phe Ala Val Trp Gly Gln Gly
               110
```

<210> SEQ ID NO 12
<211> LENGTH: 114
<212> TYPE: PRT
<213> ORGANISM: Artificial
<220> FEATURE:
<221> NAME/KEY: Artificial
<222> LOCATION: 1-114
<223> OTHER INFORMATION: Heavy chain sequence derived from MAE11

<400> SEQUENCE: 12

```
Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                20                  25                  30

Ser Gly Tyr Ser Trp Asn Trp Ile Arg Gln Ala Pro Gly Lys Gly
                35                  40                  45

Leu Glu Trp Val Ala Ser Ile Thr Tyr Asp Gly Ser Thr Asn Tyr
                50                  55                  60

Asn Pro Ser Val Lys Gly Arg Ile Thr Ile Ser Arg Asp Asp Ser
                65                  70                  75

Lys Asn Thr Phe Tyr Leu Gln Met Asn Ser Leu Arg Ala Glu Asp
                80                  85                  90

Thr Ala Val Tyr Tyr Cys Ala Arg Gly Ser His Tyr Phe Gly His
                95                 100                 105

Trp His Phe Ala Val Trp Gly Gln Gly
               110
```

<210> SEQ ID NO 13
<211> LENGTH: 218
<212> TYPE: PRT
<213> ORGANISM: Artificial
<220> FEATURE:
<221> NAME/KEY: Artificial
<222> LOCATION: 1-218
<223> OTHER INFORMATION: Light chain sequence derived from MAE11

<400> SEQUENCE: 13

```
Asp Ile Gln Leu Thr Gln Ser Pro Ser Ser Leu Ser Ala Ser Val
  1               5                  10                  15

Gly Asp Arg Val Thr Ile Thr Cys Arg Ala Ser Gln Ser Val Asp
                20                  25                  30

Tyr Asp Gly Asp Ser Tyr Met Asn Trp Tyr Gln Gln Lys Pro Gly
                35                  40                  45

Lys Ala Pro Lys Leu Leu Ile Tyr Ala Ala Ser Tyr Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
```

```
                80                  85                  90

Tyr Cys Gln Gln Ser His Glu Asp Pro Tyr Thr Phe Gly Gln Gly
                95                  100                 105

Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215


<210> SEQ ID NO 14
<211> LENGTH: 451
<212> TYPE: PRT
<213> ORGANISM: Artificial
<220> FEATURE:
<221> NAME/KEY: Artificial
<222> LOCATION: 1-451
<223> OTHER INFORMATION: Heavy chain sequence derived from MAE11

<400> SEQUENCE: 14

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Thr Tyr Asp Gly Ser Thr Asn Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                  100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195
```

```
Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln
                305                 310                 315

Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly
                335                 340                 345

Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
                365                 370                 375

Phe Tyr Pro Ser Asp Ile Ala Val Glu Trp Glu Ser Asn Gly Gln
                380                 385                 390

Pro Glu Asn Asn Tyr Lys Thr Thr Pro Pro Val Leu Asp Ser Asp
                395                 400                 405

Gly Ser Phe Phe Leu Tyr Ser Lys Leu Thr Val Asp Lys Ser Arg
                410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
                440                 445                 450

Lys
```

<210> SEQ ID NO 15
<211> LENGTH: 218
<212> TYPE: PRT
<213> ORGANISM: Artificial
<220> FEATURE:
<221> NAME/KEY: Artificial
<222> LOCATION: 1-218
<223> OTHER INFORMATION: Light chain sequence derived from MAE11

<400> SEQUENCE: 15

```
Asp Ile Gln Leu Thr Gln Ser Pro Ser Ser Leu Ser Ala Ser Val
  1               5                  10                  15

Gly Asp Arg Val Thr Ile Thr Cys Arg Ala Ser Lys Pro Val Asp
                 20                  25                  30

Gly Glu Gly Asp Ser Tyr Leu Asn Trp Tyr Gln Gln Lys Pro Gly
                 35                  40                  45

Lys Ala Pro Lys Leu Leu Ile Tyr Ala Ala Ser Tyr Leu Glu Ser
                 50                  55                  60

Gly Val Pro Ser Arg Phe Ser Gly Ser Gly Ser Gly Thr Asp Phe
```

-continued

```
                65                  70                  75

Thr Leu Thr Ile Ser Ser Leu Gln Pro Glu Asp Phe Ala Thr Tyr
                80                  85                  90

Tyr Cys Gln Gln Ser His Glu Asp Pro Tyr Thr Phe Gly Gln Gly
                95                 100                 105

Thr Lys Val Glu Ile Lys Arg Thr Val Ala Ala Pro Ser Val Phe
               110                 115                 120

Ile Phe Pro Pro Ser Asp Glu Gln Leu Lys Ser Gly Thr Ala Ser
               125                 130                 135

Val Val Cys Leu Leu Asn Asn Phe Tyr Pro Arg Glu Ala Lys Val
               140                 145                 150

Gln Trp Lys Val Asp Asn Ala Leu Gln Ser Gly Asn Ser Gln Glu
               155                 160                 165

Ser Val Thr Glu Gln Asp Ser Lys Asp Ser Thr Tyr Ser Leu Ser
               170                 175                 180

Ser Thr Leu Thr Leu Ser Lys Ala Asp Tyr Glu Lys His Lys Val
               185                 190                 195

Tyr Ala Cys Glu Val Thr His Gln Gly Leu Ser Ser Pro Val Thr
               200                 205                 210

Lys Ser Phe Asn Arg Gly Glu Cys
               215


<210> SEQ ID NO 16
<211> LENGTH: 451
<212> TYPE: PRT
<213> ORGANISM: Artificial
<220> FEATURE:
<221> NAME/KEY: Artificial
<222> LOCATION: 1-451
<223> OTHER INFORMATION: Heavy chain sequence derived from MAE11

<400> SEQUENCE: 16

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                20                  25                  30

Ser Gly Tyr Ser Trp Asn Trp Ile Arg Gln Ala Pro Gly Lys Gly
                35                  40                  45

Leu Glu Trp Val Ala Ser Ile Thr Tyr Asp Gly Ser Thr Asn Tyr
                50                  55                  60

Asn Pro Ser Val Lys Gly Arg Ile Thr Ile Ser Arg Asp Asp Ser
                65                  70                  75

Lys Asn Thr Phe Tyr Leu Gln Met Asn Ser Leu Arg Ala Glu Asp
                80                  85                  90

Thr Ala Val Tyr Tyr Cys Ala Arg Gly Ser His Tyr Phe Gly His
                95                 100                 105

Trp His Phe Ala Val Trp Gly Gln Gly Thr Leu Val Thr Val Ser
               110                 115                 120

Ser Ala Ser Thr Lys Gly Pro Ser Val Phe Pro Leu Ala Pro Ser
               125                 130                 135

Ser Lys Ser Thr Ser Gly Gly Thr Ala Ala Leu Gly Cys Leu Val
               140                 145                 150

Lys Asp Tyr Phe Pro Glu Pro Val Thr Val Ser Trp Asn Ser Gly
               155                 160                 165

Ala Leu Thr Ser Gly Val His Thr Phe Pro Ala Val Leu Gln Ser
               170                 175                 180
```

```
Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln
                305                 310                 315

Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly
                335                 340                 345

Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
                365                 370                 375

Phe Tyr Pro Ser Asp Ile Ala Val Glu Trp Glu Ser Asn Gly Gln
                380                 385                 390

Pro Glu Asn Asn Tyr Lys Thr Thr Pro Pro Val Leu Asp Ser Asp
                395                 400                 405

Gly Ser Phe Phe Leu Tyr Ser Lys Leu Thr Val Asp Lys Ser Arg
                410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
                440                 445                 450

Lys


<210> SEQ ID NO 17
<211> LENGTH: 218
<212> TYPE: PRT
<213> ORGANISM: Artificial
<220> FEATURE:
<221> NAME/KEY: Artificial
<222> LOCATION: 1-218
<223> OTHER INFORMATION: Light chain sequence derived from MAE11

<400> SEQUENCE: 17

Asp Ile Gln Leu Thr Gln Ser Pro Ser Ser Leu Ser Ala Ser Val
  1               5                  10                  15

Gly Asp Arg Val Thr Ile Thr Cys Arg Ala Ser Lys Pro Val Asp
                 20                  25                  30

Gly Glu Gly Asp Ser Tyr Leu Asn Trp Tyr Gln Gln Lys Pro Gly
                 35                  40                  45

Lys Ala Pro Lys Leu Leu Ile Tyr Ala Ala Ser Tyr Leu Glu Ser
```

```
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser His Glu Asp Pro Tyr Thr Phe Gly Gln Gly
                95                 100                 105

Thr Lys Val Glu Ile Lys Arg Thr Val Ala Ala Pro Ser Val Phe
               110                 115                 120

Ile Phe Pro Pro Ser Asp Glu Gln Leu Lys Ser Gly Thr Ala Ser
               125                 130                 135

Val Val Cys Leu Leu Asn Asn Phe Tyr Pro Arg Glu Ala Lys Val
               140                 145                 150

Gln Trp Lys Val Asp Asn Ala Leu Gln Ser Gly Asn Ser Gln Glu
               155                 160                 165

Ser Val Thr Glu Gln Asp Ser Lys Asp Ser Thr Tyr Ser Leu Ser
               170                 175                 180

Ser Thr Leu Thr Leu Ser Lys Ala Asp Tyr Glu Lys His Lys Val
               185                 190                 195

Tyr Ala Cys Glu Val Thr His Gln Gly Leu Ser Ser Pro Val Thr
               200                 205                 210

Lys Ser Phe Asn Arg Gly Glu Cys
               215


<210> SEQ ID NO 18
<211> LENGTH: 451
<212> TYPE: PRT
<213> ORGANISM: Artificial
<220> FEATURE:
<221> NAME/KEY: Artificial
<222> LOCATION: 1-451
<223> OTHER INFORMATION: Heavy chain sequence derived from MAE11

<400> SEQUENCE: 18

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                20                  25                  30

Ser Gly Tyr Ser Trp Asn Trp Ile Arg Gln Ala Pro Gly Lys Gly
                35                  40                  45

Leu Glu Trp Val Ala Ser Ile Lys Tyr Ser Gly Glu Thr Lys Tyr
                50                  55                  60

Asn Pro Ser Val Lys Gly Arg Ile Thr Ile Ser Arg Asp Asp Ser
                65                  70                  75

Lys Asn Thr Phe Tyr Leu Gln Met Asn Ser Leu Arg Ala Glu Asp
                80                  85                  90

Thr Ala Val Tyr Tyr Cys Ala Arg Gly Ser His Tyr Phe Gly His
                95                 100                 105

Trp His Phe Ala Val Trp Gly Gln Gly Thr Leu Val Thr Val Ser
               110                 115                 120

Ser Ala Ser Thr Lys Gly Pro Ser Val Phe Pro Leu Ala Pro Ser
               125                 130                 135

Ser Lys Ser Thr Ser Gly Gly Thr Ala Ala Leu Gly Cys Leu Val
               140                 145                 150

Lys Asp Tyr Phe Pro Glu Pro Val Thr Val Ser Trp Asn Ser Gly
               155                 160                 165
```

```
Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys Pro Ala Pro Glu Leu Leu Gly
                230                 235                 240

Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln
                305                 310                 315

Asp Trp Leu Asn Gly Lys Glu Tyr Lys Cys Lys Val Ser Asn Lys
                320                 325                 330

Ala Leu Pro Ala Pro Ile Glu Lys Thr Ile Ser Lys Ala Lys Gly
                335                 340                 345

Gln Pro Arg Glu Pro Gln Val Tyr Thr Leu Pro Pro Ser Arg Glu
                350                 355                 360

Glu Met Thr Lys Asn Gln Val Ser Leu Thr Cys Leu Val Lys Gly
                365                 370                 375

Phe Tyr Pro Ser Asp Ile Ala Val Glu Trp Glu Ser Asn Gly Gln
                380                 385                 390

Pro Glu Asn Asn Tyr Lys Thr Thr Pro Pro Val Leu Asp Ser Asp
                395                 400                 405

Gly Ser Phe Phe Leu Tyr Ser Lys Leu Thr Val Asp Lys Ser Arg
                410                 415                 420

Trp Gln Gln Gly Asn Val Phe Ser Cys Ser Val Met His Glu Ala
                425                 430                 435

Leu His Asn His Tyr Thr Gln Lys Ser Leu Ser Leu Ser Pro Gly
                440                 445                 450

Lys


<210> SEQ ID NO 19
<211> LENGTH: 218
<212> TYPE: PRT
<213> ORGANISM: Artificial
<220> FEATURE:
<221> NAME/KEY: Artificial
<222> LOCATION: 1-218
<223> OTHER INFORMATION: Light chain F(ab) sequence derived from MAE11

<400> SEQUENCE: 19

Asp Ile Gln Leu Thr Gln Ser Pro Ser Ser Leu Ser Ala Ser Val
  1               5                  10                  15

Gly Asp Arg Val Thr Ile Thr Cys Arg Ala Ser Lys Pro Val Asp
                 20                  25                  30

Gly Glu Gly Asp Ser Tyr Leu Asn Trp Tyr Gln Gln Lys Pro Gly
```

```
                35                  40                  45

Lys Ala Pro Lys Leu Leu Ile Tyr Ala Ala Ser Tyr Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Tyr Cys Gln Gln Ser His Glu Asp Pro Tyr Thr Phe Gly Gln Gly
                95                  100                 105

Thr Lys Val Glu Ile Lys Arg Thr Val Ala Ala Pro Ser Val Phe
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215


<210> SEQ ID NO 20
<211> LENGTH: 229
<212> TYPE: PRT
<213> ORGANISM: Artificial
<220> FEATURE:
<221> NAME/KEY: Artificial
<222> LOCATION: 1-229
<223> OTHER INFORMATION: Heavy chain F(ab) sequence derived from MAE11

<400> SEQUENCE: 20

Glu Val Gln Leu Val Glu Ser Gly Gly Gly Leu Val Gln Pro Gly
  1             5                   10                  15

Gly Ser Leu Arg Leu Ser Cys Ala Val Ser Gly Tyr Ser Ile Thr
                20                  25                  30

Ser Gly Tyr Ser Trp Asn Trp Ile Arg Gln Ala Pro Gly Lys Gly
                35                  40                  45

Leu Glu Trp Val Ala Ser Ile Thr Tyr Asp Gly Ser Thr Asn Tyr
                50                  55                  60

Asn Pro Ser Val Lys Gly Arg Ile Thr Ile Ser Arg Asp Asp Ser
                65                  70                  75

Lys Asn Thr Phe Tyr Leu Gln Met Asn Ser Leu Arg Ala Glu Asp
                80                  85                  90

Thr Ala Val Tyr Tyr Cys Ala Arg Gly Ser His Tyr Phe Gly His
                95                  100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150
```

```
Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr


<210> SEQ ID NO 21
<211> LENGTH: 229
<212> TYPE: PRT
<213> ORGANISM: Artificial
<220> FEATURE:
<221> NAME/KEY: Artificial
<222> LOCATION: 1-229
<223> OTHER INFORMATION: Heavy chain F(ab) derived from MAE11

<400> SEQUENCE: 21

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Lys Tyr Ser Gly Glu Thr Lys Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr


<210> SEQ ID NO 22
```

<211> LENGTH: 248
<212> TYPE: PRT
<213> ORGANISM: Artificial
<220> FEATURE:
<221> NAME/KEY: Artificial
<222> LOCATION: 1-248
<223> OTHER INFORMATION: sFv sequence derived from MAE11

<400> SEQUENCE: 22

```
Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Thr Tyr Asp Gly Ser Thr Asn Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Glu Gly Gly Gly Ser Glu Gly Gly Gly Ser Glu Gly Gly Gly
                125                 130                 135

Ser Asp Ile Gln Leu Thr Gln Ser Pro Ser Ser Leu Ser Ala Ser
                140                 145                 150

Val Gly Asp Arg Val Thr Ile Thr Cys Arg Ala Ser Lys Pro Val
                155                 160                 165

Asp Gly Glu Gly Asp Ser Tyr Leu Asn Trp Tyr Gln Gln Lys Pro
                170                 175                 180

Gly Lys Ala Pro Lys Leu Leu Ile Tyr Ala Ala Ser Tyr Leu Glu
                185                 190                 195

Ser Gly Val Pro Ser Arg Phe Ser Gly Ser Gly Ser Gly Thr Asp
                200                 205                 210

Phe Thr Leu Thr Ile Ser Ser Leu Gln Pro Glu Asp Phe Ala Thr
                215                 220                 225

Tyr Tyr Cys Gln Gln Ser His Glu Asp Pro Tyr Thr Phe Gly Gln
                230                 235                 240

Gly Thr Lys Val Glu Ile Lys Arg
                245
```

<210> SEQ ID NO 23
<211> LENGTH: 248
<212> TYPE: PRT
<213> ORGANISM: Artificial
<220> FEATURE:
<221> NAME/KEY: Artificial
<222> LOCATION: 1-248
<223> OTHER INFORMATION: sFv sequence derived from MAE11

<400> SEQUENCE: 23

```
Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30
```

```
Ser Gly Tyr Ser Trp Asn Trp Ile Arg Gln Ala Pro Gly Lys Gly
                 35                  40                  45

Leu Glu Trp Val Ala Ser Ile Lys Tyr Ser Gly Glu Thr Lys Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Glu Gly Gly Gly Ser Glu Gly Gly Gly Ser Glu Gly Gly Gly
                125                 130                 135

Ser Asp Ile Gln Leu Thr Gln Ser Pro Ser Ser Leu Ser Ala Ser
                140                 145                 150

Val Gly Asp Arg Val Thr Ile Thr Cys Arg Ala Ser Lys Pro Val
                155                 160                 165

Asp Gly Glu Gly Asp Ser Tyr Leu Asn Trp Tyr Gln Gln Lys Pro
                170                 175                 180

Gly Lys Ala Pro Lys Leu Leu Ile Tyr Ala Ala Ser Tyr Leu Glu
                185                 190                 195

Ser Gly Val Pro Ser Arg Phe Ser Gly Ser Gly Ser Gly Thr Asp
                200                 205                 210

Phe Thr Leu Thr Ile Ser Ser Leu Gln Pro Glu Asp Phe Ala Thr
                215                 220                 225

Tyr Tyr Cys Gln Gln Ser His Glu Asp Pro Tyr Thr Phe Gly Gln
                230                 235                 240

Gly Thr Lys Val Glu Ile Lys Arg
                245


<210> SEQ ID NO 24
<211> LENGTH: 218
<212> TYPE: PRT
<213> ORGANISM: Artificial
<220> FEATURE:
<221> NAME/KEY: Artificial
<222> LOCATION: 1-218
<223> OTHER INFORMATION: Light chain F(ab)'2 sequence derived from MAE11

<400> SEQUENCE: 24

Asp Ile Gln Leu Thr Gln Ser Pro Ser Ser Leu Ser Ala Ser Val
  1               5                  10                  15

Gly Asp Arg Val Thr Ile Thr Cys Arg Ala Ser Lys Pro Val Asp
                 20                  25                  30

Gly Glu Gly Asp Ser Tyr Leu Asn Trp Tyr Gln Gln Lys Pro Gly
                 35                  40                  45

Lys Ala Pro Lys Leu Leu Ile Tyr Ala Ala Ser Tyr Leu Glu Ser
                 50                  55                  60

Gly Val Pro Ser Arg Phe Ser Gly Ser Gly Ser Gly Thr Asp Phe
                 65                  70                  75

Thr Leu Thr Ile Ser Ser Leu Gln Pro Glu Asp Phe Ala Thr Tyr
                 80                  85                  90

Tyr Cys Gln Gln Ser His Glu Asp Pro Tyr Thr Phe Gly Gln Gly
                 95                 100                 105

Thr Lys Val Glu Ile Lys Arg Thr Val Ala Ala Pro Ser Val Phe
```

-continued

```
                110                 115                 120

Ile Phe Pro Pro Ser Asp Glu Gln Leu Lys Ser Gly Thr Ala Ser
                125                 130                 135

Val Val Cys Leu Leu Asn Asn Phe Tyr Pro Arg Glu Ala Lys Val
                140                 145                 150

Gln Trp Lys Val Asp Asn Ala Leu Gln Ser Gly Asn Ser Gln Glu
                155                 160                 165

Ser Val Thr Glu Gln Asp Ser Lys Asp Ser Thr Tyr Ser Leu Ser
                170                 175                 180

Ser Thr Leu Thr Leu Ser Lys Ala Asp Tyr Glu Lys His Lys Val
                185                 190                 195

Tyr Ala Cys Glu Val Thr His Gln Gly Leu Ser Ser Pro Val Thr
                200                 205                 210

Lys Ser Phe Asn Arg Gly Glu Cys
                215


<210> SEQ ID NO 25
<211> LENGTH: 233
<212> TYPE: PRT
<213> ORGANISM: Artificial
<220> FEATURE:
<221> NAME/KEY: Artificial sequence
<222> LOCATION: 1-233
<223> OTHER INFORMATION: Heavy chain F(ab)'2 sequence derived from MAE11

<400> SEQUENCE: 25

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Thr Tyr Asp Gly Ser Thr Asn Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225
```

```
Lys Thr His Thr Cys Pro Pro Cys
                230


<210> SEQ ID NO 26
<211> LENGTH: 233
<212> TYPE: PRT
<213> ORGANISM: Artificial
<220> FEATURE:
<221> NAME/KEY: Artificial
<222> LOCATION: 1-233
<223> OTHER INFORMATION: Heavy chain F(ab)'2 sequence derived from MAE11

<400> SEQUENCE: 26

Glu Val Gln Leu Val Glu Ser Gly Gly Gly Leu Val Gln Pro Gly
  1               5                  10                  15

Gly Ser Leu Arg Leu Ser Cys Ala Val Ser Gly Tyr Ser Ile Thr
                 20                  25                  30

Ser Gly Tyr Ser Trp Asn Trp Ile Arg Gln Ala Pro Gly Lys Gly
                 35                  40                  45

Leu Glu Trp Val Ala Ser Ile Lys Tyr Ser Gly Glu Thr Lys Tyr
                 50                  55                  60

Asn Pro Ser Val Lys Gly Arg Ile Thr Ile Ser Arg Asp Asp Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Gly Ser His Tyr Phe Gly His
                 95                 100                 105

Trp His Phe Ala Val Trp Gly Gln Gly Thr Leu Val Thr Val Ser
                110                 115                 120

Ser Ala Ser Thr Lys Gly Pro Ser Val Phe Pro Leu Ala Pro Ser
                125                 130                 135

Ser Lys Ser Thr Ser Gly Gly Thr Ala Ala Leu Gly Cys Leu Val
                140                 145                 150

Lys Asp Tyr Phe Pro Glu Pro Val Thr Val Ser Trp Asn Ser Gly
                155                 160                 165

Ala Leu Thr Ser Gly Val His Thr Phe Pro Ala Val Leu Gln Ser
                170                 175                 180

Ser Gly Leu Tyr Ser Leu Ser Ser Val Val Thr Val Pro Ser Ser
                185                 190                 195

Ser Leu Gly Thr Gln Thr Tyr Ile Cys Asn Val Asn His Lys Pro
                200                 205                 210

Ser Asn Thr Lys Val Asp Lys Lys Val Glu Pro Lys Ser Cys Asp
                215                 220                 225

Lys Thr His Thr Cys Pro Pro Cys
                230


<210> SEQ ID NO 27
<211> LENGTH: 45
<212> TYPE: DNA
<213> ORGANISM: Artificial
<220> FEATURE:
<221> NAME/KEY: Artificial
<222> LOCATION: 1-45
<223> OTHER INFORMATION: Stop-Template Oligos for First-Round
      Mutagenesis

<400> SEQUENCE: 27

acctgccgtg ccagttaata agtctaataa gaaggtgata gctac                  45
```

```
<210> SEQ ID NO 28
<211> LENGTH: 46
<212> TYPE: DNA
<213> ORGANISM: Artificial
<220> FEATURE:
<221> NAME/KEY: Artificial
<222> LOCATION: 1-46
<223> OTHER INFORMATION: Stop-Template Oligos For First-Round
      Mutagenesis

<400> SEQUENCE: 28

gccagtcaga gcgtctaata ataaggttga agctacctga actggt                46


<210> SEQ ID NO 29
<211> LENGTH: 50
<212> TYPE: DNA
<213> ORGANISM: Artificial
<220> FEATURE:
<221> NAME/KEY: Artificial
<222> LOCATION: 1-50
<223> OTHER INFORMATION: Stop-Template Oligos For First-Round
      Mutagenesis

<400> SEQUENCE: 29

tgtgctcgag gcagctaata ataaggttaa tggtaattcg ccgtgtgggg            50


<210> SEQ ID NO 30
<211> LENGTH: 43
<212> TYPE: DNA
<213> ORGANISM: Artificial
<220> FEATURE:
<221> NAME/KEY: Artificial
<222> LOCATION: 1-43
<223> OTHER INFORMATION: Stop-Template Oligos For First-Round
      Mutagenesis

<400> SEQUENCE: 30

gaaactactg atttactaat aataataact ggagtctgga gtc                   43


<210> SEQ ID NO 31
<211> LENGTH: 53
<212> TYPE: DNA
<213> ORGANISM: Artificial
<220> FEATURE:
<221> NAME/KEY: Artificial
<222> LOCATION: 1-53
<223> OTHER INFORMATION: Stop-Template Oligos For First-Round
      Mutagenesis

<400> SEQUENCE: 31

cttattactg tcagcaaagt taataataac cgtaaacatt tggacagggt            50

acc                                                               53


<210> SEQ ID NO 32
<211> LENGTH: 46
<212> TYPE: DNA
<213> ORGANISM: Artificial
<220> FEATURE:
<221> NAME/KEY: Artificial
<222> LOCATION: 1-46
<223> OTHER INFORMATION: Stop-Template Oligos For First-Round
      Mutagenesis

<400> SEQUENCE: 32

gtcctgtgca gtttcttaat aataataata atccggatac agctgg                46


<210> SEQ ID NO 33
```

<211> LENGTH: 45
<212> TYPE: DNA
<213> ORGANISM: Artificial
<220> FEATURE:
<221> NAME/KEY: Artificial
<222> LOCATION: 1-45
<223> OTHER INFORMATION: Stop-Template Oligos For First-Round Mutagenesis

<400> SEQUENCE: 33
gcctactcca tcacctaata ataaagctga aactggatcc gtcag 45

<210> SEQ ID NO 34
<211> LENGTH: 53
<212> TYPE: DNA
<213> ORGANISM: Artificial
<220> FEATURE:
<221> NAME/KEY: Artificial
<222> LOCATION: 1-53
<223> OTHER INFORMATION: Stop-Template Oligos For First-Round Mutagenesis

<400> SEQUENCE: 34
gggttgcatc gatttaataa taaggataaa cttaatataa ccctagcctc 50
aag 53

<210> SEQ ID NO 35
<211> LENGTH: 48
<212> TYPE: DNA
<213> ORGANISM: Artificial
<220> FEATURE:
<221> NAME/KEY: Artificial
<222> LOCATION: 1-48
<223> OTHER INFORMATION: Stop-Template Oligos For First-Round Mutagenesis

<400> SEQUENCE: 35
aagccggtcg acaggtaata agattaatac taaaactggt atcaacag 48

<210> SEQ ID NO 36
<211> LENGTH: 45
<212> TYPE: DNA
<213> ORGANISM: Artificial
<220> FEATURE:
<221> NAME/KEY: Artificial
<222> LOCATION: 1-45
<223> OTHER INFORMATION: Library-Specific, Degenerate Oligos For Second Round Mutagenesis
<220> FEATURE:
<221> NAME/KEY: unsure
<222> LOCATION: 16-17, 19-20, 25-26, 28-29
<223> OTHER INFORMATION: unknown base

<400> SEQUENCE: 36
acctgccgtg ccagtnnsnn sgtcnnsnns gaaggtgata gctac 45

<210> SEQ ID NO 37
<211> LENGTH: 45
<212> TYPE: DNA
<213> ORGANISM: Artificial
<220> FEATURE:
<221> NAME/KEY: Artificial
<222> LOCATION: 1-45
<223> OTHER INFORMATION: Library-Specific, Degenerate Oligos For Second Round Mutagenesis
<220> FEATURE:
<221> NAME/KEY: unsure
<222> LOCATION: 16-17, 19-20, 22, 28-29
<223> OTHER INFORMATION: unknown base

<400> SEQUENCE: 37
gccagtcaga gcgtcnnsnn snssggtnns agctacctga actgg 45

<210> SEQ ID NO 38
<211> LENGTH: 50
<212> TYPE: DNA
<213> ORGANISM: Artificial
<220> FEATURE:
<221> NAME/KEY: Artificial
<222> LOCATION: 1-50
<223> OTHER INFORMATION: Library-Specific, Degenerate Oligos For Second Round Mutagenesis
<220> FEATURE:
<221> NAME/KEY: unsure
<222> LOCATION: 16-17, 19-20, 22-23, 28-29, 34-35
<223> OTHER INFORMATION: unknown base

<400> SEQUENCE: 38
tgtgctcgag gcagcnnsnn snnsggtnns tggnnsttcg ccgtgtgggg 50

<210> SEQ ID NO 39
<211> LENGTH: 43
<212> TYPE: DNA
<213> ORGANISM: Artificial
<220> FEATURE:
<221> NAME/KEY: Artificial
<222> LOCATION: 1-43
<223> OTHER INFORMATION: Library-Specific, Degenerate Oligos For Second Round Mutagenesis
<220> FEATURE:
<221> NAME/KEY: unsure
<222> LOCATION: 17-18, 20-21, 23-24, 26-27
<223> OTHER INFORMATION: unknown base

<400> SEQUENCE: 39
gaaactactg atttacnnsn nsnnsnnsct ggagtctgga gtc 43

<210> SEQ ID NO 40
<211> LENGTH: 53
<212> TYPE: DNA
<213> ORGANISM: Artificial
<220> FEATURE:
<221> NAME/KEY: Artificial
<222> LOCATION: 1-53
<223> OTHER INFORMATION: Library-Specific, Degenerate Oligos For Second Round Mutagenesis
<220> FEATURE:
<221> NAME/KEY: unsure
<222> LOCATION: 21-22, 24-25, 27-28, 33-34
<223> OTHER INFORMATION: unknown base

<400> SEQUENCE: 40
cttattactg tcagcaaagt nnsnnsnnsc cgnnsacatt tggacagggt 50
acc 53

<210> SEQ ID NO 41
<211> LENGTH: 46
<212> TYPE: DNA
<213> ORGANISM: Artificial
<220> FEATURE:
<221> NAME/KEY: Artificial
<222> LOCATION: 1-46
<223> OTHER INFORMATION: Library-Specific, Degenerate Oligos For Second Round Mutagenesis
<220> FEATURE:
<221> NAME/KEY: unsure
<222> LOCATION: 17-18, 20-21, 23-24, 26-27, 29-30
<223> OTHER INFORMATION: unknown base

<400> SEQUENCE: 41

-continued

```
gtcctgtgca gtttctnnsn nsnnsnnsnn stccggatac agctgg                46


<210> SEQ ID NO 42
<211> LENGTH: 51
<212> TYPE: DNA
<213> ORGANISM: Artificial
<220> FEATURE:
<221> NAME/KEY: Artificial
<222> LOCATION: 1-51
<223> OTHER INFORMATION: Library-Specific, Degenerate Oligos For Second
      Round Mutagenesis
<220> FEATURE:
<221> NAME/KEY: unsure
<222> LOCATION: 22-23, 25-26, 28-29, 34-35
<223> OTHER INFORMATION: unknown base

<400> SEQUENCE: 42

gtttctggct actccatcac cnnsnnsnns agcnnsaact ggatccgtca            50

g                                                                  51


<210> SEQ ID NO 43
<211> LENGTH: 53
<212> TYPE: DNA
<213> ORGANISM: Artificial
<220> FEATURE:
<221> NAME/KEY: Artificial
<222> LOCATION: 1-53
<223> OTHER INFORMATION: Library-Specific, Degenerate Oligos For Second
      Round Mutagenesis
<220> FEATURE:
<221> NAME/KEY: unsure
<222> LOCATION: 15-16, 18-19, 21-22, 27-28, 33-34
<223> OTHER INFORMATION: unknown base

<400> SEQUENCE: 43

gggttgcatc gattnnsnns nnsggannsa ctnnstataa ccctagcgtc            50

aag                                                                53


<210> SEQ ID NO 44
<211> LENGTH: 48
<212> TYPE: DNA
<213> ORGANISM: Artificial
<220> FEATURE:
<221> NAME/KEY: Artificial
<222> LOCATION: 1-48
<223> OTHER INFORMATION: Library-Specific, Degenerate Oligos For Second
      Round Mutagenesis
<220> FEATURE:
<221> NAME/KEY: unsure
<222> LOCATION: 16-17, 19-20, 25-26, 31-32
<223> OTHER INFORMATION: unknown base

<400> SEQUENCE: 44

aagccggtcg acaggnnsnn sgatnnstac nnsaactggt atcaacag              48
```

METHOD FOR TREATING IGE-MEDIATED DISORDERS

CROSS-REFERENCE TO RELATED APPLICATIONS

This is a continuation of U.S. Ser. No. 09/716,028, filed Nov. 17, 2000, now U.S. Pat. No. 6,723,833, which is a division of U.S. Ser. No. 09/109,207, filed Jun. 30, 1998, now U.S. Pat. No. 6,172,213, which is a non-provisional application filed under 37 CFR 1.53(b), claiming priority under 35 USC Section 119(e) to Provisional Application Ser. No. 60/051,554 filed Jul. 2, 1997, all of which are herein incorporated by reference.

BACKGROUND OF THE INVENTION

The present invention relates to immunoglobulin E (IgE), IgE antagonists, anti-IgE antibodies capable of binding to human IgE, and to a method of improving polypeptides, including anti-IgE antibodies.

IgE is a member of the immunoglobulin family that mediates allergic responses such as asthma, food allergies, type 1 hypersensitivity and the familiar sinus inflammation suffered on a widespread basis. IgE is secreted by, and expressed on the surface of B-cells or B-lymphocytes. IgE binds to B-cells (as well as to monocytes, eosinophils and platelets) through its Fc region to a low affinity IgE receptor, known as FcϵRII. Upon exposure of a mammal to an allergen, B-cells bearing a surface-bound IgE antibody specific for the antigen are "activated" and developed into IgE-secreting plasma cells. The resulting allergen-specific IgE then circulates through the bloodstream and becomes bound to the surface of mast cells in tissues and basophils in the blood, through the high affinity receptor also known as FcϵRI. The mast cells and basophils thereby become sensitized for the allergen. Subsequent exposure to the allergen causes a cross linking of the basophilic and mast cellular FcϵRI which results in a release of histamine, leukotrienes and platelet activating factors, eosinophil and neutrophil chemotactic factors and the cytokines IL-3, IL-4, IL-5 and GM-CSF which are responsible for clinical hypersensitivity and anaphylaxis.

The pathological condition hypersensitivity is characterized by an excessive immune response to (an) allergen(s) resulting in gross tissue changes if the allergen is present in relatively large amounts or if the humoral and cellular immune state is at a heightened level.

Physiological changes in anaphylactic hypersensitivity can include intense constriction of the bronchioles and bronchi of the lungs, contraction of smooth muscle and dilation of capillaries. Predisposition to this condition, however, appears to result from an interaction between genetic and environmental factors. Common environmental allergens which induce anaphylactic hypersensitivity are found in pollen, foods, house dust mites, animal danders, fungal spores and insect venoms. Atopic allergy is associated with anaphylactic hypersensitivity and includes the disorders, e.g., asthma, allergic rhinitis and conjunctivitis (hay fever), eczema, urticaria and food allergies. However anaphylactic shock, a dangerous life-threatening condition anaphylaxis is usually provoked by insect stings or parental medication.

Recently, a treatment strategy has been pursued for Type 1 hypersensitivity or anaphylactic hypersensitivity which attempts to block IgE from binding to the high-affinity receptor (FcϵRI) found on basophils and mast cells, and thereby prevent the release of histamine and other anaphylactic factors resulting in the pathological condition.

WO 93/04173, published 4 Mar. 1993 describes human IgE/IgG1 chimeras wherein IgG1 residues are substituted for the analogous IgE residues. Applicants' copending application U.S. Ser. No. 08/405,617 describes humanized anti-IgE antibodies wherein a murine antibody directed against human IgE (MaE11) was used to provide the CDR regions which were substituted into an IgG1 immunoglobulin framework (rhuMaE25). A technique of humanization is described in Reichman, L. et al., (1988) *Nature* 332: 323 and in Jones, P. T. et al. (1986), *Nature* 321: 522.

While humanization of murine antibodies has been established to provide anti-IgE molecules which provide similar affinity to IgE as murine MaE11 without the immunogenic response elicited by the latter (Shields et al., (1995) *Int. Arch. Allergy Immunol.* 107: 308–312), it has still not resulted in the construction of an anti-IgE with affinity for IgE which is decidedly better than MaE11 or a murine anti-IgE.

Recombinant monoclonal antibodies are subject to degradation reactions that affect all polypeptides or proteins, such as isomerization of aspartic acid and asparagine residues. As shown in FIG. A, below, aspartate residues (I) in -Asp-Gly- sequences can isomerize to isoaspartate (III) through a cyclic imide intermediate (II). (Geiger & Clarke, *J. Biol. Chem.* 262: 785–794 (1987)). The carboxylic acid side chain of the aspartic acid (I) reacts with the amide nitrogen of the adjacent glycine to form a cyclic aspartic acid intermediate (II) which then forms into an -isoaspartic acid-glycine- residue(III). The equilibrium, rate, and pH dependence of this reaction have been studied in model peptides separated by reversed phase high performance liquid chromatography. (Oliyai & Borchardt, *Pharm Res.* 10, 95–102 (1993)). The tendency to undergo isomerization is believed to also depend upon the local flexibility of the portion of the molecule containing the -Asp-Gly- sequence (Geiger & Clarke, supra).

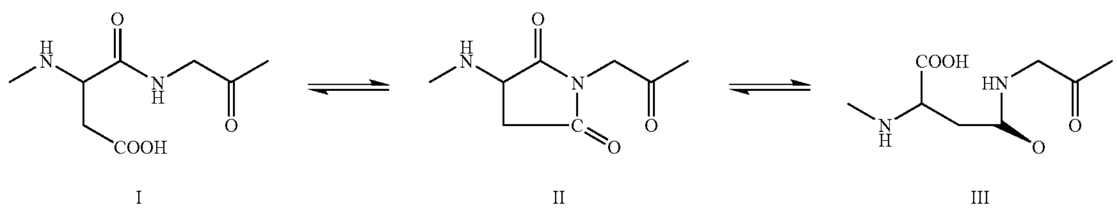

An example of a known antibody which undergoes aspartic acid isomerization is the potent anti-IgE antibody known as rhuMabE-25 (E-25). This event may occur spontaneously, but can be induced to occur when E-25 is incubated at 37° C. for 21 days. The end result is the insertion of an additional methyl group into the polypeptide backbone of the antibody, which can result in conformational changes and reduction in binding affinity. A study of E-25 with -c-Asp-Gly- and -iso-Asp-Gly- variants at position VL 32–33 indicated that while the isomerization event can be minimized by substitution of alanine or glutamic acid for residue VL32, the substitution itself results in a three-fold reduction in binding. Cacia et al., supra.

Thus, there exists a great need for the creation of improved polypeptides, including antibodies, which not only don't exhibit the "deactivating" event of aspartyl isomerization, but also display affinity to the target molecule (e.g., antigen) equal to or greater than the unimproved polypeptide's affinity.

SUMMARY

The present invention relates to a method for improving a polypeptide having affinity to a target molecule by a combination of steps, including: (1) the identification of aspartyl residues which are prone to isomerization; (2) the substitution of alternative residues and screening the resulting mutants for affinity against the target molecule. In a preferred embodiment, the method of substituting residues is affinity maturation with phage display (AMPD). In a further preferred embodiment the polypeptide is an antibody and the target molecule is an antigen. In a further preferred embodiment, the antibody is anti-IgE and the target molecule is IgE.

In an even more preferred embodiment, the invention relates to a method for improving the affinity of the anti-IgE antibody E-25 by replacement of VL CDR-L1 residue 32Asp with Glu, along with the modification of VL CDR-L1 residues 27Gln, 28 Ser and 31Tyr to Lys, Pro and Gly, respectively. In an even more preferred embodiment, the E-25 anti-IgE antibody has additional modifications at residues VH CDR2: 53Thr to Lys, 55Asp to Ser, 57Ser to Glu and 59Asn to Lys.

In another embodiment, the invention relates to an anti-IgE antibody having improved affinity to IgE.

In a preferred embodiment, the anti-IgE antibody comprises heavy and light chain residues comprising the sequence fragments labeled "e27" and "e26" in FIG. 2. Alternatively, the anti-IgE antibody comprises the full length heavy and light chain sequences labeled "E27" and "E26" in FIG. 12.

The present invention also relates to a composition of improved affinity anti-IgE or functional fragments thereof having pharmaceutical utility. The present invention also relates to an article of manufacture comprising an improved affinity anti-IgE antibody.

In yet another embodiment, the present invention relates to a method of reducing or inhibiting the IgE-mediated production of histamine.

In yet another embodiment, the present invention also relates to a method of treating and IgE-mediated disorder by the administration of the antibodies of the invention or functional fragments thereof.

Other aspects of the invention will become apparent from the following detailed description and the claims.

BRIEF DESCRIPTION OF THE DRAWINGS

FIG. 1 is a comparison of the VH and VL domains between the murine antibody MAE11, human consensus sequences of heavy chain subgroup III (humIII) and light chain κ subgroup I (humκI) and fragment F(ab)-2, a modified human antibody fragment with CDR residues and certain framework residues modified to murine.

FIG. 2 is a sequence comparison of the differences between the light chain and heavy chain CDR domains between rhuMabe25, e426, and sequences e26 and e27. The residue numbering here is consecutive, as opposed to that of Kabat et al. Also note that these sequences are only fragments and not the actual full-length heavy and light chain residues.

FIG. 3 is a graph of an FACS-based assay indicating the ability of the tested antibody to inhibit FITC-conjugated IgE binding to the α-chain of the high-affinity FcεRI receptor expressed on CHO 3D10 cells. The percentage of inhibition by murine mAb MaE11 (□), the negative control humanized mAb4D5 (■), F(ab)-2 (O), F(ab)-9 (●), F(ab)-11 (Δ) and F(ab)-12 (▲) are represented. The data points are the average of three experiments, except for mAb 4D5, which is a single experimental value. The results indicate that MaE11 and the tested F(ab)s block FITC-IgE binding to CHO 3D10 cells expressing FcεRI α-chain.

FIG. 4 is a graph of an FACS-based assay measuring the binding of the tested antibody to IgE-loaded with the α-subunit of the high-affinity receptor FcεRI expressed on CHO 3D10 cells. The percentage binding by murine mAb MaE11 (O), humanized variant 12 (▲), positive control murine mAb MaE1 (●), negative control antibody murine MOPC2 (Δ), and negative control humanized mAb4D5 (□). On an arithmetic/linear scale, mean channel fluorescence values at 0.1 μg/ml were MPOC21 7.3, MaE1 32.1, MaE11 6.4, hu4D5 4.7 and huMaE11 4.6. All three murine mAbs were murine isotype IgG1, and both humanized mAbs were human isotype IgG1. Data points are the average of three experiments. The results indicate that MaE11 and F(ab)-12 do not bind to IgE-loaded CHO 3D10 cells expressing FcεRI α-chain.

FIG. 5 is a graph of the molar ratio of anti-IgE v. percent inhibition of ragweed-induced histamine release. E-25 (●) and e-26 (O) are shown. The results indicate that the F(ab) form of e26 has superior inhibition of ragweed-induced histamine release in a dose dependent manner with a half-maximal inhibition molar ratio of 44:1 (anti-igE:RSIgE).

FIG. 6 is a graphical representation of the affinity enrichment after various rounds of affinity selections described in part II of Example 4. The ratio of binding enrichment for each pool to that of the wild-type (Emut/Ewt) is displayed. The results indicate that the VL libraries (represented by "a" & "b") displayed successively improved relative enrichments, up to about 10-fold greater than wild-type after 5–6 rounds of enrichment. Moreover, the VH libraries "c" and "d" exhibited about a 3-fold improvement after around 3 rounds. Note that "a" corresponds to the Fab-phage library mutated at VL CDR-1 residues 27, 28, 30 and 31, while "b" corresponds to mutations at 30, 31, 32 & 34, while "c" and "d" are independent F(ab) libraries with mutations at residues 101, 102, 103, 105 & 107.

FIG. 7 is a graph of the observed optical density vs. concentration of IgE competitor antibody in a phage ELISA competition study of the final variants from combinations of the VL CDR1 mutations in e26 with the VH CDR2 mutations in clones 235-5.1, 235-5.2, 235-5.3 and 235-5.4, renamed e27, e695, e696 and e697, respectively, described in part V of Example 4.

FIG. 8 is a graph of the absorbance at 490 nm of various concentration levels of e25, e26 and e27 anti-IgE antibody in the biotin plate assay described in part VI of Example 4.

FIGS. 9A–C indicates the F(ab) apparent binding affinity of e25, e26 and respectively, as measured by BIAcore TM-2000 surface plasmon resonance system. 1.5 serial dilutions of F(ab) antibody fragments were injected over the IgE chip in PBS/Tween buffer (0.05% Tween-20 in phosphate buffered saline) at 25° C. using a flow rate of 20 μl/min. The equilibrium dissociation constants (Kd) shown were calculated form the ratio of observed kon/koff for each Fab variant.

FIGS. 10A–F are a sequence listing of the plasmid p426 which was used as the template for the construction of library-specific stop templates in Example 4.

FIG. 11A is a diagram of plasmid pDH188 insert containing the DNA encoding the light chain and heavy chain (variable and constant domain 1) of the Fab humanized antibody directed to the HER-2 receptor. VL and VH are the variable regions for the light and heavy chains, respectively. $C_k$ is the constant region of the human kappa light chain. $CH1_{G1}$ is the first constant region of the human gamma 1 chain. Both coding regions start with the bacterial stII signal sequence.

FIG. 11B is a schematic diagram of the entire plasmid pDH188 containing the insert described in 11A. After transformation of the plasmid into *E. coli* SR101 cells and the addition of helper phage, the plasmid is packaged into phage particles. Some of these particles display the Fab-p III fusion (where p III is the protein encoded by the M13 gene III DNA).

FIG. 12 represents the full length heavy and light chain residues of anti-IgE antibodies E25, E26 and E27.

FIG. 13 represents F(ab) fragments of anti-IgE antibodies e26 and e27

FIG. 14 represents sFV fragments of anti-IgE antibodies e26 and e27.

FIG. 15 represents F(ab)'2 fragments of anti-IgE antibodies e26 and e27.

SEQ ID NO. 1 represents the sequence of the expression plasmid e426 used in the invention, also indicated in FIG. 10.

SEQ ID NO. 2 represents the variable heavy chain sequence of MaE11 indicated in FIG. 1

SEQ ID NO.3 represents the variable heavy chain sequence of F(ab)-2 indicated in FIG. 1.

SEQ ID NO. 4 represents the variable heavy chain sequence of humIII indicated in FIG. 1.

SEQ ID NO. 5 represents the variable light chain sequence of MaE11 indicated in FIG. 1.

SEQ ID NO. 6 represents the variable light chain sequence of F(ab)-2 indicated in FIG. 1.

SEQ ID NO. 7 represents the variable light chain sequence of humIII indicated in FIG. 1.

SEQ ID NO. 8 represents the variable light chain sequence of e26 and e27 indicated in FIG. 2.

SEQ ID NO. 9 represents the variable light chain sequence of e426 indicated in FIG. 2.

SEQ ID NO. 10 represents the variable light chain sequence of e25 indicated in FIG. 2.

SEQ ID NO. 11 represents the variably heavy chain sequence of e27 indicated in FIG. 2.

SEQ ID NO. 12 represents the variable heavy chain sequence of e25, e26 and e426 indicated in FIG. 2.

SEQ ID NO. 13 represents the full length variable light chain sequence of e25 as indicated in FIG. 12.

SEQ ID NO. 14 represents the full length heavy chain sequence of e25 as indicated in FIG. 12

SEQ ID NO 15 represents the full length light chain sequence of e26 as indicated in FIG. 12.

SEQ ID NO 16 represents the full length heavy chain sequence of e26 as indicated in FIG. 12.

SEQ ID NO 17 represents the full length light chain sequence of e27 as indicated in FIG. 12.

SEQ ID NO 18 represents the full length heavy chain sequence of e27 as indicated in FIG. 12.

SEQ ID NO 19 represents the variable light Fab fragment of e26 and e27 as indicated in FIG. 13.

SEQ ID NO 20 represents the variable heavy chain Fab fragment of e26 as indicated in FIG. 13.

SEQ ID NO 21 represents the variable heavy chain Fab fragment of e27 as indicated in FIG. 13.

SEQ ID NO 22 represents the sFv fragment of e26 as indicated in FIG. 14.

SEQ ID NO 23 represents the sFv fragment of e27 as indicated in FIG. 14.

SEQ ID NO 24 represents the variable light chain $F(ab)'_2$ fragment for e26 and e27 as indicated in FIG. 15.

SEQ ID NO 25 represents the variable heavy chain $F(ab)'_2$ fragment for e26 as indicated in FIG. 15.

SEQ ID NO 26 represents the variable heavy chain $F(ab)'_2$ fragment for e27 as indicated in FIG. 15.

DETAILED DESCRIPTION OF THE PREFERRED EMBODIMENTS

The mention of particular references, patent application and patents throughout this application should be read as being incorporated by reference into the text of the specification.

Definitions:

Terms used throughout this application are to be construed with ordinary and typical meaning to those of ordinary skill in the art. However, Applicants desire that the following terms be given the particular definition as defined below:

The terms "protein" or "polypeptide" are intended to be used interchangeably. They refer to a chain of two (2) or more amino acids which are linked together with peptide or amide bonds, regardless of post-translational modification (e.g., glycosylation or phosphorylation). Antibodies are specifically intended to be within the scope of this definition.

The polypeptides of this invention may comprise more than one subunit, where each subunit is encoded by a separate DNA sequence.

The phrase "substantially identical" with respect to an antibody polypeptide sequence shall be construed as an antibody exhibiting at least 70%, preferably 80%, more preferably 90% and most preferably 95% sequence identity to the reference polypeptide sequence. The term with respect to a nucleic acid sequence shall be construed as a sequence of nucleotides exhibiting at least about 85%, preferably 90%, more preferably 95% and most preferably 97% sequence identity to the reference nucleic acid sequence. For polypeptides, the length of the comparison sequences will generally be at least 25 amino acids. For nucleic acids, the length will generally be at least 75 nucleotides.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

The term "antibody" is used in the broadest sense, and specifically covers monoclonal antibodies (including full length monoclonal antibodies), polyclonal antibodies, multispecific antibodies (e.g., bispecific antibodies), and antibody fragments (e.g., Fab, $F(ab')_2$ and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 186, 651–66, 1985); Novotny and Haber, *Proc. Natl. Acad. Sci. USA* 82, 4592–4596 (1985).

An "isolated" antibody is one which has been identified and separated and/or recovered from a component of the environment in which it was produced. Contaminant components of its production environment are materials which would interfere with diagnostic or therapeutic uses for the antibody, and may include enzymes, hormones, and other proteinaceous or nonproteinaceous solutes. In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, isolated antibody will be prepared by at least one purification step.

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1\times10^{-7}$ M, preferably no more than about $1\times10^{-8}$ and most preferably no more than about $1\times10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

The term "antibody mutant" refers to an amino acid sequence variant of an antibody wherein one or more of the amino acid residues have been modified. Such mutants necessarily have less than 100% sequence identity or similarity with the amino acid sequence having at least 75% amino acid sequence identity or similarity with the amino acid sequence of either the heavy or light chain variable domain of the antibody, more preferably at least 80%, more preferably at least 85%, more preferably at least 90%, and most preferably at least 95%. Since the method of the invention applies equally to both polypeptides, antibodies and fragments thereof, these terms are sometimes employed interchangeably.

The term "variable" in the context of variable domain of antibodies, refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains. There are at least two techniques for determining CDRs: (1) an approach based on cross-species sequence variability (i.e., Kabat et al., Sequences of Proteins of Immunological Interest (National Institute of Health, Bethesda, Md. 1987); and (2) an approach based on crystallographic studies of antigen-antibody complexes (Chothia, C. et al. (1989), *Nature* 342: 877). With respect to Applicants' anti-IgE antibody, certain CDRs were defined by combining the Kabat et al. and Chothia et al. approaches. The more highly conserved portions of variable domains are called the framework (FR). The variable domains of native heavy and light chains each comprise four FR regions, largely adopting a n-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al.). The constant domains are not involved directly in binding an antibody to an antigen, but exhibit various effector function, such as participation of the antibody in antibody-dependent cellular toxicity.

The term "antibody fragment" refers to a portion of a full-length antibody, generally the antigen binding or variable region. Examples of antibody fragments include Fab, Fab', $F(ab')_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an $F(ab')_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and $F(ab')_2$ fragments.

An "Fv" fragment is the minimum antibody fragment which contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment [also designated as F(ab)] also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the $F(ab')_2$ pepsin digestion product. Additional chemical couplings of antibody fragments are known to those of ordinary skill in the art.

The light chains of antibodies (immunoglobulin) from any vertebrate species can be assigned to one of two clearly distinct types, called kappa (κ) and lambda (λ), based on the amino sequences of their constant domain.

Depending on the amino acid sequences of the constant domain of their heavy chains, "immunoglobulins" can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called α, δ, ϵ, γ and μ, respectively. The subunit structures and three-dimensional configurations of different classes of immunoglobulins are well known. The preferred immunoglobulin for use with the present invention is immunoglobulin E.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature* 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. *Nature* 352: 624–628 (1991), as well as in Marks et al., *J. Mol. Biol.* 222: 581–597 (1991).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. *Proc. Natl. Acad. Sci.* 81, 6851–6855 (1984).

"Humanized" forms of non-human (e.g. murine) antibodies are chimeric immunogbobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues, from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or subsiantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., *Nature* 321, 522–525 (1986); Reichmann et al., *Nature* 332 323–329 (1988) and Presta, *Curr. Op. Struct. Biol.* 2, 593–596 (1992).

"Single-chain Fv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269–315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more. fully in, for example, EP 404,097; WO 93/11161, and Hollinger et al., *Proc. Natl. Acad. Sci. USA* 90: 6444–6448 (1993).

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

The term "amino acid" and "amino acids" refer to all naturally L-α-amino acids. The amino acids are identified as hereinafter described under section A. Antibody Preparation: (iv) *Generation of mutant antibodies*. The term "amino acid variant" refers to molecules with some differences in their amino acid sequences as compared to a native amino acid sequence.

"Substitutional" variants are those that have at least one amino acid residue in a native sequence removed and a different amino acid inserted in its place at the same position. The substitutions may be single, where only one amino acid in the molecule as been substituted, or they may be multiple, where two or more amino acids have been substituted in the same molecule. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule.

The term "cell", "cell line" and "cell culture" are used interchangeably, and all such designations include progeny. It is also understood that all progeny may not be precisely identical in DNA content, due to deliberate or inadvertent mutations. Mutant progeny that have the same function or biological property, as screened for in the orginally transformed cell, are included.

The "host cells" used in the present invention generally are prokaryotic or eukaryotic hosts. Example of suitable host cells are described in Section B. Vectors, Host Cells and Recombinant Methods: (vii) Selection and transformation of host cells.

"Transformation" means introducing DNA into an organism so that the DNA is replicable, either as an extrachromosomal element or by chromosomal integration.

"Transfection" refers to the taking up of an expression vector by a host cell whether or not any coding sequences are in fact expressed.

The terms "transfected host cell" and "transformed" refer to the introduction of DNA into a cell. The cell is termed "host cell" and it may be either prokaryotic or eukaryotic. Typical prokaryotic host cells include various strains of *E. coli*. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA and several copies of the vector and its inserted (foreign) DNA may be generated.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector at present. However, the invention is intended to include such other form of vectors which serve equivalent function as and which are, or become, known in the art. Typical expression vectors for mammalian cell culture expression, for example, are based on pRK5 (EP 307,247), pSV16B (WO 91/08291) and pVL1392 (Pharmingen).

A "liposome" is a small vesicle composed of various types of lipids, phospholipids and/or surfactant which is useful for delivery of a drug (such as the antibody mutants disclosed herein and, optionally, a chemotherapeutic agent) to a mammal. The components of the liposome are commonly arranged in a bilayer formation, similar to the lipid arrangement of biological membranes.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguishable from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Nucleic acid is "operably linked" when it is placed into a functional relationship with another nucleic acid sequence. This can be a gene and a regulatory sequence(s) which are connected in such a way as to permit gene expression when the appropriate molecules (e.g., transcriptional activator proteins) are bound to the regulatory sequences(s). For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Treatment" refers to both therapeutic treatment and prophylactic or preventative measures. Those in need of treatment include those already with the disorder as well as those in which the disorder is to be prevented.

A "disorder" is any condition that would benefit from treatment with the polypeptide. This includes chronic and acute disorders or diseases including those pathological conditions which predispose the mammal to the disorder in question.

The term "immunosuppressive agent" as used herein for adjunct therapy refers to substances that act to suppress or mask the immune system of the host into which a graft is being transplanted. This would include substances that suppress cytokine production, downregulate or suppress self-antigen expression, or mask the MHC antigens. Examples of such agents include 2-amino-5-aryl-5-substituted pyrimidines (See U.S. Pat. No. 4,665,077), azathioprine (or cyclophosphamide, in case of adverse reaction to azathioprine); bromocryptine; glutaraldehyde (which masks the MHC antigens, as described in U.S. Pat. No. 4,120,649); anti-idiotypic antibodies for MHC antigens and NHC fragments; cyclosporin A; steroids such as glucocorticosteroids, e.g., prednisone, methylprednisone, and dexamethasone; cytokine or cytokine receptor antagonists including anti-interferon-γ, -β, or α-antibodies; anti-tumor necrosis factor-α antibodies; anti-tumor necrosis factor-β antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26 1990); streptokinase; TGF-62; streptodornase; RNA or DNA from the host; FK506; RS-61443; deoxyspergualin; rapamycin; T-cell receptor (U.S. Pat. No. 5,114,721); T-cell receptor fragments (Offner et al., *Science* 251: 430–432 (1991); WO 90/11294; and WO 91/01133); and T cell receptor antibodies (EP 340,109) such as T10B. These agents are administered at the same time or at separate times from CD11a antibody, and are used at the same or lesser dosages than as set forth in the art. The preferred adjunct immunosuppressive agent will depend on many factors, including the type of disorder being treated including the type of transplantation being performed, as well as the patient's history, but a general overall preference is that the agent be selected from cyclosporin A, a glucocorticosteroid (most preferably prednisone or methyiprednisolone), OKT-3 monoclonal antibody, azathioprine, bromocryptine, heterologous anti-lymphocyte globulin, or a mixture thereof.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

"Mammal" for purposes of treatment refers to any animal classified as a mammal, including human, domestic and farm animals, nonhuman primates, and zoo, sports, or pet animals, such as dogs, horses, cats, cows, etc.

The term "epitope tagged" when used herein refers to polypeptide fused to an "epitope tag." The epitope tag polypeptide has enough residues to provide an epitope against which an antibody thereagainst can be made, yet is short enough such that it does not interfere with activity of the polypeptide. The epitope tag preferably also is fairly unique so that the antibody thereagainst does not substantially cross-react with other epitopes. Suitable tag polypeptide generally have at least 6 amino acid residues and usually between about 8–50 amino acid residues (preferably between about 9–30 residues). Examples include the flu HA tag polypeptide and its antibody 12CA5 (Field et al., *Mol. Cell. Biol.* 8: 2159–2165 (1988)); the c-myc tag and the 8F9, 3C7, 6E10, G4, B7 and 9E10 antibodies thereagainst (Evan et al., *Mol. Cell. Biol.* 5(12): 3610–3616 (1985)); and the Herpes Simplex virus glycoprotein D (gD) tag and its antibody (Paborsky et al., *Protein Engineering* 3(6): 547–553 (1990)). In certain embodiments, the epitope tag is a "salvage receptor binding epitope."

As used herein, the term "salvage receptor binding epitope" refers to an epitope of the Fc region of an IgG molecule (e.g., $IgG_1$, $IgG_2$, $IgG_3$ or $IgG_4$) that is responsible for increasing the in vivo serum half-life of the IgG molecule.

The term "cytotoxic agent" as used herein refers to a substance that inhibits or prevent the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include Adrimycin, Doxorubicin, 5-Fluorouracil, Cytosine arabinoside("Ara-C"), Cyclophosphamide, thiotepa, Taxotere (docetaxel), Bulsulfan, Cytoxin, Taxol, Methotrexate, Cisplatin, Melphalan, Vinblastine, Bleomycin, Etoposide, Ifosfamide, Mitomycin C, Mitoxantrone, Vincristine, Vinorelbine, Carboplatin, Teniposide, Daunomycin, Carminomycin, Aminopterin, Dactinomycin, Mitomycine, Esperamicins (see U.S. Pat. No. 4,675,187), Melphalan and other related nitrogen mustards.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy," *Biochemical Society Transactions*, 14, pp. 375–382, 615 Meeting, Belfast (1986) and Stella et al., (ed.), "Prodrugs: A Chemical Approach to Targeted Drug Delivery," *Directed Drug Delivery*, Borchardt et al., (ed.), pp. 247–267, Human Press (1985). The prodrugs of this invention include, but are not limited to phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The word “label” when used herein refers to a detectable compound or composition which is conjugated directly or indirectly to the antibody. The label may itself be detectable (e.g., radioisotope labels or fluorescent labels) or, in the case of an enzymatic label, may catalyze chemical alteration of a substrate compound or composition which is detectable.

As used herein, “solid phase” means a non-aqueous matrix to which the antibody of the present invention can adhere. Example of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

As used herein, anti-human IgE antibody means an antibody which binds to human IgE in such a manner so as to inhibit or substantially reduce the binding of such IgE to the high affinity receptor, Fc$\epsilon$RI. Preferably this anti-IgE antibody is E-25.

As used herein, the term “IgE-mediated disorder” means a condition or disease which is characterized by the overproduction and/or hypersensitivity to the immunoglobulin IgE. Specifically it should be construed to include conditions associated with anaphylactic hypersensitivity and atopic allergies, including for example: asthma, allergic rhinitis & conjunctivitis (hay fever), eczema, urticaria and food allery. However, the serious physiological condition of anaphylactic shock, usually caused by bee or snake stings or parental medication is also encompassed under the scope of this term.

As used herein, “affinity maturation using phage display” (AMPD) refers to a process described in Lowman et al., *Biochemistry* 30(45): 10832–10838 (1991), see also Hawkins et al., *J. Mol Biol.* 254: 889–896 (1992). While not strictly limited to the following description, this process can be described briefly as: several hypervariable region sites (e.g. 6–7 sites) are mutated to generate all possible amino acid substitutions at each site. The antibody mutants thus generated are displayed in a monovalent fashion from filamentous phage particles as fusions to the gene III product of M13 packaged within each particle. The phage expressing the various mutants can be cycled through rounds of binding selection, followed by isolation and sequencing of those mutants which display high affinity. The method is also described in WO 92/09690, issued 11 Jun. 1992. A modified procedure involving pooled affinity display is described in Cunningham, B. C. et al., *EMBO J.* 13(11), 2508–2515 (1994).

The method provides a method for selecting novel binding polypeptides comprising: a) constructing a replicable expression vector comprising a first gene encoding a polypeptide, a second gene encoding at least a portion of a natural or wild-type phage coat protein wherein the first and second genes are heterologous, and a transcription regulatory element operably linked to the first and second genes, thereby forming a gene fusion encoding a fusion protein; b) mutating the vector at one or more selected positions within the first gene thereby forming a family of related plasmids; c) transforming suitable host cells with the plasmids; d) infecting the transformed host cells with a helper phage having a gene encoding the phage coat protein; e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; f) contacting the phagemid particles with a target molecule so that at least a portion of the phagemid particles bind to the target molecule; and g) separating the phagemid particles that bind from those that do not. Preferably, the method further comprises transforming suitable host cells with recombinant phagemid particles that bind to the target molecule and repeating steps d) through g) one or more times.

Alternatively, the method includes polypeptides which are composed of more than one subunit, wherein the replicable expression vector comprising a transcription regulatory element operably linked to DNA encoding the subunit of interest is fused to the phage coat protein.

As used herein, the term “antibody phage library” refers to the phage library used in the affinity maturation process described above and in Hawkins et al., *J. Mol Biol.* 254: 889–896 (1992), and in Lowman et al., *Biochemistry* 30(45): 10832–10838 (1991). Each library comprises a hypervariable region (e.g. 6–7 sites) for which all possible amino acid substitutions are generated. The antibody mutants thus generated are displayed in a monovalent fashion from filamentous phage particles as fusions to the gene III product of M13 packaged within each particle and expressed on the exterior of the phage.

As used herein, “room” or “ambient temperature” shall be 23° C.–25° C.

As used herein “binding polypeptide” means any polypeptide that binds with a selectable affinity to a target molecule. Preferably, the polypeptide will be a protein that most preferably contains more than about 100 amino acid residues. Typically, the polypeptide will be a hormone or an antibody or a fragment thereof.

As used herein, “high affinity” means an affinity constant (Kd) of $<10^{-5}$ M and preferably $<10^{-7}$ M under physiological conditions.

As used herein, “target molecule” means any molecule, not necessarily a protein, for which it is desirable to produce an antibody or ligand. Preferably, however, the target will be a protein and most preferably the target will be an antigen. However, receptors, such as a hormone receptors should particularly be included within the scope of this term.

As used herein, all numbering of immunoglobulin amino acid residues, including the amino acid numbering of peptides corresponding to specific portions of IgE, mutant IgE molecules and chimeric IgE molecules that appears herein is done according to the immunoglobulin amino acid residue numbering system of Kabat et al., Sequences of Proteins of Immunological Interest (National Institute of Health, Bethesda, Md. 1987).

MODES FOR CARRYING OUT THE INVENTION

I. Method of Improving Target Molecule Affinity

A. Identification of Isomerizable Aspartyl Residues

In practicing the present invention, the identification of isomerizable aspartyl residues prone to isomerization can be effected by any technique known to those of ordinary skill in the art. For example, Cacia et al., *Biochemistry* 35, 1897–1903 (1996), describe a process wherein the anti-IgE antibody E-25 (which contains -Asp-Gly- residues) is incubated at 37° C. for 21 days. The identification of isomerized -Asp-Gly- were effected by chromatographic and mass spectrometric analysis of untreated and protease treated fragments. Since isomerization has also been reported to occur with asparaginyl residues (T. Geiger and S. Clarke, *J. Biol. Chem*. 262(2), 785–794 (1987), the present invention may also be preferably practiced to the systematic evaluation and improvement of polypeptides containing asparaginyl residues.

B. Selection of Alternate Residues which Improve Target Molecule Affinity

Many techniques are available to one of ordinary skill in the art which permit the optimization of receptor affinity. Typically, these techniques all involve substitution of various amino acid residues at the site of interest, followed by a screening analysis of receptor affinity of the mutant polypeptide. A technique preferred for use with the present invention is affinity maturation using phage display (Hawkins et al. *J. Mol Biol*. 254: 889–896 (1992); Lowman et al., *Biochemistry* 30(45): 10832–10838 (1991)). Briefly, several hypervariable region sites (e.g. 6–7 sites) are mutated to generate all possible amino acid substitutions at each site. The antibody mutants thus generated are displayed in a monovalent fashion from filamentous phage particles as fusions to the gene III product of M13 packaged within each particle. The phage expressing the various mutants can be cycled through rounds of binding selection, followed by isolation and sequencing of those mutants which display high affinity.

The method of selecting novel binding polypeptides preferably utilizes a library of structurally related polypeptides. The library of structurally related polypeptides, fused to a phage coat protein, is produced by mutagenesis, and preferably, a single copy of each related polypeptide is displayed on the surface of the phagemid particle containing DNA encoding that polypeptide. These phagemid particles are then contacted with a target molecule and those particles having the highest affinity for the target are separated from those of lower affinity. The high affinity binders are then amplified by infection of a bacterial host and the competitive binding step is repeated. The process is repeated until polypeptides of the desired affinity are obtained.

Alternatively, multivalent phage (McCafferty et al. (1990), *Nature* 348, 552–554; Clackson et al. (1991), *Nature* 352, 624–628) can also be used to express random point mutations (generated by use of an error-prone DNA polymerase) to generate a library of phage antibody fragments which could then be screened by affinity to antigen. Hawkins et al., (1992) *J. Mol. Biol*. 254: 889–896.

Preferably during the affinity maturation process, the replicable expression vector is under tight control of the transcription regulatory element, and the culturing conditions are adjusted so that the amount or number of phagemid particles displaying more than one copy of the fusion protein on the surface of the particle is less than about 1%. Also preferably, the amount of phagemide particles displaying more than one copy of the fusion protein is less than 10% the amount of phagemid particles displaying a single copy of the fusion protein. Most preferably the amount is less than 20%.

Typically, in the method of this invention, the expression vector will further contain a secretory signal sequences fused to the DNA encoding each subunit of the polypeptide, and the transcription regulatory element will be a promoter system. Preferred promoter systems are selected from: LacZ, $\lambda_{PL}$, TC, T7 polymerase, tryptophan, and alkaline phosphatase promoters and combinations thereof.

Also typically, the first gene will encode a mammalian protein, preferably, the protein will be an anti-IgE antibody. Additional antibodies are exemplified in section II.A. Antibody preparation, (vi) multispecific antibodies (note however, that antibodies need not be multispecific). Additional polypeptides include human growth hormone (hGH), N-methionyl human growth hormone, bovine growth hormone, parathyroid hormone, thyroxine, insulin A-chain, insulin B-chain, proinsulin, relaxin A-chain, relaxin B-chain, prorelaxin, glycoprotein hormones such as follicle stimulating hormone (FSH), thyroid stimulating hormone (THS), and leutinizing hormone (LH), glycoprotein hormone receptors, calcitonin, glucagon, factor VIII, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, such as betalactamase, tissue factor protein, inhibin, activin, vascular endothelial growth factor, receptors for hormones or growth factors, integrin, thrombopoietin, protein A or D, rheumatoid factors, nerve growth factors such as NGF-β, platelet-growth factor, transforming growth factors (TGF) such as TGF-alpha and TGF-beta, insulin-like growth factor-I and -II, insulin-like growth factor binding proteins, CD-4, DNase, latency associated peptide, erythropoietin, osteoinductive factors, interferons such as interferon-alpha, -beta and -gamma, colony stimulating factors (CSFs) such as M-CSF, GM-CSF and G-CSF, interleukins (ILs) such as IL-1, IL-2, IL-3, IL-4, superoxide dismutase, decay accelerating factor, viral antigen, HIV envelope proteins such as GP120, GP140, atrial natriuretic peptides A, B or C, immunoglobulins, and fragments of any of the above-listed proteins.

Preferably, the first gene will encode a polypeptide of one or more subunits containing more than about 100 amino acid residues and will be folded to form a plurality of rigid secondary structures displaying a plurality of amino acids capable of interacting with the target. Preferably the first gene will be mutated at codons corresponding to only the amino acids capable of interacting with the target so that the integrity of the rigid secondary structures will be preserved.

Normally, the method of this invention will employ a helper phage selected from: M13KO7, M13R408, M13-VCS, and Phi X 174. The preferred helper phage is M13KO7, and the preferred coat protein is the M13 Phage gene II coat protein. The preferred host is *E. coli*, and protease deficient strains of *E. coli*. Novel hGH variants selected by the method of the present invention have been detected. Phagemid expression vectors were constructed that contain a suppressible termination codon functionally located between the nucleic acids encoding the polypeptide and the phage coat protein.

1. Choice of Polypeptides for Display on the Surface of a Phage

Repeated cycles of "polypeptide" selection are used to select for higher and higher affinity binding by the phagemid selection of multiple amino acid changes which are selected by multiple selection of cycles. Following a first round of phagemid selection, involving a first region of selection of amino acids in the ligand or antibody polypeptide, additional rounds of phagemid selection in other regions or amino acids of the ligand are conducted. The cycles of phagemid selection are repeated until the desired affinity properties are achieved. To illustrate this process, Example 4 phage display was conducted in cycles. Pooled affinity, combination of mutations from different CDRs, etc.

From the foregoing, it will be appreciated that the amino acid residues that form the binding domain of the polypeptide will not be sequentially linked and may reside on different subunits of the polypeptide. That is, the binding domain tracks with particular secondary structure at the binding site and not the primary structure. Thus, generally, mutations will be introduced into codons encoding amino acids within a particular secondary structure at sites directed away from the interior of the polypeptide so that they will have the potential to interact with the target.

However, there is no requirement that the polypeptide chosen as a ligand or antibody to a target molecule normally bind to that target. Thus, for example, a glycoprotein hormone such as TSH can be chosen as a ligand for the FSH receptor and a library of mutant TSH molecules are employed in the method of this invention to produce novel drug candidates.

This invention thus contemplates any polypeptide that binds to a target molecule, particularly antibodies. Preferred polypeptides are those that have pharmaceutical utility. Example antibodies are recited in section II. A. Antibody preparation (iv) multispecific antibodies (Note that antibodies need not be multispecific). More preferred polypeptides include: growth hormone, including human growth hormone, des-N-methionyl human growth hormone, and bovine growth hormone; parathyroid hormone; thyroid stimulating hormone; thyroxine; insulin A-chain; insulin B-chain; prorelaxin; mouse gonadotropin-associated peptide; a microbial protein, such as betalactamase; tissue factor protein; inhibin; activin; vascular endothelial growth factor; receptors for hormones or growth factors; integrin; thrombopoietin; protein A or D; rheumatoid factors; nerve growth factor such NGF-β; platelet-derived growth factor; fibroblast growth factor such as aFGF and bFGF, epidermal growth factor; transforming growth factor (TGF) such as TGF-alpha and TGF-beta; insulin-like growth factor-I and -II; insulin-like growth factor binding proteins; CD-4; DNase; latency associated peptide; erythropoietin; osteoinductive factors; such as, for example, a portion of the HIV envelope; immunoglobulins; and fragments of any of the above-listed polypeptides. In addition, one or more predetermined amino acid residues on the polypeptide may be substituted, inserted, or deleted, for example, to produce products with improved biological properties. Further, fragments of these polypeptides, especially biologically active fragments, are included. Yet more preferred polypeptides of this invention are human growth hormone, and atrial natriuretic peptides A, B and C, endotoxin, subtilisin, trypsin and other serine proteases Also preferred as polypeptide hormones that can be defined as any amino acid sequence produced in a first cell that binds specifically to a receptor on the same cell type (autocrine hormones) or a second cell type (non-autocrine) and caused a physiological response characteristic of the receptor-bearing cell. Among such polypeptide hormones are cytokines, lymphokines, neurotrophic hormones and adenohypophyseal polypeptide hormones such as growth hormone, prolactin, placental lactogen, luteinizing hormone, follicle-stimulating hormone, β-lipotropin, γ-lipotropin and the endorphins; hypothalamic release-inhibiting hormone such as corticotropin-release factors, growth hormone release-inhibiting hormone, growth hormone-release factor; and other polypeptide hormones such as atrial natriuretic peptides A, B or C.

2. Obtaining a First Gene (Gene 1) Encoding the Desired Polypeptide

The gene encoding the desired polypeptide (e.g. antibody) can be obtained my methods known in the art (see generally, Sambrook et al., Molecular Biology: A Laboratory Manual, Cold Spring Harbor Press, Cold Spring Harbor, N.Y., (1989)). If the sequence of the gene is known, the DNA encoding the gene may be chemically synthesized (Merrifield, *J. Am. Chem. Soc* .85: 2149 (1963)). If the sequence of the gene is not known, or if the gene has not previously been isolated, it may be cloned from a cDNA library (made from RNA obtained from a suitable tissue in which the desired gene is expressed) or from a suitable genomic DNA library. The gene is then isolated using an appropriate probe. For cDNA libraries, suitable probes include monoclonal or polyclonal antibodies (provided that the cDNA library is an expression library), oligonucleotides, and complementary or homologous cDNAs or fragments thereof. The probes that may be used to isolate the gene of interest from genomic DNA libraries include cDNAs or fragments thereof that encode the same or a similar gene, homologous genomic DNAs or DNA fragments, and oligonucleotides. Screening the cDNA or genomic library with the selected probe is conducted using standard procedures as described in chapters 10–12 of Sambrook et al., supra.

An alternative means to isolating the gene encoding the polypeptide (e.g. antibody) of interest is to use polymerase chain reaction methodology (PCR) as described in section 14 of Sambrook et al., supra. This method requires the use of oligonucleotides that will hybridize to the gene of interest, thus, at least some of the DNA sequence for this gene must be known in order to generate the oligonucleotides.

After the gene has been isolated, it may be inserted into a suitable vector (preferably a plasmid) for amplification, as described generally in Sambrook et al., supra.

3. Constructing Replicable Expression Vectors

While several types of vectors are available and may be used to practice this invention, plasmid vectors are the preferred vectors for use herein, as they may be constructed with relative ease, and can be readily amplified. Plasmid vectors generally contain a variety of components including promoter, signal sequences, phenotypic selection genes, origin of replication sites, and other necessary components as are known to those of ordinary skill in the art.

Promoters most commonly used in prokaryotic vectors include the lac Z promoter system, the alkaline phosphatase pho A promoter, the bacteriophage λPL promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al., supra. While these are the most commonly used promoters, other suitable microbial promoters may be used as well.

Preferred promoters for practicing this invention are those that can be tightly regulated such that expression of the fusion gene can be controlled. If expression is uncontrolled, leading to multiple copies of the fusion protein on the surface of the phagemid, there could be multipoint attachment of the phagemid with the target. This multipoint attachment, also called "avidity" or "chelate effect" is believed to result in the selection of false "high affinity" polypeptides caused by multiple copies of the fusion protein being displayed on the phagemid particle in close proximity to one another in a manner as to "chelate" the target. When multipoint attachment occurs, the effective or apparent Kd may be as high as the product of the individual Kds for each copy of the displayed fusion protein.

Through tight regulation of the expression of the fusion protein such that no more than a minor amount, i.e., fewer than about 1%, of the phagemid particles contain multiple copies of the fusion protein, the "chelate effect" is overcome allowing proper selection of high affinity polypeptides. Thus, depending on the promoter, culturing conditions of the host are adjusted to maximize the number of phagemid particles containing a single copy of the fusion protein and minimize the number of phagemid particles containing multiple copies of the fusion protein.

Preferred promoters used to practice this invention are the lac Z promoter and the pho A promoter. The lac Z promoter is regulated by the lac repressor protein lac i, and thus transcription of the fusion gene can be controlled by manipulation of the level of the lac repressor protein. By way of illustration, the phagemid containing the lac Z promoter is grown in a cell strain that contains a copy of the lac i repressor gene, a repressor for the lac Z promoter. Exemplary cell strains containing the lac i gene include JM 101 and XL-1 blue. In the alternative, the host cell can be cotransfected with a plasmid containing both the repressor lac i and lac Z promoter. Occasionally both of the above techniques are used simultaneously, that is, phagemid particles containing the lac Z promoter are grown in cell strains containing the lac i gene and the cell strains are cotransfected with a plasmid containing both the lac Z and lac i genes. Normally when one wishes to express a gene, to the transfected host above one would add an inducer such as isopropylthiogalactoside (IPTG). In the present invention however, this step is omitted to (a) minimize the expression of the gene III fusions per phagemid number) and to (b) prevent poor or improper packaging of the phagemid caused by inducers such as IPTG even at low concentrations. Typically, when no inducer is added, the number of fusion proteins per phagemid particle is above 0.1 (number of bulk fusion proteins number of phagemid particles). The most preferred promoter used to practice this invention is pho A. This promoter is believed to be regulated by the level of inorganic phosphate in the cell where the phosphate acts to down-regulate the activity of the promoter. Thus, by depleting cells of phosphate, the activity of the promoter can be increased. The desired result is achieved by growing cells in a phosphate enriched medium such as 2YT or LB thereby controlling the expression of the gene III fusion.

One other useful component of vectors used to practice this invention is a signal sequence. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., *Gene* 68; 193 (1983)), MalE, PhoA and other genes. A preferred prokaryotic signal sequences for practicing this invention is the *E. coli* heat-stable enterotoxin II(STII) signal sequence as described by Chang et al., *Gene* 55: 189 (1987)).

Another useful component of the vectors used to practice this invention is phenotypic selection genes. Typical phenotypic selection genes are those encoding proteins that confer antibiotic resistance upon the host cell. By way of illustration, the ampicillin resistance gene (amp), and the tetracycline resistance (tet) are readily employed for this purpose.

Construction of suitable vectors comprising the aforementioned components as well as the gene encoding the described polypeptide (gene 1) are prepared using standard recombinant DNA procedures as described in Sambrook et al., supra. Isolated DNA fragments to be combined to form the vector are cleaved, tailored, and ligated together in a specific order and orientation to generate the desired vector.

The DNA is cleaved using the appropriate restriction enzyme or enzymes in a suitable buffer. In general, about 0.2–1 μg of plasmid or DNA fragments is used with about 1–2 units of the appropriate restriction enzyme in about 20 μl of buffer solution. Appropriate buffers, DNA concentrations, and incubation times and temperatures are specified by the manufacturers of the restriction enzymes. Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15° C. with 10 units of the Kienow fragment of DNA polymerase I (Klenow) in the presence of the four deoxynucleotide triphosphates. The DNA is then purified by phenol-chloroform extraction and ethanol precipitation.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30–6.33 of Sambrook et al., supra.

The DNA fragments that are to be ligated together (previously digested with the appropriate restriction enzymes such that the ends of each fragment to be ligated are compatible) are put in solution in about equimolar amounts. The solution will also contain ATP, ligase buffer and a ligase such as T4 DNA ligase at about 10 units per 0.5 μg of DNA. If the DNA fragment is to be ligated into a vector, the vector is at first linearized by cutting with the appropriate restriction endonuclease(s). The linearized vector is then treated with alkaline phosphatase or calf intestinal phosphatase. The phosphatasing prevents self-ligation of the vector during the ligation step.

After ligation, the vector with the foreign gene now inserted is transformed into a suitable host cell. Prokaryotes are the preferred host cells for this invention. Suitable prokaryotic host cells include *E. coli* strain M101*, E. coli* K12 strain 294 (ATCC number 31,446), *E. coli* strain W3110 (ATCC number 27,325), *E. coli* X1776 (ATCC number 31,537), *E. coli* XL-1 Blue (stratagene), and *E. coli* B; however, many other strains of *E. coli*, such as HB101, NM522, NM538, NM539, and many other species and genera of prokaryotes may be used as well. In addition to the *E. coli* strains listed above, bacilli such as *Bacillus subtilis* other enterobacteriaceae such as *Salmonella typhimurium* or *Serratia marcesans*, and various *Pseudomonas* species may all be used as hosts.

Transformation of prokaryotic cells is readily accomplished using the calcium chloride method as described in section 1.82 of Sambrook et al, supra. Alternatively, electroporation (Neumann et al., *EMBO J.* 1: 841 (1982)) may be used to transform these cells. The transformed cells are selected by growth on an antibiotic, commonly tetracycline (tet) or ampicillin (amp), to which they are rendered resistant due to the presence of tet and/or amp resistance genes on the vector.

After selection of the transformed cells, these cells are grown in culture and the plasmid DNA (or other vector with the foreign gene inserted) is then isolated. Plasmid DNA can be isolated using methods known in the art. Two suitable methods are the small scale preparation DNA and the large-scale preparation of DNA as described in sections 1.25–1.33 of Sambrook et al., supra. The isolated DNA can be purified by methods known in the art such as that described in section 1.40 of Sambrook et al., supra. This purified plasmid DNA is then analyzed by restriction mapping and/or DNA sequencing. DNA sequencing is generally performed by either the method of Messing et al., *Nucleic Acids Res*. 9: 309 (1981) or by the method of Maxam et al., *Meth. Enzymol*. 65: 499 (1980).

4. Gene Fusion

The phage affinity step of the present invention contemplates fusing the gene enclosing the desired polypeptide (gene 1) to a second gene (gene 2) such that a fusion gene is generated during transcription. Gene 2 is typically a coat protein gene of a phage, and preferably it is the phage M13 gene III coat protein, or a fragment thereof. Fusion of genes 1 and 2 may be accomplished by inserting gene 2 into a particular site on a plasmid that contains gene 1, or by inserting gene 1 into a particular site on a plasmid that contains gene 2.

Insertion of a gene into a plasmid requires that the plasmid be cut at the precise location that the gene is to be inserted. Thus, there must be a restriction endonuclease site at this location (preferably a unique site such that the plasmid will only be cut at a single location during restriction endonuclease digestion). The plasmid is digested, phosphatased, and purified as described above. The gene is then inserted into this linearized plasmid by ligating the two DNAs together. Ligation can be accomplished if the ends of the plasmid are compatible with the ends of the gene to be inserted. If the same restriction enzymes is used to cut both the plasmid and isolate the gene to be inserted, the DNAs can be ligated together directly using a ligase such as bacteriophage T4 DNA ligase and incubating the mixture at 16° C. for 1–4 hours in the presence of ATP and ligase buffer as described in section 1.68 of Sambrook et al., supra. If the ends are not compatible, they must first be made blunt by using the Klenow fragment of DNA polymerase I or bacteriophage T4 DNA polymerase, both of which require the. four deoxyribonucleotide triphosphates to fill-in overhanging single-stranded ends of the digested DNA. Alternatively, the ends may be blunted using a nuclease such as nuclease S1 or mung-bean nuclease, both of which function by cutting back the overhanging single strands of DNA. The DNA is then relegated using a ligase as described above. In some cases, it may not be possible to blunt the ends of the gene to be inserted, as the reading frame of the coding region will be altered. To overcome this problem, oligonucleotide linkers may be used. The linkers serve as a bridge to connect the plasmid to the gene to be inserted. These linkers can be made synthetically as double stranded or single-stranded DNA using standard methods. The linkers have one end that is compatible with the ends of the gene to be inserted; the linkers are first ligated to this gene using ligation methods described above. The other end of the linkers is designed to be compatible with the plasmid for ligation. In designing the linkers, care must be taken to not destroy the reading frame of the gene to be inserted or the reading frame of the gene contained on the plasmid. In some cases, it may be necessary to design the linkers such that they code for part of an amino acid, or such that they encode for one or more amino acids.

Between gene 1 and gene 2, DNA encoding a termination codon may be inserted, such termination codons are UAG (amber), UAA (ocher) and UGA (opel), *Microbiology*, Davis et al., Harper & Row, New York, 1980, pp 237, 245–47 and 274). The termination codon expressed in a wild type host cell results in the synthesis of the gene 1 protein product without the gene 2 protein attached. However, growth in a suppressor host cell results in the synthesis of detectable quantities of fused protein. Such suppressor host cells contain a tRNA modified to inset an amino acid in the termination codon position of the mRNA thereby resulting in production of detectible amounts of the fusion protein. Such suppressor host cells are well known and described, such as *E. coli* suppressor strain (Bullock et al., *BioTechnologies* 5, 376–379 (1987)). Any acceptable method may be used to place such a termination codon into the mRNA encoding the fusion polypeptide.

Between gene 1 and gene 2, DNA encoding a termination codon may be inserted, such termination codons are UAG (amber), UAA (ocher) and UGA (opel), *Microbiology*, Davis et al., Harper & Row, New York, 1980, pp 237, 245–47 and 274). The termination codon expressed in a wild type host cell results in the synthesis of the gene 1 protein product without the gene 2 protein attached. However, growth in a suppressor host cell results in the synthesis of detectable quantities of fused protein. Such suppressor host cells contain a tRNA modified to inset an amino acid in the termination codon position of the mRNA thereby resulting in production of detectable amounts of the fusion protein. Such suppressor host cells are well known and described, such as *E. coli* suppressor strain (Bullock et al., *BioTechnologies* 5, 376–379 (1987)). Any acceptable method may be used to place such a termination codon into the mRNA encoding the fusion polypeptide.

5. Alteration (Mutation) of Gene 1 at Selected Positions

Gene 1, encoding the desired polypeptide, may be altered at one or more selected codons. However, the codon corresponding to the isomerizable aspartyl residue must be changed. An alteration is defined as a substitution, deletion, or insertion of one or more codons in the gene encoding the polypeptide that results in a change in the amino acid sequence of the polypeptide as compared with the unaltered or native sequence of the same polypeptide. Preferably, the alterations will be by substitution of at least one amino acid with any other amino acid in one or more regions of the molecule. The alterations may be produced by a variety of methods known in the art. These methods include but are not limited to oligonucleotide-mediated mutagenesis and cassette mutagenesis.

a. Oligonucleotide-Mediated Mutagenesis

Oligonucleotide-mediated mutagenesis is the preferred method for preparing substitution, deletion, and insertion variants of gene 1. This technique is well known in the art as described by Zoller et al., *Nucleic Acids Res.* 10: 6487–6504 (1987). Briefly, gene 1 is altered by hybridizing an oligonucleotide encoding the desired mutation to a DNA template, where the template is the single-stranded form of the plasmid containing the unaltered or native DNA sequence of gene 1. After hybridization, a DNA polymerase is used to synthesize an entire second complementary strand of the template which will thus incorporate the oligonucleotide primer, and will code for the selected alteration of gene 1.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA* 75: 5765 (1978).

The DNA template can only be generated by those vectors that are either derived from bacteriophage M13 vectors (the commonly available M13mp18 and M13mp19 vectors are suitable), or those vectors that contain a single-stranded phage origin or replication as described by Viera et al., *Meth. Enzymol*. 153: 3 (1987). Thus, the DNA that is to be mutated must be inserted into one of these vectors in order to generate a single-stranded template. Production of the single-stranded template is described in sections 4.21–4.41 of Sambrook et al., supra.

To alter the native DNA sequence, the oligonucleotide is hybridized to the single stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM-101. After growing the cells, they are plated onto agarose plates and screened using the oligonucleotide primer radiolabelled with $^{32}$-Phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one or two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, and oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

b. Cassette Mutagenesis

This method is also a preferred method for preparing substitution, deletion, and insertion variants of gene 1. The method is based on that described by Wells et al. *Gene* 34: 315 (1985). The starting material is the plasmid (or other vector) comprising gene 1, the gene to be mutated. The codon(s) in gene 1 to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in gene 1. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of gene 1.

6. Obtaining DNA Encoding the Desired Protein.

In an alternative embodiment, this invention contemplates production of variants of a desired protein containing one or more subunits. Each subunit is typically encoded by separate genes. Each gene encoding each subunit can be obtained by methods known in the art (see, for example, Section II). In some instances, it may be necessary to obtain the gene encoding the various subunits using separate techniques selected from any of the methods described in Section II.

When constructing a replicable expression vector where the protein of interest contains more than one subunit, all subunits can be regulated by the same promoter, typically located 5' to the DNA encoding the subunit, or each may be regulated by the same promoter, typically located 5' to the DNA encoding the subunits, or each may be regulated by a separate promoter suitably oriented in the vector so that each promoter is operably linked to the DNA it is intended to regulate. Selection of promoters is carried out as described in Section III above.

In constructing a replicable expression vector containing DNA encoding the protein of interest having multiple subunits, the reader is referred to FIGS. 11A and B, where, by way of illustration, a vector is diagramed showing DNA encoding each subunit of an antibody fragment. This figure shows that, generally, one of the subunits of the protein of interest will be fused to a phage coat protein such as M13 gene III. This gene fusion generally will contain its own signal sequence. A separate gene encodes the other subunit or subunits, and it is apparent that each subunit generally has its own signal sequence. FIGS. 11A and 11B also show that a single promoter can regulate the expression of both subunits. Alternatively, each subunit may be independently regulated by a different promoter. The protein of interest subunit-phage coat protein fusion construct can be made as described in Section IV above.

When constructing a family of variants of the desired multi-subunit protein, DNA encoding each subunit in the vector may be mutated in one or more positions in each subunit. When multi-subunit antibody variants are constructed, preferred sites of mutagenesis correspond to codons encoding amino acid residues located in the complementarity-determining regions (CDRs) of either the light chain, the heavy chain, or both chains. The CDRs are commonly referred to as the hypervariable regions. Methods for mutagenizing DNA encoding each subunit of the protein of interest are conducted essentially as described in Section V above.

7. Preparing a Target Molecule and Binding with Phagemid

Target proteins, such as receptors, may be isolated from natural sources or prepared by recombinant methods by procedures known in the art. By way of illustration, glycoprotein hormone receptors may be prepared by the technique described in McFarland et al, *Science* 245: 494–499 (1989), nonglycosylated forms expressed in *E. coli* are described by Fuh et al., *J. Biol. Chem* .265: 3111–3115 (1990). Other receptors can be prepared by standard methods.

The purified target protein may be attached to a suitable matrix such as agarose beads, acrylamide beads, glass beads, cellulose, various acrylic copolymers, hydroxylalkyl methacrylate gels, polyacrylic and polymethacrylic copolymers, nylon, neutral and ionic carriers, and the like. Attachment of the target protein to the matrix may be accomplished by methods described in *Methods in Enzymol*. 44 (1976), or by other means known in the art.

After attachment of the target protein to the matrix, the immobilized target is contacted with the library of phagemid particles under conditions suitable for binding of at least a portion of. the phagemid particles with the immobilized target. Normally, the conditions, including pH, ionic strength, temperature and the like will mimic physiological conditions.

Bound phagemid particles ("binders") having high affinity for the immobilized target are separated from those having a low affinity (and thus do not bind to the target) by washing. Binders may be dissociated from the immobilized target by a variety of methods. These methods include competitive dissociation from the immobilized target by a variety of methods. These methods include competitive dissociation using the wild-type ligand, altering pH and/or ionic strength, and methods known in the art.

Suitable host cells are infected with the binders and helper phage, and the host cells are cultured under conditions suitable for amplification of the phagemid particles. The phagemid particles are then collected and the selection process is repeated one or more times until binders having the desired affinity for the target molecule are selected.

Optionally the library of phagemid particles may be sequentially contacted with more than one immobilized target to improve selectivity for a particular target. For example, it is often the case that a ligand such as hGH has more than one natural receptor. In the case of hGH, both the growth hormone receptor and the prolactin receptor bind the hGH ligand. It may be desirable to improve the selectivity of hGH for the growth hormone receptor over the prolactin receptor. This can be achieved by first contacting the library of phagemid particles with immobilized prolactin receptor, eluting those with a low affinity (i.e. lower than wild type hGH) for the prolactin receptor and then contacting the low affinity prolactin "binders" or non-binders with the immobilized growth hormone receptor, and selecting for high affinity growth hormone receptor binders. In this case an hGH mutant having a lower affinity for the prolactin receptor would have therapeutic utility even if the affinity for the growth hormone receptor were somewhat lower than that of wild type hGH. This same strategy may be employed to improve selectivity of a particular hormone or protein for its primary function receptor over its clearance receptor.

In another embodiment of this invention, an improved substrate amino acid sequence can be obtained. These may be useful for making better "cut sites" for protein linkers, or for better protease substrates/inhibitors. In this embodiment, an immobilizable molecule (e.g. hGH) receptor, biotin-avidin, or one capable of covalent linkage with a matrix) is fused to gene III through a linker. The linker will preferably by from 3 to 10 amino acids in length and will act as a substrate for a protease. A phagemid will be constructed as described above where the DNA encoding the linker region is randomly mutated to produce a randomized library of phagemid particles with different amino acid sequences at the linking site. The library of phagemid particles are then immobilized on a matrix and exposed to a desired protease. Phagemid particles having preferred or better substrate amino acid sequences in the linear region for the desired protease will be eluted, first producing an enriched pool of phagemid particles encoding preferred linkers. These phagemid particles are then cycled several more times to produce an enriched pool of particles encoding consensus sequence(s).

II. Generation of Antibodies

The starting antibody may be prepared using techniques available in the art or generating such antibodies. Exemplary methods for generating antibodies are described in more detail in the following sections.

The antibody is directed against an antigen of interest. Preferably, the antigen is a biologically important polypeptide an administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; growth hormone, including human growth hormone and bovine growth hormone; growth hormone releasing factor; parathyroid hormone; glucagon; clotting factors such as Protein C; atrial natriuretic factor; lung surfactant; a plasminogen activator, such as urokinase or human urine or tissue-type plasminogen activator (tPA); bombesin; thrombin; hemopoietic growth factor; tumor necrosis factor-alpha and -beta; enkephalinase; RANTES (regulated activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein; such as beta-lactamase; DNase; IgE, a cytotoxic T-lymphocyte associated antigen (CTLA), such as CTLA-4; inhibin; activin; vascular endothelial growth factors (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5 or NT-6, or a nerve growth factor such as NGF-β, platelet-derived growth factor (PDGF), fibroblast growth factors such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-1 and IGF-II) des(1-3)-IGF-I (brain IGF-I), insulin-like growth factor binding protein; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (Ils), e.g., IL-1 to IL-10; superoxide dismutase; T-cell receptors; surface membrane proteins; homing receptors; adressins; regulatory proteins; integrins such as CD11a, CD11b, CD11c, CD18, and ICAM, VLA-4 and VCAM; a tumor associated antigen such as HER2, HER3 or HER 4 receptor; and fragments of any of the above-listed peptides.

Preferred molecular targets for antibodies encompassed by the present invention include CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac12, p150,95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flk3 receptor; obesity (OB) receptor; mp1 receptor; CTLA-4; protein C etc. An especially preferred target is IgE.

The antibody is raised against the antigen derived from a first mammalian species. Preferably the first mammalian species is human. However, other mammals are contemplated such as farm, pet or zoo animals, e.g. where the antibody is intended to be used to treat such mammals. The antigen from the first mammalian species may be isolated from a natural source thereof for the purposes of generating an antibody thereagainst. However, as noted below, cells comprising the antigen can be used as immunogens for making antibodies. In other embodiments, the antigen is produced recombinantly or made using other synthetic methods. The antibody selected will normally have a sufficiently strong binding affinity for the antigen. For example, the antibody may bind the antigen from the first mammalian species with a binding affinity (Kd) value of no more than about $1\times10^{-7}$ M, preferably no more than about $1\times10^{-8}$ and most preferably no more than about $1\times10^{-9}$ M. Antibody affinities may be determined by saturation binding; enzyme linked immunoabsorbant (ELISA); and competition assays (e.g. RIAs) for example.

Also, the antibody may be subjected to other biological activity assays, e.g., in order to evaluate its effectiveness as a therapeutic. Such assays are known in the art and depend on the target antigen and intended use for the antibody. Examples include the keratinocyte monolayer adhesion assay and the mixed lymphocyte response (MFR) assay for CD11a (each described in the Example below); tumor growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062).

To screen for antibodies which bind to a particular epitope on the antigen of interest (e.g., those which block binding of the MHM24 antibody, a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270: 1388–1394 (1995), can be performed to determine whether the antibody binds an epitope of interest.

Species-dependence of the antibody is then determined. The binding affinity of the antibody for a homologue of the antigen used to generate the antibody (where the homologue is from the "second mammalian species") is assessed using techniques such as those described above. In preferred embodiments, the second mammalian species is a nonhuman mammal to which the antibody will be administered in preclinical studies. Accordingly, the second mammalian species may be a nonhuman primate, such as rhesus, cynomolgus, baboon, chimpanzee and macaque. In other embodiments, the second mammalian species may be a rodent, cat or dog, for example. The species-dependent antibody will normally have a binding affinity for the antigen from the second nonhuman mammalian species which is at least about 50 fold, or at least about 500 fold, or at least about 100 fold, weaker than its binding affinity for the antigen from the first mammalian species. This binding affinity will normally be such that the species-dependent antibody cannot effectively be used for preclinical studies in the second mammalian species.

While the preferred method of the instant invention for determining species-dependence (and for evaluating antibody mutants with improved properties; see below) is to quantify antibody binding affinity, in other embodiments of the invention, one or more biological properties of the species-dependent antibody and antibody mutant are evaluated in addition to, or instead of, binding affinity determinations. Exemplary such biological assays are described above. Such assays are particularly useful where they provide an indication as to the therapeutic effectiveness of the antibody. Normally, though not necessarily, antibodies which show improved properties in such assays, will also have an enhanced binding affinity. Thus, in one embodiment of the invention where the assay of choice is a biological activity assay other than a binding affinity assay, the species-dependent antibody will normally have a "biologically activity" using "material" (e.g., antigen, cell, tissue, organ or whole animal) from the second mammalian species which is at least about 50-fold, or at least about 500 fold, or at least about 1000 fold, less effective than its biological activity in a corresponding assay using reagents from the first mammalian species.

The species-dependent antibody is then altered so as to generate an antibody mutant which has a stronger binding affinity for the antigen from the second mammalian species, than the species-dependent antibody. The antibody mutant preferably has a binding affinity for the antigen from the nonhuman mammal which is at least about 10 fold stronger, preferably at least about 20 fold stronger, more preferably at least about 500 fold stronger, and sometimes at least about 100 fold or 200-fold stronger, than the binding affinity of the species-dependent antibody for the antigen. The enhancement in binding affinity desired or required will depend on the initial binding affinity of the species-dependent antibody. However, the assay used is a biological activity assay, the antibody mutant preferably has biological activity in the assay of choice which is at least about 100 fold better, preferably at least about 20 fold better, more preferably at least about 50 fold better, and sometimes at least about 100 fold or 200 fold better, than the biological activity of the species-dependent antibody in that assay.

To generate the antibody mutant, one or more amino acid alterations (e.g. substitutions are introduced in one or more alterations (e.g. substitutions) of framework region residues may be introduced in the species-dependent antibody where the result is an improvement in the binding affinity of the antibody mutant for the antigen from the second mammalian species. Example of framework region residues to modify include those which non-covalently bind antigen directly (Amit et al., *Science* 233: 747–753 (1986)); interact with/effect the conformation of a CDR (Chothia et al., *J. Mo. Biol.* 196: 901–917 (1987)); and/or participate in the VL-VH interface (EP 239 400 B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alterations.

The hypervariable region residues which are altered may be changed randomly, especially where the starting binding affinity of the species-dependent antibody for the antigen form the second mammalian species is such that such randomly produced antibody mutants can be readily screened.

Techniques for producing antibodies, which may be species-dependent and therefore require modification according to the techniques elaborated herein, follow:

A. Antibody Preparation (i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or maybe cells which have been transformed by recombinant techniques to express the transmembrane molecule. Other antigens and forms thereof useful for preparing antibodies will be apparent to those in the art.

(ii) Polyclonal Antibodies

Polyclonal antibodies are preferably raised in non-human mammals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, thionyl chloride, or $R^1N{=}C{=}CR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture protein fusions. Also, aggregating agents such as alum are suitably used to enhance the immune response.

The mammalian antibody selected will normally have a sufficiently strong binding affinity for the antigen. For example, the antibody may bind the human anti-IgE antigen with a binding affinity (Kd) value of no more than about $1\times10^{-7}$ M, preferably no more than about $1\times10^{-8}$ and most preferably no more than about $1\times10^{-9}$ M. Antibody affinities may be determined.by saturation binding; enzyme-linked immunosorbent assay (ELISA); and competition assays (e.g., radioimmunoassays).

To screen for human anti-IgE antibodies, a routine cross-linking assay such as that described in *Antibodies, A Laboratory Manual*, Cold Spring Harbor Laboratory, Ed Harlow and David Lane (1988) can be performed. Alternatively, epitope mapping, e.g., as described in Champe, et al. *J. Biol. Chem*. 270: 1388–1394 (1995), can be performed to determine binding.

While the preferred method for determining efficacy of the polypeptide or antibody is through quantification of antibody binding affinity, other embodiments envision the evaluation of one or more biological properties of the antibody in addition to, or instead of binding affinity determinants. Such assays are particularly useful where they provide and indication as to the therapeutic effectiveness of the antibody. Normally, though not necessarily, antibodies which show improved properties in such assays, will also have an enhanced binding affinity.

(iii) Monoclonal Antibodies

Monoclonal antibodies are antibodies which recognize a single antigenic site. Their uniform specificity makes monoclonal antibodies much more useful than polyclonal antibodies, which usually contain antibodies that recognize a variety of different antigenic sites.

Monoclonal antibodies may be made using the hybridoma method first described by Kohler et al., *Nature,* 256: 495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principals and Practice*, pp. 590–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phophoribosyl transferase (HGPRT or HPRT), the culture medium for the hybridomas typically will include hypoxanthine, aminopterin, and thymidine (HAT medium), substances which prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available form the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbar, *J. Immunol*. 133: 3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principals and Practice*, pp. 59–103, Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed.into expression vectors, which are then transferred into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature* 348: 552–554 (1990). Clackson et al., *Nature* 352: 624–628 (1991) and Marks et al., *J. Mol. Biol*. 222: 581–597 (1991) describe the isolation of murine and human antibodies, respectively, using phage libraries. Subsequent publications describe the production of high affinity (nM range) human antibodies by chain shuffling (Marks et al., *Bio/Technology* 10: 779–783 (1992)), as well as combinatorial infection and in vivo recombination as a strategy for constructing very large phage libraries (Waterhouse et al., *Nuc. Acids. Res*. 21: 2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison et al., *Proc. Natl Acad. Sci. USA* 81: 6851 (1984)), or by covalently joining to the immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Generation of Mutant Antibodies

Once the species-dependent antibody has been identified and isolated, it is often useful to generate a variant antibody or mutant, wherein one or more amino acid residues are altered in one or more of the hypervariable regions of the mammalian antibody. Alternatively, or in addition, one or more alterations (e.g. substitutions) of framework residues may be introduced in the mammalian antibody where these result in an improvement in the binding affinity of the antibody mutant for human IgE. Examples of framework region residues to modify include those which non-covalently bind antigen directly (Amit et al. *Science* 233: 747–753 (1986)); interact with/effect the conformation of CDR (Chothia et al. *J. Mol. Biol*. 196: 901–917 (1987)); and/or participate in the VL-VH interface (EP 239 400 B1). In certain embodiments, modification of one or more of such framework region residues results in an enhancement of the binding affinity of the antibody for the human antigen. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues which are altered may be changed randomly, especially where the starting binding affinity of the species-dependent antibody is such that randomly produced antibody mutants can be readily screened.

One useful procedure for generating antibody mutants is known as "alanine scanning mutagenesis" (Cunningham, B. C. and Wells, J. A. *Science* 244: 1081–1085 (1989); Cunningham, B. C. and Wells, J. A. *Proc. Natl. Acad. Sci. U.S.A.* 84, 6434–6437 (1991)). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity as described herein. Similar substitutions can be attempted with other amino acids, depending upon the desired property imparted by the scanning residues.

The invention also provides a more systematic method for identifying amino acid residues to modify. According to this method, one identifies hypervariable region residues in the species-dependent antibody which are involved in binding the first mammalian species and those hypervariable region residues involved in binding a homologue of that antigen from the second mammalian species. To achieve this, an alanine scan of the hypervariable region residues of the species-dependent antibody can be performed, with each ala-mutant being tested for binding to the first and second mammalian species. The hypervariable region residues involved in binding the antigen from the first mammalian species (e.g. human), and those involved in binding the homologue of the antigen from the second mammalian species (e.g. non human) are thereby identified. Preferably, those residue(s) significantly involved in binding the antigen from the second mammalian species, (e.g., nonhuman mammal), but not the antigen from the first mammalian species (e.g. human), are chosen as candidates for modification. In another embodiment, those residue(s) significantly involved in binding the antigen from both the first and second mammalian species are selected to be modified. In yet a further, but less preferred embodiment, those residues which are involved in binding the antigen from human IgE, but not the homologous mammalian (non-human) IgE, are selected for modification. Such modification can involve deletion of the residue or insertion of one or more residues adjacent the residue of interest. However, normally the modification involves substitution of the residue for another amino acid.

Typically, one would start with a conservative substitution such as those shown in Table A below under the heading of “preferred substitutions”. If such substitutions results in a change in biological activity (e.g. binding affinity), then more substantial changes, denominated “exemplary substitutions” in Table A, or as further described below in reference to amino acid classes, are introduced and the products screened.

TABLE A

Conservative Substitutions of Amino Acid Residues

| Original Residue | Exemplary Substitutions | Preferred Substitutions | DNA Codons |
|---|---|---|---|
| Ala (A) | val, leu, ile | val | GCA, GCC, GCG, GCU |
| Arg (R) | lys, gln, asn | lys | AGA, AGG, CGA, CGC, CGG, CGU |
| Asn (N) | gln, his, lys, arg | gln | AAC, AAU |
| Asp (D) | glu | glu | GAC, GAU |
| Cys (C) | ser | ser | UGC, UGU |
| Gln (Q) | asn | asn | CAA, CAG |
| Glu (E) | asp | asp | GAA, GAG |
| Gly (G) | pro, ala | ala | GGA, GGC, GGG, GGU |
| His (H) | asn, gln, lys, arg | arg | CAC, CAU |
| Ile (I) | leu, val, met, ala, phe, norleucine | leu | AUA, AUC, AUU |
| Leu (L) | norleucine, ile, val, met, ala, phe | ile | UUA, UUG, CUA, CUC, CUG, CUU |
| Lys (K) | arg, gln, asn | arg | AAA, AAG |
| Met (M) | leu, phe, ile | leu | AUG |
| Phe (F) | leu, val, ile, ala, tyr | leu | UUC, UUU |
| Pro (P) | ala | ala | CCA, CCC, CCG, CCU |
| Ser (S) | thr | thr | AGC, AGU, UCA, UCC, UCG, UCU |
| Thr (T) | ser | ser | ACA, ACC, ACG, ACU |
| Trp (W) | tyr, phe | tyr | UGG |
| Tyr (Y) | trp, phe, thr, ser | phe | UAC, UAU |
| Val (V) | ile, leu, met, phe, ala, norleucine | leu | GUA, GUC, GUG, GUU |

Even more substantial modifications in the antibodies' biological properties are accomplished by selecting substitutions that differ significantly in their effect on maintaining: (a) the structure of the polypeptide backbone in the area of the substitution, for example, as a sheet or helical conformation; (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gin;
(3) acidic: asp, glu;
(4) basic: his, lys, arg;
(5) residues that influence chain orientation: gly, pro, and
(6) aromatic: trp, tyr, phe.

Non-conservative substitutions will entail exchanging a member of one of these classes for another class.

Nucleic acid molecules encoding amino acid sequence mutants are prepared by a variety of methods known in the art. These methods include, but are not limited to, oligonucleotide-mediated (or site-directed) mutagenesis, PCR mutagenesis, and cassette mutagenesis of an earlier prepared mutant or a non-mutant version of the species-dependent antibody. The preferred method for making mutants is site directed mutagenesis (see Kunkel, *Proc. Natl. Acad. Sci. USA* 82: 488 1985)).

In certain embodiments, the antibody mutant will only have a single hypervariable region residue substituted, e.g. from about two to about fifteen hypervariable region substitutions.

Ordinarily, the antibody mutant with improved biological properties will have an amino acid sequence having at least 75% amino acid sequence identity or similarity with the amino acid sequence or either the heavy or light chain variable domain of the mammalian anti-human IgE antibody, more preferably at least 80%, more preferably at least 85%, even more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties, supra) with the species-dependent antibody residues, after aligning the sequences and introducing gaps, if necessary, to achieve the maximum percent sequence identity.

Alternatively, antibody mutants can be generated by systematic mutation of the CDR regions of the heavy and light chains of the anti-IgE antibody. The preferred procedure for generating such antibody mutants involves the use of affinity maturation using phage display (Hawkins et al., *J. Mol. Biol.* 254: 889–896 (1992) and Lowman et al., *Biochemistry* 30(45): 10832–10838(1991)). Bacteriophage coat-protein fusions (Smith, *Science* 228: 1315 (1985); Scott and Smith, *Science* 249: 386 (1990); Cwirla et al. *Proc. Natl. Acad Sci. USA* 8: 309 (1990); Devlin et al. *Science* 249: 404 (1990); reviewed by Wells and Lowman, *Curr. Opin. Struct. Biol.* 2: 597 (1992); U.S. Pat. No. 5,223,409) are known to be useful for linking the phenotype of displayed proteins or peptides to the genotype of bacteriophage particles which encode them. The F(ab) domains of antibodies have also been displayed on phage (McCafferty et al., *Nature* 348: 552 (1990); Barbas et al. *Proc. Natl. Acad. Sci. USA* 88: 7978 (1991); Garrard et al. *Biotechnol.* 9: 1373 (1991)).

Monovalent phage display consists of displaying a set of protein variants as fusions to a bacteriophage coat protein in such a way as to limit display of the variants to only one copy per several phage particles (Bass et al., *Proteins* 8: 309 (1990). Affinity maturation, or improvement of equilibrium binding affinities of various proteins, has previously been achieved through successive application of mutagenesis, monovalent phage display, functional analysis, and addition of favored mutations, as exemplified in the case of human growth hormone (Lowman & Wells, *J. Mol. Biol.* 234: 564–578 (1993); U.S. Pat. No. 5,534,617), as well as the F(ab) domains of antibodies (Barbas et al., *Proc: Natl. Acad. Sci. USA* 91: 3809 (1994); Yang et al., *J. Mol. Biol.* 254: 392 (1995).

Libraries of many ($10^6$) protein variants, differing at defined positions in their sequence, can be constructed on bacteriophage particles, each of which contains DNA encoding the particular protein variant. After cycles of affinity purification, using an immobilized antigen, individual bacteriophage clones are isolated, and the amino acid sequence of their displayed protein is deduced from their DNA.

(a) Humanized and Human Antibodies

Humanization is a technique for making a chimeric antibody wherein substantially less than an intact human variable domain has been substituted by the corresponding sequence from a non-human species. A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al, *Nature* 321: 522–525 (1986); Riechman et al., *Nature* 332: 323–327 (1988); Verhoeyen et al., *Science* 239: 1534–1536 (1988)), by substituting rodent Complementarity Determining Regions (CDR's) or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. As practiced in the present invention, the humanized IgE antibodies have some CDR residues and possible some FR residues substituted by residues from analogous sites in murine antibodies.

The choice of human variable domains, both light and heavy, to be used in making the humanized antibodies is very important to reduce antigenicity. According to the so-called "best fit" method, the sequence of the variable domain of a rodent antibody is screened against the entire library or known human variable-domain sequences. The human sequence which is closest to that of the rodent is then accepted as the human framework for the humanized antibody (Sims et al., *J. Immunol.* 151: 2296 (1993); Chothia et al., *J. Mol. Biol.* 196: 901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89: 4285 (1992); Presta et al., *J. Immunol.* 151: 2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Models for particular antibody domains, for example, VH and VL domains, are constructed separately from consensus sequences based upon F(ab) structures which have similar sequences. Three-dimensional immunoglobulin models are commonly available and are familiar to those skilled in the art. Computer programs are available which illustrate and display probably three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. For example in modeling the fragment F(ab)-12 in Example 2, the murine MAE11 was used as a template for inspiration of CDR and framework residues to modify in conjunction with molecular modeling to arrive at the mutant sequence.

As another example, there can be mentioned the control antibody Mab4d5. Here, the models were constructed based upon several Fab structures from the Brookhaven protein data bank (entries 1FB4, 2RHE, 2MCP, 3FAB, 1FBJ, 2HFL and 1REI). The F(ab) fragment KOL (Marquart, M. et al., *J. Mol. Biol.* 141: 369–391 (1980)) as first chosen as a template for VL and VH domains and additional structures were then superimposed upon this structure using their main chain atom coordinates (INSIGHT program, Biosym Technologies). Similar programs and techniques are utilized for modeling the desired antibody.

A typical analysis using molecular modeling may be conducted as follows: The distance from the template Cα to the analogous Cα in each of the superimposed structures is calculated for each given residue position. Generally, if all (or nearly all) Cα-Cα distances for a given residue are ≦1 Å, then that position is included in the consensus structure. In some cases the β-sheet framework residues will satisfy these criteria whereas the CDR loops may not. For each of these selected residues, the average coordinates for individual N, Cα, C, O and Cβ atoms are calculated and then corrected for resultant deviations from non-standard bond geometry by 50 cycles of energy minimization using a commercially available program such as the DISCOVER program (Biosym Technologies) with the AMBER forcefield (Weiner, S.J. et al., *J. Amer. Chem. Soc.* 106: 765–784 (1984)), and the Cα coordinates are fixed. The side chains of highly conserved residues, such as the disulfide-bridged cysteine residues, are then incorporated into the resultant consensus structure. Next, the sequences of the particular antibody VL and VH domains are incorporated starting with the CDR residues and using the tabulations of CDR conformations from Chothia et al. (Chothia, C. et al., *Nature* 342: 877–883 (1989)) as a guide. Side-chain conformations are chosen on the basis of Fab crystal structures, rotamer libraries (Ponder, J. W. & Richards, F. M., *J. Mol. Biol.* 193: 775–791 (1987)) and packing considerations. Since VH-CDR3 may not be assignable with the above criteria, models may be created from a search of similarly sized loops using the INSIGHT program, derived using packing and solvent exposure considerations, or created using other routine and commercially available techniques. It is preferable to subject the model to 5000 cycles of energy minimization.

In this way, framework residues can be selected and combined from the recipient and import sequences so that the desired antibody characteristics, such as increased affinity for the target antigen(s), is achieved. In general, the CDR residues are directly and most substantially involved in influencing antigen binding. This technique was used in the creation of F(ab)-12 in Example 2, where a combination of murine CDR residues was used in conjunction with molecular modeling to create a humanized, murine anti-IgE antibody fragment.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. Jakobovits et al., *Proc. Natl. Acad. Sci. USA* 90: 2551 (1993); Jakobovits et al., *Nature* 362: 255–258 (1993); Bruggermann et al. *Year in Immunol.* 7: 33 (1993); and Duchosal et al., *Nature* 355: 258 (1992). Human antibodies can also be derived from phage-display libraries (Hoogenboom et al., *J. Mol. Biol.* 227: 381 (1991); Marks et al., *J. Mol. Biol.* 222: 581–597 (1991); Vaughan et al., *Nature Biotech.* 14: 309 (1996)).

(b) Additional Modifications

Following production of the antibody mutant, the biological activity of that molecule relative to the species-dependent antibody is determined. As noted above, this may involve determining the binding affinity and/or other biological activities of the antibody. In a preferred embodiment of the invention, a panel of antibody mutants are prepared above and are screened for binding affinity for the antigen from the second mammalian species. One or more of the antibody mutants selected from this initial screen are optionally subjected to one or more further biological activity assays to confirm that the antibody mutant(s) with enhanced binding affinity are indeed useful, e.g. preclinical studies. In preferred embodiments, the antibody mutant retains the ability to bind the antigen from the first mammalian species with a binding affinity similar to the species-dependent antibody. This may be achieved by avoiding altering hypervariable region residues involved in binding the antigen from the anti-human antibody. In other embodiments, the antibody mutant may have a significantly altered binding affinity from the first mammalian species (e.g. the binding affinity for that antigen is preferably better, but may be worse than the species-dependent antibody).

The antibody mutant(s) so selected may be subjected to further modifications, oftentimes depending upon the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residues not involved in maintaining the proper conformation of the antibody mutant also may be substituted, generally with serine, to improve the oxidative stability of the molecule and prevent aberrant cross linking. Conversely, (a) cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of a sugar through an ether oxygen; For example, N-acetylgalactosamine, galactose, fucose or xylose bonded to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more seine or threonine residues to the sequence of the original antibody (for O-linked glycosylation sites).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24: 107–117 (1992) and Brennan et al., *Science* 229: 81 (1985)). However, these fragments can now be produced directly by recombinant host cells. For example, the antibody fragments can be isolated from the antibody phage libraries discussed above. Alternatively, $F(ab')_2$-SH fragments can be directly recovered from *E. coli* and chemically coupled to form $F(ab')_2$ fragments (Carter et al., *Bio/Technology* 10: 163–167 (1992)). According to another approach, F(ab') fragments can be isolated directly from recombinant host cell culture. Other techniques for the production of antibody fragments will be apparent to the skilled practitioner. In other embodiments, the antibody of choice is a single chain Fv fragment (scFv). (PCT patent application WO 93/16185).

(vi) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignan B cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-CD22/anti-saporin, anti-CD7/anti-saporin, anti-CD38/anti-sporin, anti-CEA/anti-ricin A chain, anti-interferon-α(IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA), BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3-anti-herpes simplex virus (HSV), anti-T-cell receptor: CD3 complex/anti-influenza, anti-FcγR/anti-HIV, BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horseradish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. $F(ab')_2$ bispecific antibodies).

Methods for making bispecific antibodies are known in the art. Traditional production of full length bispecific antibodies is based on the coexpression of two immunoglobulin heavy chain-light pairs, where the two chains have different specificities (Millstein et al., *Nature* 305: 537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10: 3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportion of the three polypeptide fragments in embodiment when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies, see for example, Suresh et al., *Methods in Enzymology* 121: 210 (1986).

According to another approach described in WO 96/27011, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with large side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81(1985) describes a procedure wherein intact antibodies are proteolytically cleaved to generate F(ab')2 fragments. These fragments are reduced in the presence of the dithiol complexing agent sodium arsenite to stabilize vincinal dithiols and prevent intermolecular disulfide formation. The F(ab') fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med*. 175: 217–225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol*. 148(5): 1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90: 6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruger et al., *J. Immunol*. 152: 5368 (1994).

Antibodies with more than two valencies are contemplated. For example, trispecific antibodies can be prepared. Tutt et al., *J. Immunol*. 147: 60 (1991).

(vii) Effector Function Engineering

It may be desirable to modify the antibody of the invention with respect to effector function, so as to enhance the effectiveness of the antibody in binding to IgE, for example. For example, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp. Med*. 176: 1191–1195 (1992) and Shopes, B., *J. Immunol*. 148: 2918–2922 (1993). Alternatively, an antibody can be engineered which has dual Fc regions and may thereby have enhanced complement lysis and ADCC capabilities. See Stevenson et al., *Anti-Cancer Drug Design* 3: 219–230 (1989).

(viii) Immunoconjugates

The invention also pertains to immunoconjugates comprising the antibody described herein conjugated to a cytotoxic agent such as a chemotherapeutic agent, toxin (e.g. and enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII and PAP-S), momordica charantia inhibitor, curin, crotin, sapaonaria officinalis inhibitor, gelonin, mitogellin, restrictocin, phenomycin, enomycin and the tricothecenes. A variety of radionuclides are available for the production of radioconjugate antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) proprionate (SPDP), iminothiolane (IT), bifunctional derivatives of imidoesters (such as dimethyl adipimidate HCL), active esters (such as disuccinimidyl suberate), aldehydes (such as dimethyl adipimidate HCL), active esters (such as disuccinimidyl suberate), aldehydes (such as glutarerdehyde), bis-azido compounds (such as bis-p-(azidobenzoyl) hexanediamine), bis-diazonium derivatives (such as bis-p(diazoniumbenzoyl)-ethylenediamine), diisocyantes (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14 labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, die antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(ix) Immunoliposomes

The antibody mutants disclosed herein may also be formulated as immunoliposomes. Liposomes containing the antibody are prepared by methods known in the art, such as described in Epstein et al., *Proc. Natl. Acad. Sci. USA* 82: 3688 (1985); Hwang et al., *Proc. Natl. Acad. Sci. USA* 77: 4030 (1980); and U.S. Pat. No. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidyicholine, cholesterol and PEG-derivatized phosphatidylethanolamine (PEG-PB). Liposomes are extruded through filters of defined pore size to yield liposomes with the desired diameter. Fab' fragments of the antibody of the present invention can be conjugated to the liposomes as described in Martin et al., *J. Biol. Chem*. 257: 286–288 (1982) via a disulfide interchange reaction. A chemotherapeutic agent (such as Doxorubicin) is optionally contained within the liposome. See Gabizon et al., *J. National Cancer Inst*. 81(19): 1484 (1989).

(x) Antibody Dependent Enzyme Mediated Prodrug Therapy (ADEPT)

The antibody of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxylpeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxylacetyl or phenylacetyl groups, respectively, into free drugs. Alternatively, antibodies with enzymatic activity, also known in the art as “abzymes”, can be used to convert to prodrugs of the invention into free active drugs (Massey, *Nature* 328: 457–458 (1987)). Antibody-abzyme conjugates can be prepared as described herein for delivery of the abzyme to a tumor cell population.

The enzymes of this invention can be covalently bound to the antibody mutant by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (Neuberger et al., *Nature* 312: 604–608 (1984)).

(xi) Antibody-salvage Receptor Binding Epitope Fusions

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment of by incorporating the epitope into a peptide tag that is then fused to the antibody fragment at either end or in the middle, e.g., by DNA or peptide synthesis).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fe domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fe region and transferred to the $C_L$ region or $V_L$ region, or both, of the antibody fragment.

(xii) Other Covalent Modifications of the Antibody

Covalent modifications of the antibody are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, α-bromo-β-(5-imidozoyl)proprionic acid, chloroacetyl phosphate, N-alkylmaleimides, 3-nitro-2-pyridyl disulfide, methyl 2-pyridyl disulfide, p-chloromercuribenzoate, 2-chloromercura-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins of use in radioimmunoassay.

Carboxyl side groups (aspartyl or glutamyl) are selectively modified by reaction with carbodiimides (R—N═C═C—R'), where R and R' are different alkyl groups, such as 1-cyclohexyl-3-(2-morpholinyl4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79–86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to: (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published 11 Sep. 1987, and in Aplin and Wriston, *CRC Crit. Rev. Biochem*., pp. 259–306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. *Arch. Biochem. Biophys*. 259: 52 (1987) and by Edge et al. *Anal. Biochem*. 118: 131 (1981). Enzymatic cleavage of carbohydrate moieties on antibodies can be achieved by the use of a variety of endo- and exo-glycosidases as described by Thotakura et al., *Meth. Enzymol*. 138: 350(1987).

Another type of covalent modification of the antibody comprises linking the antibody to one of a variety of nonproteinaceous polymers, e.g., polyethylene glycol, polypropylene glycol, or polyoxylalkylenes, in the manner set forth in U.S. Pat. Nos. 4,640,835; 4,496,689; 4,301,144; 4,670,417; 4,791,192 or 4,179,337.

B. Vectors, Host Cells and Recombinant Methods

The invention also provides isolated nucleic acid encoding an antibody mutant as disclosed herein, vectors and host cells comprising the nucleic acid, and recombinant techniques for the production of the antibody mutant.

For recombinant production of the antibody mutant, the nucleic acid encoding it is isolated and inserted into a replicable vector for further cloning (amplification of the DNA) or for expression. DNA encoding the monoclonal antibody mutant is readily isolated and sequenced using conventional procedures (e.g., by using oligonucleotide probes that are capable of binding specifically to genes encoding the heavy and light chains of the antibody mutant). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibody mutant of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, α-factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibody mutant.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known. for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contain methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phophotransferase (APH) can be selected by cell growth in medium containing a selection agent for the selectable marker such as an aminoglycosidic antibiotic, e.g., kanamycin, neomycin, or G418. (U.S. Pat. No. 4,965,199).

A suitable selection gene for use in yeast is the trp1 gene present in the yeast plasmid Yrp7 (Stinchcomb et al., *Nature* 282: 39 (1979)). The trp1 gene provides a selection marker for a mutant strain of yeast lacking the ability to grow in typtophan, for example, ATCC No. 44076 or PEP4–1. Jones, *Genetics* 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology* 8: 135 (1990). Stable multi-copy expression vectors for secretion of mature recombinant human serum albumin by industrial strains of *Kluveromyces* have also been disclosed. Fleer et al, *Bio/technology* 9: 968–975 (1991).

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phophoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian virus 40 (SV40), from heterologous mammalian promoters, e.g., the actin promoter or an immunoglobulin promoter, from heat-shock promoters—provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, human β-interferon cDNA has been expressed in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297: 17–18 (1982) on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteria such as *Escherichia*, e. g. *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. Subtilis* and *B. Licheniformis* (e.g., *B. Licheniformis* 41P disclosed in DD 266,710 published 12 Apr. 1989), *Pseudomonas* such as *P. aeruginosa*, and *Streptomyces*. One preferred *E. coli* cloning host is *E. coli*294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neu-*

*rospora crassa; Schwanniomyces* such as *Schwanniomyces occidentalis*; and filamentous fungi such as e.g., *Neurospora, Penicillium, Tolypocladium*, and *Aspergillus* hosts such as *A. Nidulans* and *A. niger.*

Suitable host cells for the expression of glycosylated antibodies are derived from multicellular organisms. In principal, any higher eukaryotic cell culture is workable, whether from vertebrate or invertebrate culture. Examples of invertebrate cells include plant and insect cells, Luckow et al., *Bio/Technology* 6, 47–55 (1988); Miller et al., Genetic Engineering, Setlow et al. eds. Vol. 8, pp. 277–279 (Plenam publishing 1986); Mseda et al., *Nature* 315, 592–594 (1985). Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A particular cell line of interest is insect cell line sf9. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Moreover, plant cells cultures of cotton, corn, potato, soybean, petunia, tomato, and tobacco and also be utilized as hosts.

However, interest has been greatest in vertebrate cells, and propagation of vertebrate cells in culture (tissue culture) has become a routine procedure. See *Tissue Culture*, Academic Press, Kruse and Patterson, eds. (1973). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen. Virol*. 36: 59 (1977)); baby hamster kidney cells (BHK, ATCC CCL 10); Chinese hamster ovary cells/-DHFR (CHO, Urlaub et al., *Proc. Natl. Acad. Sci. USA* 77: 4216 (1980)); mouse sertoli cells (TM4, Mather, *Biol. Reprod*. 23: 243–251 (1980)); monkey kidney cells (CV1 ATCC CCL 70); African green monkey cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci*. 383: 44–68 (1982)); MRC 5 cells; FS4 cells; and human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody mutant of this invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing host cells. In addition, any of the media described in Ham et al., *Meth. Enzymol*. 58: 44 (1979), Barnes et al., *Anal. Biochem*. 102: 255 (1980), U.S. Pat. Nos. 4,767,704; 4,657,866; 4,927,762; 4,560,655; or 5,122,469; WO 87/00195 or U.S. Pat. Re. 30,985 may be used as culture media for the host cells. Any of these media may be supplemented as necessary with hormones and/or other growth factors (such as insulin, transferrin, or epidermal growth factor), salts (such as X-chlorides, where X is sodium, calcium, magnesium; and phosphates), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Antibody Purification

When using recombinant techniques, the antibody mutant can be produced intracellularly, in the periplasmic space, or directly secreted into the medium. If the antibody mutant is produced intracellularly, as a first step, the particulate debris, either host cells or lysed fragments, is removed, for example, by centrifugation or ultrafiltration. Carter et al., *Bio/Technology* 10: 163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody mutant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel elecrophoresis, dialysis, and affinity chromatography, with affinity chromatography being the preferred purification technique. The suitability of protein A as an affinity ligand depends on the species and isotype of any immunoglobulin Fc domain that is present in the antibody mutant. Protein A can be used to purify antibodies that are based on human γ1, γ2 or γ4 heavy chains (Lindmark et al., *J. Immunol Meth*. 62: 1–13 (1983)). Protein G is recommended for all mouse isotypes and for human γ3 (Guss et al., *EMBO J*. 5: 1567–1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody mutant comprises a CH3 domain, the Bakerbond ABXTM resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody mutant to be recovered.

Following any preliminary purification step(s), the mixture comprising the antibody mutant of interest and contaminants may be subjected to low pH hydrophobic interaction chromatography using an elution buffer at a pH between about 2.5–4.5, preferably performed at low salt concentrations (e.g., from about 0–0.25M salt).

C. Pharmaceutical Formulations

Therapeutic formulations of the polypeptide or antibody are prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See *Remington's Pharmaceutical Sciences*, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives are added to retard microbial growth, and are added in amounts ranging from 0.2%–1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" are present to ensure isotonicity of liquid compositions of the present invention and include polhydric sugar alcohols, preferably trihydric or higher sugar alcohols, such as glycerin, erythritol, arabitol, xylitol, sorbitol and mannitol. Polyhydric alcohols can be present in an amount between 0.1% to 25% by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccharides such as raffinose; polysaccharides such as dextran. Stabilizers are present in the range from 0.1 to 10,000 weights per part of weight active protein.

Non-ionic surfactants or detergents (also known as "wetting agents") are present to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants are present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin micropheres, microemulsions, nano-particles and nanocapsules) or in macroemulsions. Such techniques are disclosed in *Remington's Pharmaceutical Sciences*, 16th edition, A. Osal, Ed. (1980).

The formulations to be used for in vivo administration must be sterile. This is readily accomplished, for example, by filtration through sterile filtration membranes.

Sustained-release preparations may be prepared. Suitable examples of sustained-release preparations include semipermeable matrices of solid hydrophobic polymers containing the antibody mutant, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in promoting the survival of sensory neurons may provide a local therapeutic agent concentration of between about 5 and 20 ng/ml, and, preferably, between about 10 and 20 ng/ml. In an additional specific embodiment of the invention, a pharmaceutical composition effective in promoting the growth and survival of retinal neurons may provide a local therapeutic agent concentration of between about 10 ng/ml and 100 ng/ml.

In a preferred embodiment, an aqueous solution of therapeutic polypeptide, antibody or fragment thereof is administered by subcutaneous injection. Each dose may range from about 0.5 μg to about 50 μg per kilogram of body weight, or more preferably, from about 3 μg to about 30 μg per kilogram body weight.

The dosing schedule for subcutaneous administration may vary form once a week to daily depending on a number of clinical factors, including the type of disease, severity of disease, and the subject's sensitivity to the therapeutic agent.

D. Non-Therapeutic Uses for the Antibody Mutant

The antibody mutants of the invention may be used as affinity purification agents. In this process, the antibodies are immobilized on a solid phase such as Sephadex resin or filter paper, using methods well known in the art. The immobilized antibody mutant is contacted with a sample containing the antigen to be purified, and thereafter the support is washed with a suitable solvent that will remove substantially all the material in the sample except the antigen to be purified, which is bound to the immobilized antibody mutant. Finally, the support is washed with another suitable solvent, such as glycine buffer, pH 5.0, that will release the antigen from the antibody mutant.

The mutant antibodies may also be useful in diagnostic assays, e.g., for detecting expression of an antigen of interest in specific cells, tissues, or serum.

For diagnostic applications, the antibody mutant typically will be labeled with a detectable moiety. Numerous labels are available which can be generally grouped into the following categories:

(a) Radioisotopes, such as $^{36}S$, $^{14}C$, $^{125}I$, $^{3}I$, and $^{131}I$. The antibody mutant can be labeled with the radioisotope using the techniques described in *Current Protocols in Immunology*, vol 1–2, Coligen et al., Ed., Wiley-Interscience, New York, Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody mutant using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzym. (Ed. J. Langone & H. Van Vunakis), Academic press, New York, 73: 147–166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with p-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate-4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody mutant. The skilled artisan will be aware of various techniques for achieving this. For example, the antibody mutant can be conjugated with biotin and any of the three broad categories of labels mentioned above can be conjugated with avidin, or vice versa. Biotin binds selectively to avidin and thus, the label can be conjugated with the antibody mutant in this indirect manner. Alternatively, to achieve indirect conjugation of the label with the antibody mutant, the antibody mutant is conjugated with a small hapten (e.g. digloxin) and one of the different types of labels mentioned above is conjugated with an anti-hapten antibody mutant (e.g. anti-digloxin antibody). Thus, indirect conjugation of the label with the antibody mutant can be achieved.

In another embodiment of the invention, the antibody mutant need not be labeled, and the presence thereof can be detected using a labeled antibody which binds to the antibody mutant.

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147–158 (CRC Press, Inc. 1987).

Competitive binding assays rely on the ability of a labeled standard to compete with the test sample for binding with a limited amount of antibody mutant. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, each capable of binding to a different immunogenic portion, or epitope, or the protein to be detected. In a sandwich assay, the test sample to be analyzed is bound by a first antibody which is immobilized on a solid support, and thereafter a second antibody binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody mutant is labeled with a radionucleotide (such as $^{111}In$, $^{99}Tc$, $^{14}C$, $^{131}I$, $^{3}H$, $^{32}P$ or $^{35}S$) so that the tumor localized using immunoscintiography.

E. Diagnostic Kits

As a matter of convenience, the polypeptide or antibody of the present invention can be provided in a kit, i.e., packaged combination of reagents in predetermined amounts with instructions for performing the diagnostic assay. Where the antibody mutant is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. In Vivo Uses for the Polypeptide or Antibody

It is contemplated that the polypeptide or antibodies of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

The antibody or polypeptide is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody mutant is suitably administered by pulse infusion, particularly with declining doses of the antibody mutant. Preferably the dosing is given by injections, most preferably intravenous or subcutaneous injections, depending in part on whether the administration is brief or chronic.

For the prevention or treatment of disease, the appropriate dosage of the antibody or polypeptide will depend on the type of disease to be treated, the severity and course of the disease, whether the antibody mutant is administered for preventive or therapeutic purposes, previous therapy, the patient's clinical history and response to the antibody mutant, and the discretion of the attending physician. The anti-human IgE antibody is suitably administered to the patient at one time or over a series of treatments.

Depending on the type and severity of the disease, about 1 μg/kg to 150 mg/kg (e.g., 0.1–20 mg/kg) of antibody or polypeptide is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen for an anti-LFA-1 or anti-ICAM-1 antibody is disclosed in WO 94/04188.

The antibody mutant composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration; the scheduling of administration, and other factors known to medical practitioners. The "therapeutically effective amount" of the antibody mutant to be administered will be governed by such considerations, and is the minimum amount necessary to prevent, ameliorate, or treat a disease or disorder. The antibody mutant need not be, but is optionally formulated with one or more agents currently used to prevent or treat the disorder in question. The effective amount of such other agents depends on the amount of anti-human IgE present in the formulation, the type of disorder or treatment, and other factors discussed above. These are generally used in the same dosages and with administration routes as used hereinbefore or about from 1 to 99% of the heretofore employed dosages.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody mutant. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered by way of illustration and not by way of limitation.

EXAMPLES

Example I

Preparation of Monoclonal Antibodies to IgE

Eight monoclonal antibodies (MAE10–MAE17) with the ability to block the binding of IgE to FcεR1 were prepared. Monoclonal antibodies to IgE were prepared from the supernatants of U266B1 cells (ATCC TIB 196) using affinity chromatography on an isolated anti-IgE antibody (Genentech MAE1). For MAE12, five BALB/c female mice, age six weeks, were immunized in their foot pads with 10 μg of purified IgE in Ribi□s adjuvant. Subsequent injections were done in the same manner at one and three weeks after the initial immunizations. Three days after the final injection, the inguinal and popliteal lymph nodes were removed and pooled, and a single cell suspension was made by passing the tissue through steel gauze. The cells were fused at a 4:1 ratio with mouse myeloma P3X63-Ag8.653 (ATCC CRL 1580) in high glucose (DMEM) containing 50% w/v polyethylene glycol 4000. For MAE14, MAE15, and MAE13 the immunizations were done in a similar manner except that for MAE13, 30 μg of IgE per injection were used and IgE fragment 315–347 (Kabat) was assayed as a prefusion boost; For MAE10 and MAE11, injections were given subcutaneously in two doses of 100 μg and a final booster of 50 μg, and spleen cells were used for the fusions.

The fused cells were then plated at a density of $2\times10^5$ per well in 96 well tissue culture plates. After 24 hours HAT selective medium (hypoxanthine/aminopterin/thymidine, Sigma, #H0262) was added. Of 1440 wells plated, 365 contained growing cells after HAT selection.

Fifteen days after the fusion, supernatants were tested for the presence of antibodies specific for human IgE using an enzyme-linked immunosorbent assay (ELISA). The ELISA was performed as follows, with all incubations done at room temperature. Test plates (Nunc Immunoplate) were coated for 2 hours with rat anti-mouse IgG (Boehringer Mannheim, #605-500) at 1 μg/ml in 50 mM sodium carbonate buffer, pH 9.6, then blocked with 0.5% bovine serum albumin in phosphate buffered saline (PBS) for 30 minutes, then washed four times with PBS containing 0.05% Tween 20 (PBST). Test supernatants were added and incubated two hours with shaking, then washed four times with PBST. Human IgE (purified from U266 cells as described above) was added at 0.5 μg/ml and incubated for one hour with shaking, then washed four times in PBST. Horseradish peroxidase conjugated goat anti-human IgE (Kirkegarrd & Perry Labs, #14-10-04, 0.5 mg/ml) was added at a 1:2500 dilution and incubated for one hour, then washed four times with PBST. The plates were developed by adding 100 μl/well of a solution containing 10 mg of o-phenylenediamine dihydrochioride (Sigma, #P8287) and 10 μl of a 30% hydrogen peroxide solution in 25 ml phosphate citrate buffer, pH 5.0, and incubating for 15 minutes. The reaction was stopped by adding 100 μl/well of 2.5 M sulfuric acid. Data was obtained by reading the plates in an automated ELISA plate reader at an absorbance of 490 nm. For MAE12, 365 supernatants were tested and 100 were specific for human IgE. Similar frequencies of IgE specificity were obtained when screening for the other antibodies. All of the monoclonal antibodies described herein were of the IgG1 isotype except for MAE17, which was IgG2b, and MAE14, which was IgG2a.

Each of the IgE specific antibodies was further tested in cell-based and plate assays to select for antibodies which bound to IgE in such a way as to inhibit IgE binding to FcεRI and which are not capable of binding to FCEH-bound IgE. The results of these assays are set forth in Table 1 and Table 2 below.

TABLE 1

Summary of Murine Anti-HuIgE mAb Characteristics

| mAb | Immunogen | Schedule/ Dose (□g) | B-cell Source | Isotype | binding Fc□RI-bound IgE[1] | PBL histamine release[2] (EC50) | amount blocking FcεRI[3] (EC50) |
|---|---|---|---|---|---|---|---|
| MaE1 | PS IgE | 3 × 50 | lymph node | IgG1 | 0.05 μg/ml | 1 μg/ml | 0.3 μg |
| MaE10 | U266 IgE | 2 × 100, 1 × 50 | spleen | IgG1 | no binding at 10 μg/ml | >100 μg/ml | 2.5 μg |
| MaE11 | U266 IgE | 2 × 100, 1 × 50 | spleen | IgG1 | no binding at 10 μg/ml | >100 μg/ml | 0.6 μg |
| MaE12 | U266 IgE | 3 × 30 | lymph node | IgG1 | no binding at 10 μg/ml | >100 μg/ml | 0.8 μg |
| MaE13 | U266 IgE | 3 × 30 | lymph node | IgG1 | no binding at 10 μg/ml | >10 μg/ml | 0.6 μg |
| MaE14 | U266 IgE | 5 × 50 | lymph node | IgG2a | no binding at 10 μg/ml | >100 μg/ml | 2.5 μg |
| MaE15 | U266 IgE | 5 × 50 | lymph node | IgG1 | no binding at 10 μg/ml | >100 μg/ml | 0.6 μg |
| MaE16 | rHIgE aa315–547 | 5 × 1 | lymph node | IgG1 | no binding at 10 μg/ml | >100 μg/ml | 0.7 μg |

TABLE 1-continued

Summary of Murine Anti-HuIgE mAb Characteristics

| mAb | Immunogen | Schedule/ Dose (□g) | B-cell Source | Isotype | binding Fc□RI-bound IgE[1] | PBL histamine release[2] (EC50) | amount blocking FcεRI[3] (EC50) |
|---|---|---|---|---|---|---|---|
| MaE17 | rHIgE aa315–547 | 5 × 1 | lymph node | IgG2b | no binding at 10 μg/ml | >100 μg/ml | >5.0 μg |

TABLE 2

Summary of Murine Anti-HuIgE

| mAb | binding to membrane IgE on U266BL (EC50)[4] | binding of IgE on FceRII (CD23) IM9 (EC50)[5] | amount to block 1 μg IgE binding to FceRII (EC50)[6] | inhibition of invitro IgE synthesis[7] | affinity constant for IgE8 (Kd) |
|---|---|---|---|---|---|
| MaE1 | 0.4 μg/ml | 0.05 μg/ml | >100 μg | (−) | $5.4 \times 10^{-8}$ |
| MaE10 | 0.5 μg/ml | no binding at 10 μg/ml | 2.5 μg | (−) | $7 \times 10^{-9}$ |
| MaE11 | 0.15 μg/ml | no binding at 10 μg/ml | 0.6 μg | (+) | $3 \times 10^{-8}$ |
| MaE12 | >10 μg/ml | 1 μg/ml | 5.0 μg | (−) | $4 \times 10^{-7}$ |
| MaE13 | 1 μg/ml | no binding at 10 μg/ml | 0.7 μg/ml | (++) | $5 \times 10^{-8}$ |
| MaE14 | 6 μg/ml | no binding at 10 μg/ml | 2.5 μg/ml | (±) | $1.4 \times 10^{-8}$ |
| MaE15 | 6 μg/ml | no binding at 10 | 0.6 μg/ml | (±) | $7 \times 10^{-8}$ |
| MaE16 | 10 μg/ml | <0.05 μg/ml | 5 μg | (+) | ND |
| MaE17 | 10 μg/ml | no binding at 10 μg/ml | 5 μg | (++) | ND |

1. FACS based assays for analysis of murine anti-human IgE monoclonals. Screen of murine anti-human IgE monoclonal binding to IgE on CHO 3D10 (FcεRI alpha +).

a. CHO 3D10 cells (FceRI alpha chain stable transfectant, Hakimi et al., *J. Biol. Chem.* 25: 22079) at $5\times10^5$ cells per sample are incubated with U266 IgE standard (lot no. 13068-46) at 10 μg/ml in 100 μl FACS buffer (0.1% BSA, 10 mM sodium azide in PBS, pH 7.4) for 30 minutes at 4° C. followed by one wash with FACS buffer. The amount of IgE binding is determined by incubating an aliquot of IgE loaded cells with a polyclonal FITC conjugated rabbit anti-human IgG (Accurate Chem. Co. AXL-475F, lot no. 16) at 50 μg/ml for 30 minutes at 4° C. followed by three washes with FACS buffer.

b. IgE loaded cells are incubated with 100 μl of murine anti-human IgE hybridoma supernatant (murine IgG concentration ranging from 1 to 20 μg/ml) for 30 minutes at 4° C. followed by one wash with FACS buffer. A Genentech monoclonal anti-human IgE (MaE1) at 10 μg/ml is used as a positive control for binding. Genentech monoclonal (MAD 6P) which does not recognize IgE is used at 10 μg/ml as a negative control.

c. Monoclonal binding to human IgE on CHO cells is detected by incubating cells with 20 μg/ml FITC-conjugated, affinity purified $F(ab')_2$ goat anti-mouse IgG (Organon Teknica, #10711-0081) for 30 minutes at 4° C. followed by three washed with FACS buffer. Cells are added to 400 μl buffer containing 2 μg/ml propidium iodide (Sigma, #P4170) to stain dead cells.

d. Cells are analyzed on a Becton Dickinson FACSCAN flow cytometer. Forward light scatter and 90 degree side scatter gates are set to analyze a homogeneous population of cells. Dead cells which stain with propidium iodide are excluded from analysis. Hybridoma supernatants which do not bind IgE on CHO 3D10 cells were considered candidates for further screening.

2. Histamine release from peripheral blood basophils. Heparinized blood was obtained from normal donors and diluted 1:4 in a modified Tyrodes buffer (25 mM Tris, 150 mM NaCl, 10 mM $CaCl_2$, $MgCl_2$, 0.3 mg/ml HSA, pH 7.35) then incubated with 1 nM human IgE (ND) at 4° C. for 60 minutes. Cells were then added to Tyrodes buffer containing either the murine monoclonal anti-IgE Abs (10 mg/ml) or a polyclonal anti-human antiserum as the positive control, and incubated at 37° C. for 30 minutes. Cells were pelleted, histamine in supernatants was acetylated and histamine content was determined using an RIA kit (AMAC, Inc. Wesbrook, Main). Total histamine was determined from cells subjected to several rounds of freeze-thawing.

3. Blocking of Fitc conjugated IgE binding to FcεRI alpha chain. The effect of the antibodies on IgE binding was studied by preincubating Fitc labelled IgE with the various MaE antibodies at 37° C. for 30 minutes in PBS containing 0.1% BSA and 10 mM sodium azide pH 7.4, then incubating the complex with $5\times10^5$ 3D10 cells at 4° C. for 30 minutes. The cells were then washed three times and mean channel fluorescence at 475 nM was measured. A murine anti-human IgE mAb (Mae1) which does not block IgE binding to the FcεRI alpha chain was used as a control.

4. Analysis of murine anti-human IgE binding to membrane IgE positive B cell U266.

a. U266 B1 cells (membrane IgE+) are cultured in base medium supplemented with 15% head inactivated fetal calf serum (Hyclone, #A-1111-L), penicillin, streptomycin (100 units/ml) and L-glutamine (2 mM).

b. Cells ($5\times10^5$/aliquot) are incubated in 100 μl FACS buffer containing murine anti-human IgE monoclonals at 10, 5, 1, 0.5 and 0.1 μg/ml for 30 minutes on ice in 96 well round bottom microtiter plates followed by two washes with FACS buffer. The Genentech monoclonal MAE1is used as a positive control.

c. Cells are incubated in 100 μl FACS buffer containing 50 μg/ml (1:20 stock) FITC conjugated $F(ab')_2$ affinity purified goat anti-mouse IgE (Organon Teknika, #1711-0084) for 30 minutes on ice followed by three washes with FACS buffer. Cells are added to 400 μl FACS buffer containing propidium iodide at 2 μg/ml to stain dead cells.

5. FACS based binding assays to FceRII (CD23)+B cell IM9.

a. IM9 human B cell myeloma (ATCC CCL 159, *Ann. N.Y. Acad. Sci*. 190: 221–234 (1972) was maintained in GIF base medium with 10% heat inactivated fetal bovine serum, penicillin, streptomycin (100 units/ml) and L-glutamine (2 mM).

b. Cells ($5\times10^5$ aliquot) were incubated in 100 μl of FACS buffer containing U266 IgE standard at 2 μg/ml for 30 minutes at 4° C. in 96 well microtiter plates followed by 2 washes with FACS buffer. As a control, cells were incubated in buffer alone or buffer containing 2 μg/ml human IgG1 (Behring Diagnostics, cat. no. 400112, lot no. 801024).

c. The cells were then incubated with murine anti-human IgE monoclonals at 0.1 to 10 μg/ml for 30 minutes on ice. Genentech monoclonal MAE1was used as a positive control.

d. The cells were then incubated in 100 μl FACS buffer containing FITC conjugated $F(ab')_2$ goat anti-mouse IgG at 50 μg/ml (Organon Teknika, #1711-0084) for 30 minutes at 4° C. followed by 3 washes with FACS buffer.

e. The cells were then added to 400 μg buffer containing propidium iodide at 2 μg/ml to stain dead cells.

f. The cells were analyzed on a Becton Dickenson FACSCAN flow cytometer. Forward light scatter and 90 degree side scatter gates were set to analyze a homogeneous population of cells and dead cells which stained with propidium iodide were excluded from analysis. FITC positive cells (IgE binding) were analyzed relative to cells stained with FITC rabbit anti-human IgE alone.

g. As a positive control to determine the level of CD23 on the surface of IM9 cells in each experiment, an aliquot of cells was stained with Becton Dickinson murine monclonal Leu 20 (anti-CD23) at 10 μg/ml for 30 minutes at 4° C. followed by 2 washes. The cells were then incubated with FITC conjugated $F(ab')_2$ affinity purified goat anti-murine IgG at 50 μg/ml.

6. Antibody blocking of FITC conjugated IgE binding to the low affinity IgE receptor.

The binding of 40 nM FITC labelled IgE to the low affinity IgE receptor (CD23 or FcϵRI) expressed on the B lymphoblast cell IM-9 was analyzed by flow cytometry on a FACSCAN flow cytometer. The effect of the antibodies on FITC IgE binding was studied by preincubating FITC IgE with the murine anti-human antibodies at 0.1 to 10 μg/ml chimera at 37° C. for 30 minutes in PBS containing 0.1% BSA and 10 mM sodium azide pH 7.4, then incubating the complex with $5\times10^5$ cells at 4° C. for 30 minutes. The cells were then washed three times and mean channel fluorescence at 475 nM was measured. 7. IgE in vitro Assay Protocol a. Peripheral blood mononuclear cells were separated from normal donors.

b. Cells were washed extensively with PBS to remove as many platelets as possible.

c. Mononuclear cells were counted and resuspended in media at $1\times10^6$ cells/ml. The media was a mixture of DMEM with penicillin and streptomycin, 15% horse serum, IL-2 (25 U/ml) and IL-4 (20 ng/ml).

d. Antibodies were added at appropriate concentrations on day 0, 5 and 8.

e. Cultures were incubated in 24 well Falcon tissue culture plates for 14 days.

f. On day 14, supernatants were removed and assayed for IgE concentrations by an IgE specific ELISA protocol.

8. Affinity constant (kd) of murine mAb for human IgE was determined by equilibrium binding (Scatchard) analysis.

a. IgE (ND and PS allotypes were iodinated by the chloramine T method and separated from free $^{1251}$ Na with a PD10 sephadex G25 column (Pharmacia, #17-0851-01)) in RIA buffer: PBS, 0.5% bovine serum albumin (Sigma, #A-7888), 0.05% Tween 20 (Sigma, #P-1379), 0.01% thimerosol (Sigma, #T-5125), pH 7.4. Approximately 78–95% of the post column counts were precipitated with 50% trichloroacetic acid and specific activity of iodinated IgE preparations ranged from 1.6 to 13 μCi/μg assuming 70% counting efficiency.

b. A fixed concentration of $^{125}$I (approximately $5\times10^4$ cpm) was added to varying concentrations of unlabelled IgE (1 to 200 nM) in a final volume of 0.1 ml RIA buffer in 12×75 mm polypropylene test tubes. Murine anti-human IgE mAB's (20 mM final concentration) in 0.1 ml RIA buffer were then added for a final assay volume of 0.2 ml.

c. Samples were incubated 16–18 hours at 25° C. with continuous agitation.

d. Bound and free $^{125}$I IgE was separated by the addition of a 0.3 ml mixture of affinity purified goat anti-mouse IgG (Boehringer Mannheim, #605–208) coupled to CNBr activated Sepharose 4B (Pharmacia, #17-0430-01) and carrier protein A sepharose (Repligen, #IPA 300) in RIA buffer and incubated 1 to 2 hours at 25° C. with continuous agitation. RIA buffer (1 ml) was then added, and tubes were centrifuged 5 minutes at 400×g. Samples were then counted to determine total counts. The supernatants were aspirated with a finely drawn pasteur pipet, samples were recounted and bound versus free counts were calculated.

e. Scatchard analysis was performed utilizing a Fortran program (scanplot) based on the Ligand program written by P. Munson at NIH. Scatplot uses a mass action equation fitting bound as a function of total using the Rodbard type regression analysis.

Example 2

Preparation of Humanized MaE11

Introduction:

The following example describes various preparations of humanized MaE11 wherein residues were modified via site-directed mutagenesis to arrive at 12 anti-IgE MaE11 variants [F(ab)1–12]. The residues of F(ab)12 were used as the template to create rhuMaE25 or E25, a highly potent anti-IgE antibody described in Application PCT/US92/06860, filed Aug. 14, 1992.

Methods:

The murine anti-human IgE mAb MaE11, shown in FIG. 1, was modified by site-directed mutagenesis (Kunkel, T. A. (1985), *Proc. Natl. Acad. Sci. USA* 82: 488) from a deoxyuridine-containing template containing a human k-subgroup I light chain and human subgroup III heavy chain (VH-CH1) in a pUC 119-based plasmid, pAK2 (Carter et al. (1992), *Proc. Nati. Aca. Sci. USA* 89: 4285) to obtain the variant F(ab)-1. F(ab)-2 was constructed from the F(ab)-1 template and all other humanized F(ab) variants were constructed from a template of F(ab)-2. The plasmids were transformed into *E. coli* strain JM101 for the preparation of double- and single stranded DNA (Messing, J. (1979), *Recomb. DNA Tech. Bull.* 2: 43; Ausubel et al., *Current*

*Protocols in Molecular Biology*, Unit 1 (1997)). Both the light and heavy chain residues were completely sequenced using the dideoxynucleotide method. The DNA encoding light and heavy chains was then subeloned into a derivative of the *E. coli* F(ab) expression plasmid, pAK19 (Carter et al. (1992), *Biotechnology* 10: 163). The derivative lacked the hinge cysteines that form the inter chain disulfides in F(ab')$_2$ fragments. The F(ab) fragments, as opposed to full-length IgG antibodies, facilitated the analysis of a moderately large number of variants because *E. coli* expression could be used rather than mammalian cell culture techniques. These individual variants are described in application WO 93/04173 published 4 Mar. 1993. Once the best variant was determined, it was subsequently subcloned into a plasmid encoding a full-length human IgG1 (see below).

The expression plasmids were transformed into *E. coli* strain MM294 (Meselon, M and R. Yuan (1968), *Nature* 217: 1110), and a single colony was grown in 5 ml of 2YT media-carbenicillin (100 μg/ml) for 5–8 hours at 37° C. The culture (5 ml) was then added to 100 ml of AP5 media-carbenicillin (100 μg/ml) and allowed to grow for 16 hours in a 500 ml shaker flask at 37° C. The culture was centrifuged at 4,000×g and the supernatant removed. After freezing for 1 hour, the pellet was resuspended in 5 ml cold 10mM Tris, 1mM EDTA and 50 μl 0.1 M benzamidine (Sigma, St. Louis), the latter of which was added to inhibit proteolysis. After gentle shaking on ice for 1 hour, the sample was centrifuged at 10,000×g for 15 minutes. The supernatant was applied to a protein A-Sepharose CL-4B (Pharmacia) column (0.5 ml bed volume) then washed with a 10 ml solution of 3 M potassium chloride/100 mL Tris, pH 8.0, followed by elution with 100 mM acetic acid (2.5 ml), pH 2.8 into 1 M Tris, pH 8.0 (0.5 ml).

The F(ab) buffer was then exchanged into PBS using a Centricon-30 (Amicon) and concentrated to a final volume of 0.5 ml. SDS-PAGE gels of each F(ab) fragments were run in order to ascertain purity. The F(ab) concentrations were determined by using a 0.1% $\epsilon_{280}$ of 1.0. The extinction coefficient was determined by using the concentration of protein from an amino acid analysis of purified F(ab)-2 and the $A_{280}$ for this same sample.

Selected F(ab) fragments were analyzed directly by liquid chromatography/mass spectrometry to confirm their molecular weight. Samples were injected into a packed capillary liquid chromatography system (Henzel, W. J. et al. (1990), *Anal. Biochem*. 187: 228) and analyzed directly with a Sciex API 3 mass spectrometer. The higher charge states of human growth hormone (m.w. 22,256.2), acquired using the same instrument parameters as those used for the samples, were used for calibration.

For generation of full-length human IgG1 versions of humanized MaE11, the heavy and light chains were subcloned separately into previously described pRK plasmids (Gorman, C. M. et al. (1990), *DNA Protein Eng. Tech*. 2: 3). Appropriate heavy and light chain plasmids (depending upon the sequence change(s) desired) were cotransfected into an adenovirus-transformed human embryonic kidney cell line, known as 293 (Graham, F. L. et al. (1977), *J. Gen. Virol*. 36: 59), using a high efficiency procedure (Graham et al., supra & Gorman, C. M., *Science* 221: 551). Media was changed to serum free and harvested daily for up to 5 days. Antibodies were purified from the pooled supernatants using protein A-Sepharose CL-4B (Pharmacia). The eluted antibody was buffer exchanged into PBS by G25 gel filtration, concentrated by ultrafiltration using a Centriprep-30 or Centricon-100 (Millipore), and stored at 4° C. The concentration of antibody was determined using total IgG-binding ELISA. The results are described in Table 4.

Soluble Receptor Assay:

A 96-well assay plate (Nunc) was coated with 0.05 ml of the FcεRI α-chain IgG chimeric receptor in coating buffer (50 mM carbonate, bicarbonate, pH 9.6) for 12 hours at 4–8° C. The wells were aspirated and 250 μl blocking buffer (PBS, 1% BSA, pH 7.2) was added and incubated at 1 hour at 4° C. In a separate assay plate the samples and reference murine MaE11 were titered from 200 to 0.001 μg/ml by 1:4 dilutions with assay buffer (0.5% BSA and 0.05% Tween 20, PBS, pH 7.2) and an equal volume of 10 ng/ml biotinylated IgE (O-Shannessy, D. J. et al. (1984), *Immunol. Let*. 8: 273) was added followed by incubation of the plate for 2–3 hours at 25° C. The FcεRI-coated wells were washed three times with PBS and 0.05% Tween 20 (Sigma) and 50 μl from the sample wells were transferred and incubated with agitation for 30 minutes at 25° C. A solution of Streptavidin-HRP (500 μg/ml, Sigma), diluted to 1:5000 in assay buffer, was added at 50 μl/well followed by incubation of the plate for 15 minutes with agitation, and washing as described previously. Fifty μl/well of Microwell Peroxidase Substrate (Kirkgaard & Perry Laboratories) was added and the color was developed for 30 minutes. The reaction was stopped by adding an equal volume of 1 N HC1, and the absorbance measured at 450 nm. The concentration at 50% inhibition was calculated by plotting percentage of inhibition versus concentration of blocking antibody with a nonlinear four-parameter curve fit using the Kaleidagraph data analysis application (Synergy Software). The results are reported in Table 3.

FAGS-Based Binding Assays:

The ability of the antibody to inhibit FITC-conjugated (Goding, J. W. (1976), *J. Immunol. Methods* 13: 215) IgE binding to the α-chain of the high-affinity FcεRI receptor expressed on CHO 3D10 cells (Hakimi, J. et al. (1990), *J. Biol Chem*. 265: 22079) was determined by flow cytometry. FITC-conjugated IgE (40 nM) was preincubated with the antibody ($0.3–1.0\times10^{-6}$ M) at 37° C. for 30 minutes in FAGS buffer (PBS, 0.1% BSA, and 10 mM sodium azide, pH 7.4). The complex was then incubated with $5\times10^5$ CHO CD10 cells at 4° C. for 30 minutes. The cells were washed three times with FAGS buffer and mean channel fluorescence at 475 nm measured on a FACScan flow cytometer (Becton Dickinson). MaE1, a murine anti-human IgE mAb that does not block IgE binding to the FceRI a-chain, was used as a positive control and MOPC21 (Cappel), a murine monoclonal that does not recognize IgE, was used as a negative control. The results are described in FIG. 3.

Binding of Antibodies to IgE-loaded FcεRI:

Antibody binding to human IgE associated with the α-subunit of FceRI expressed on CHO 3D10 cells with 10 μg/ml human IgE for 30 minutes at 4° C. Cells were washed three times followed by a 30 minute incubation with varying concentrations of either murine anti-human IgE mAbs MaE1 or MaE11 or the humanized mAb variant 12 [F(ab)12]. MOPC21 (murine IgG1) was used as a control for the murine mAbs, whereas humanized 4D5 mAb (Carter et al., *Proc. Natl. Acad. Sci. USA* 89: 4285 (1992), human IgG1) was used as a control for F(ab)12. Binding of murine mAbs was detected with a FITC-conjugated F(ab')$_2$ goat anti-mouse IgE (10 μg/ml). Humanized mAb binding was detected with a FITC-conjugated F(ab')$_2$ goat anti-human IgG (50 μg/ml), which had been affinity purified on an IgE column to minimize cross-reactivity to IgE. The results are described in FIG. 4.

Computer Graphics Models of Murine and Humanized F(ab)'s:

The sequences of F(ab) VL and VH domains of FIG. 1 were used to construct a computer graphics model of the murine MaE11 VL-VH domains. This model was subsequently used to determine which framework residues should be incorporated into the humanized antibody which resulted in the creation of F(ab)-2. Models of the humanized variants were also constructed to verify correct selection of murine framework residues. Construction of the models was performed as described in Carter et al. (1992), *Proc. Natl. Acad. Sci. USA* 89: 4285; Eigenbrot, C. et al. (1993), *J. Mol Biol.* 229: 969.

Results:

Design of Humanized MaE11 Antibodies:

The present study of humanized antibodies used a human consensus sequence. This is in contrast to other humanization techniques that have used human sequences closest to the murine Ig of interest. Shearman, C. W. et al. (1991), *J. Immunol.* 147: 4366; Kettleborough, C. A. et al. (1991), *Protein Eng.* 4: 773; Tempest, P. R. et al. (1991), *Biotechnology* 9: 266; Co, M. S. et al. (1991), *Proc. Natl. Acad. Sci. USA* 88: 2869; Routledge, E. G. (1991), *Eur. J. Immunol.* 21: 2717. This human consensus sequence consisted of a framework based on human VH subgroup III and VLκ subgroup I as defined in Kabat et al. (1991), *Sequences of Proteins of Immunological Interest*, 5 ed., National Institute of Health, Bethesda, MD. F(ab)-1 was created by grafting the six CDR's, as defined by Kabat, supra, onto a human IgG1 framework. All framework residues were retained as human. This variant would best be described as a straight "CDR swap." F(ab)-1 showed no detectable, inhibition of IgE binding to the receptor (Table 3). The failure of such "CDR swap" variants to bind their antigens has been reported previously. Carter et al., supra; Tempest et al., supra. Note that the exact sequence of F(ab)-1 is not described in Table 3, however, this sequence can be inferred by substituted MaE11 murine Kabat CDR residues (indicated in brackets) for corresponding human residues. FIG. 1 indicates Kabat CDRs by right-hand and left-hand brackets, while Chothia CDRs are indicated by underline.

In order to assist in interpretation and reduce confusion, human residues are written in normal type, while murine residues appear in italics. Where residue substitutions are indicated, the first residue is the one being replaced, the second the one being inserted, and the number the Kabat designation of the native sequence.

The F(ab)-2 variant was based on molecular modeling. In this molecule, several murine framework residues were incorporated into the human framework. In F(ab)-2, the definition of CDR's provided by Kabat et al., supra (which are based on interspecial sequence variability) were used except for CDR-H1 and CDR-H2.

CDR-H1 definitions based on sequence variability (Kabat et al., supra) between one based on crystallographic studies of antigen-antibody complexes (Chothia, C. et al. (1989), *Nature* 342: 877) differ significantly (FIG. 1). Therefore, CDR-H1 was redefined to include both definitions, i.e., human residues 26-35.

The definition of CDR-H2 based on sequence variability (Kabat et al.) contains more residues than the one based on antibody-antigen crystal structures (Chothia et al.) [see FIG. 1: Kabat CDR's are defined by brackets, Chothia by underline]. Because no crystal structure was discovered which indicated antibody-antigen contacts for antibody human residues 60–65, CDR-H2 was modified to include a hybrid of both definitions, i.e., human residues 50–58. As a result, in F(ab)-2 a shorter version of CDR-H2 was used as compared with F(ab)-1.

As a result, F(ab)-2 was created with the minimal amount of changes from human to murine residues which were believed to be required for maintenance of binding. An additional 10 variants were created in order to test the effects of buried residues on CDR conformations, as well as to evaluate the predictive effects of molecular modeling of significant framework residues and examine other interesting residues.

To test the effects of buried residues on CDR conformation, F(ab)-3 to F(ab)-7 were constructed in which murine residues were changed back to human ones. As is indicated in Table 4 (by F(ab)-3 & F(ab)-4), the side chains at VL4 and VL33 have minimal effect on binding and presumably the conformation of CDR-L1 in the humanized antibody.

Modeling suggested that framework residue VH 24 might affect the CDR-L1 conformation and VH 37 could affect the VL-VH interface. However, substitution of the human residue into at VH 24 [F(ab)-5] or VH37 [F(ab)-7] showed minimal reduction in binding. In contract, replacement of the murine Phe at framework position VH 78 with human Leu [F(ab)-6] caused a significant reduction in binding. The models suggest that this residue is influencing the conformation of CDR-H1 and/or CDR-H2.

F(ab)-9 to F(ab)-12 examined the replacement of human residues with murine. All four of these variants exhibited substantial improvement in binding compared with F(ab)-2 (See tables 3,4 and FIG. 3). In F(ab)-9, which exhibited five-fold improved binding over F(ab)-2, two residues in CDR-H2 (as defined by Kabat et al, supra) were changed to murine residues: Ala VH 60 Asn and Asp H61 Pro. The Pro substitution could have altered the CDR-H2 conformation and/or rigidity and Asn H60 is anticipated to be buried at the VL-VH interface, possible interacting with Asp VL1.

F(ab)-10, which displayed substantially improved binding relative to F(ab)-2, was a variant in which all buried residues (defined as residues with accessible surface area being less than 5% of that of the free amino acid) in both the VL and VH domains were those of murine MaE11. In essence, F(ab)-10 can be thought of as murine MaE11 in which only exposed, non-CDR residues in VL and VH were changed to human residues.

To determine whether the improved binding of F(ab)-10 was due to one or a few residues, variants F(ab)-11 and F(ab)-12 were created. Instead of F(ab)-2, F(ab)-9 was used as the base template from which to prepare these variants because it exhibited a fivefold improved binding. Modelling suggested that sidechains at VH 63 and VH67 could affect the conformation of CDR-H2. VH 63 is considered part of CHR-H2 as defined by Kabat et al., supra, but not as defined by Chothia et al., supra. VH 67 is considered a framework residue in both definitions. In F(ab)-11, VH 63 and VH 67 were the murine residues Leu and Ile, respectively. In F(ab)-12, only VH 67 was changed to murine Ile.

In both the soluble receptor (Table 4) and cell based assays (Table 4, FIG. 3), both of the variants F(ab)-11 and F(ab)-12 exhibited binding that was at least as good as F(ab)-10, and better than F(ab)-9. This suggests that the improved binding of F(ab)-10 was not due to repacking of the VH domain interior with murine residues, but was due to the effect of only a single residue, i.e. VH 67.

F(ab)-8 was constructed replacing human VL 55 residue Glu with murine Gly as well as well as similar substitutions at VL 57 of Gly for Glu. F(ab)-2 used the human residues, while F(ab)-8 substituted the murine residues at these positions. As can be quickly surmised from Table 3, the substitution of these residues had no impact upon receptor binding.

TABLE 3

| Humanized Mae11 Variants | | | | | |
|---|---|---|---|---|---|
| | Changes from F(ab)-2[a] | | Concentration at 50% inh. (ng/ml) mean, | F(ab)-X | F(ab)-X |
| Variant | VL | VH | std. dev.[b] | F(ab)-2 | MaE11 |
| F(ab)-1 | *Leu* 4 Met<br>Arg 24 *Lys*<br>Glu 55 *Gly*<br>Gly 57 *Glu* | *Val* 24 Ala<br>*Ile* 37 Val<br>Thr 57 *Ser*<br>Ala 60 *Asn*<br>Val 63 *Leu*<br>Gly 65 *Asn*<br>*Phe* 78 Leu | >100,000 | >16.0[c] | >560 |
| F(ab)-2 | — | — | 6083, 1279 | 1.0 | 34 |
| F(ab)-3 | *Leu* 4 Met<br>*Met* 33 Leu | — | 9439, 508 | 1.6 | 53 |
| F(ab)-4 | *Leu* 4 Met | — | 6770, 349 | 1.1 | 3.8 |
| F(ab)-5 | — | *Val* 24 Ala | 9387, 733 | 1.6 | 52 |
| F(ab)-6 | — | *Phe* 78 Leu | 17,537, 4372 | 2.9 | 24 |
| F(ab)-7 | — | *Ile* 37 Val | 8622, 107 | 1.4 | 48 |
| F(ab)-8 | Glu 55 *Gly*<br>Gly 57 *Glu* | — | 5799, 523 | 1.0 | 32 |
| F(ab)-9 | — | Ala 60 *Asn*<br>Asp 61 *Pro* | 1224, 102 | 0.20 | 6.8 |
| F(ab)-10 | Ala 13 *Val*<br>Val 19 *Ala*<br>Val 58 *Ile*<br>Leu 78 *Val*<br>Val 104 *Leu* | Val 48 *Met*<br>Ala 49 *Gly*<br>Ala 60 *Asn*<br>Val 63 *Leu*<br>Phe 67 *Ile*<br>Ile 69 *Val*<br>Met 82 *Leu*<br>Leu 82c *Ala* | 842, 130 | 0.14 | 4.7 |
| F(ab)-11 | — | Ala 60 *Asn*<br>Asp 61 *Pro*<br>Val 63 *Leu*<br>Phe 67 *Ile* | 416, 66 | 0.07 | 2.3 |
| F(ab)-12 | — | Ala 60 Asn<br>Asp 61 Pro<br>Phe 67 Ile | 501, 84 | 0.08 | 2.8 |
| MaE11 | — | — | 179, 63 | 0.03 | 1.0 |

[a]Murine residues are italicized; residue numbers are according to Kabat et al.
[b]Mean and standard deviation of three soluble receptor assays
[c]A F(ab)X/F(ab)-2 ratio >16 means that this variant exhibited no binding even at the highest F(ab) concentrations used The F(ab) variants determined to have binding closest to murine MaE11, namely F(ab)-2, F(ab)-9, F(ab)-10 and F(ab)-12 were used to generate full-length IgG1 molecules. The binding of these molecules relative to variant F(ab)-2 or MaE11 was comparable to the binding exhibited by the F(ab) fragments. These results are reported in Table 4.

TABLE 4

| Humanized MaE11 IgG1 variants | | | |
|---|---|---|---|
| Full length variant | Concentration at 50% inh. (ng/ml) mean, std. dev.[a] | VariantX IgG1-2[b] | VariantX MaE11 |
| IgG1-2 | 7569, 1042 | 1.0 | 16.9 |
| IgG1-9 | 3493, 1264 | 0.46 | 7.8 |
| IgG1-10 | 1118, 172 | 0.15 | 2.5 |
| IgG1-12 | 1449, 226 | 0.19 | 3.2 |
| MaE11 | 449, 53 | 0.06 | 1.0 |

Binding of MaE11 to IgE-loaded FcεRI:

Murine MaE11 prevents binding of free IgE to FcεRI on mast cells but does not trigger histamine release by binding to IgE-loaded FcεRI. As shown in FIG. 4, both murine MaE11 and humanized variant 12 (IgG1-12) as well as the negative isotype control antibody MOPC21 and the negative isotype control humanized 4D5 (Carter et al., supra) did not bind IgE-loaded FcεRI on CRO3D10 cells. In contrast, the murine MaE1 antibody, which binds to IgE but does not prevent IgE binding to FcεRI, bound to the IgE-loaded FcεRI. Unlike the human IgG1 control (humanized 4D5), the murine IgG1 isotype (as represented by MOPC21) exhibits a nonspecific background binding of approximately 10% on these cells. MaE11 did not give staining above the MOPC21 control and humanized variant 12 did not give staining above the humanized 4D5 control (FIG. 4).

Partial Alanine Scanning of CDR Residues Important in IgE Binding:

The sequences of the MaE11 CDR's indicate a preponderance of charged residues (FIG. 1). CDR-L1 contains three Asp residues, whereas CDR-L3 possesses His, Glu and Asp. CDR-H3 has three His residues. The models of murine and humanized MaE11 illustrated the spatial proximity of the all of these charged residues (not shown). In contrast, the lone Asp 54 in CDR-H2 is spatially separated from the other charged residues. Alanine was substituted, by site-directed mutagenesis (Kunkel, T. A. (1985), *Proc. Natl. Acad. Sci. USA* 82: 488), for each of these charged residues to generate variants. In CDR-L1, alteration of one of the three Asp residues, Asp VL32b, effectively abolished IgE binding [F(ab)-16; Table 5], whereas substitution of the other Asp residues had minimal effect [F(ab)-14; F(ab)-15]. Simultaneous alteration of Glu VL93 and Asp VL94 to alanine in CDR-L3 [Fa(ab)-17; Table 5, also reduced binding, although not to the same extent as did replacement at VL32b. Individual substitution of the three His residues in CDR-H3 with Ala resulted in either slightly improved binding [F(ab)-21] or a three-fold reduction in binding [F(ab)-20 & F(ab)-22]. However, simultaneous alteration of all three His residues abolished binding [F(ab)-19]. Although it is not readily determinable whether the charged residues are involved in direct binding to IgE or to provide some conformational stability to their respective CDR's, variants F(ab)-13 to F(ab)-22 show that CDR-L1 and CDR-H3 are important determinants in IgE binding.

TABLE 5

| Humanized Mae11 F(ab) CDR Residue Variants | | | | |
|---|---|---|---|---|
| | Changes from F(ab)-2[(a)] | | Concentration at 50% inh. (ng/ml) | F(ab)-X |
| Variant | VL | VH | mean, std dev. [(b)] | F(ab)-2 |
| F(ab)-2 | — | — | 6083, 1279 | 1.0 |
| F(ab)-13 | *Asp 30* Ala *Asp* 32 Ala *Asp* 32b Ala | — | >100,000 | >16.0[(c)] |
| F(ab)-14 | *Asp* 30 Ala | — | 3452, 183 | 0.57 |
| F(ab)-15 | *Asp* 32 Ala | — | 6384, 367 | 1.0 |
| F(ab)-16 | Asp 32b Ala | — | >100,000 | >16.0 |
| F(ab)-17 | Glu 93 Ala Asp 94 Ala | — | 17,456, 7115 | 2.9 |
| F(ab)-18 | — | *Asp* 54 Ala | 2066, 174 | 0.34 |
| F(ab)-19 | — | His 97 Ala His 100a Ala His 100c Ala | >100,000 | >16.0 |
| F(ab)-20 | — | His 97 Ala | 19,427, 8360 | 3.2 |
| F(ab)-21 | — | His 100a Ala | 2713, 174 | 0.45 |
| F(ab)-22 | — | His 100c Ala | 15,846, 8128 | 2.6 |

[(a)]Murine residues are italicized; residue numbers are according to Kabat et al.
[(b)]Mean and standard deviation of three soluble receptor assays
[(c)]A F(ab)X/F(ab)-2 ratio >16 means that this variant exhibited no binding even at the highest F(ab) concentrations used

SUMMARY AND CONCLUSION

The creation of a functional, humanized murine anti-IgE antibody from MaE11 involves the substitution of several murine framework residues into the human framework. In addition, mapping of the charged CDR residues indicated that some of these are important in the antibody-IgE interaction.

In agreement with previous studies (Carter et al., supra; Shearman, C. W. et al. (1991), *J. Immunol*. 147: 4366; Kettleborough, C. A. et al (1991), *Protein Eng*. 4: 773; Tempest, P. R. (1991), *Biotechnology* 9: 266), variants F(ab)-1 to F(ab)-12 indicate that framework residues can have a significant effect on antibody function. This is particularly emphasized when considering F(ab)-1, which is a straight CDR swap in which only the six murine CDR's were transplanted onto the human framework residues. A potential explanation for this involves CDR-H2. The buried hydrophobic residues at positions VH63 and VH67 could affect the conformation of CDR-H2. Variants were created containing four combinations at positions VH63 and H67, i.e., murine Leu and Ile, respectively [MaE11 and F(ab)-11], Val and Phe [F(ab)-2], Leu and Phe [F(ab)-l], and Val and Ile [F(ab)-12]. The clear inference from the binding data of these four variants indicates that the important residue is VH67, which must be the murine Ile in order to provide affinity comparable to murine MaE11. In F(ab)-1, this residue was the human Phe.

Of the 12 residues in F(ab)-1 retained as human [compared with F(ab)-2], 8 were separately changed to murine in other variants. Three changes had no effect on binding: VL4 [F(ab)-4]; VL55 and VL 57 [F(ab)-8]Two residue substitutions: VH60 and VH 61 [F(ab)-9], improved binding, whereas three reduced binding: VH24 [F(ab)-5]; VH37 [F(ab)-7] and VH78 [F(ab)-6].

The variant F(ab)-10 was designed with the hypothesis suggested by Padlan (Padlan, E. A. (1991), *Mol Immunol*. 28: 489), who proposed that murine antibody immunogenicity can be reduced by changing only exposed framework residues. In this variant, the hydrophobic interior of both the VL and VH domains, in other words, the variant was the murine MaE11 in which only exposed framework residues in VL and VH were changed to the human sequence. Although F(ab)-10 exhibited binding close to that of the murine MaE11, a change in a single amino acid domain, VH67 from human to murine effected the same improvement in binding [F(ab)-12, IgG1-12].

The humanized variant exhibiting binding comparable to murine MaE11, which also required the fewest changes, was F(ab)-12. This variant replaced only 5 human framework residues with murine (VL4, VH24, VH37, VH67 and VH78. Four of these residues were determined by molecular modeling. The fifth, VH67, as well as the CDR-H2 residues VH60 and VH61, were included by using the molecular models in an effort to improve the binding of the initial variant F(ab)-2.

Example 3

Histamine Release Assay

Introduction:

This is a rat mast cell histamine assay (RMCHA) which measures quantitatively the biological activity of a recombinant humanized, monoclonal anti-IgE antibody based on the ability of the antibody to block histamine release from allergen-sensitized RBL 48 cells. Furthermore, this determination is made under physiological conditions similar to those of the human body. The RBL 48 cell line was derived from the parental rat mast cell line RBL 2H3 which has been subsequently transfected with the α-subunit of the high affinity human IgE receptor (FcεRI). Gilfillan A. M. et al., *J. Immunol*. 149(7): 2445–2451 (1992).

Methods:

RBL 48 cells (Gilfillan et al., supra) are grown in sIMDM, Iscove's modified Dulbecco's media supplemented with 10% fetal calf serum, 2 mM glutamine, and 500 μg/ml of active geneticin (Gibco, #860-1811) in a T175 tissue culture flask (Falcon #3028) at 37° C. in a humidified 5% $CO_2$ incubator (Fischer, model #610). The cells were harvested by exposure to 4 mL solution of PBS/0.05% trypsin/0.53 mM EDTA for 2 minutes at 37° C. followed by centrifugation (400×g, 10 min.) and resuspension in fresh sIMDM. The cells in suspension were counted with a hemocytometer (Reichert-Jung) and the density was adjusted to $0.4\times10^6$ cells/ml. The cells were then seeded at 100 μl/well (40,000 cells per well) in the inner 60 wells of a 96-well, U-shaped tissue culture plate (Linbro) and cultured for 24 hours at 37° C. in the humidified 5% $CO_2$ incubator. After being washed once with 200 μl/well of sIMDM (via aspiration), the cells were preincubated for 30 minutes with 90 μl/well of a solution of assay diluent (sIMDM, 3 U/ml Na-heparin) with ragweed-specific IgE (RSIgE, 10 ng/ml, 23.48 ng/ml total IgE, 1.43% ragweed-specific human plasma, North American Biological, lot #42-365054).

After the preincubation period, 10 μl/well of either anti-IgE antibody (diluted in assay diluent, 0.06–39.4 μg/ml) or assay diluent (for total histamine release, background, and ragweed controls) were added to the cells, and the plate was incubated for 24 hours in 5% $CO_2$ at 37° C. in the incubator. After the incubation, the cells were aspirated and washed 3× with 200 μl/well sIMDM. Following the washing, the cells were incubated with 100 l/well of either (1) 0.5% triton solution (for total histamine release), (2) histamine release buffer (HRB, 50% $D_2O$, 0.8% NaCl, 1.3 mM $CaCl_2$, sIMDM, or (3) ragweed antigen (NIH #A-601-903A-185, 0.1 μg/ml in HRB) at 37° C. for 30 minutes and the reaction was stopped by placement on ice. (100% $D_2O$=100% $D_2O$, 0.8% NaCl, 1.3 mM $CaCl_2$).

The plate was centrifuged for 5 minutes at 900×g (2460 rpm) at 4° C., and the supernatants were harvested and diluted 1/80 in PBS (1/1000 in PBS for total histamine release control) for histamine determination using the Histamine Enzyme Immunoassay Kit (Immunotech #1153). The supernatants (100 μl/well) were transferred to acylation tubes containing acylation powder (per kit) and reacted with 50 μl acylation buffer (per kit) for 30 minutes at ambient temperature. The acylated histamine (50 μl/well) was then transferred to a conjugation plate (per kit) and incubated with 200 μl/well of histamine-acetylcholinesterase conjugate (per kit) for 18 hours at 4° C.

After this incubation, the wells were blotted and rinsed to remove unbound conjugate by washing 4× with 300 μl/well of washing buffer (Immunotech kit, #1153). The chromatogenic substrate (acetylthiocholine, dithionitrobenzoate, 200 l/well, per kit) was added and incubated in the dark at ambient temperature for 30 minutes. The reaction was stopped by the addition of stop solution (50 μl/well, per kit) and the absorbance at 405 nm with a 620 nm reference was determined on a SLT 340 ATTC plate reader. The intensity of absorbance is inversely proportional to the histamine concentration (expressed as nM) which is determined from the histamine standard curve (from the enzyme immunoassay kit, AMAC). The percent total histamine release was calculated from data of histamine concentration and the percent inhibition was calculated by 100%-total histamine release. The results are indicated in FIG. 5.

Summary and Conclusion:

The graph of molar ratio anti-IgE vs. percent inhibition of ragweed-induced histamine release indicates that the F(ab) form of e26 antibody has superior ragweed-induced histamine release properties than the F(ab) form of e25 antibody. E26 inhibits ragweed-induced histamine release in a dose dependent manner with a half-maximal inhibition molar ratio of 44:1 (anti-IgE:RSIgE). In contrast, e25 only inhibits ragweed-induced histamine release at a very high molar ratio (between 200:1 to 1550:1 anti-igE:RSIgE). The half-maximal inhibition molar ratio for the e25 curve could be estimated to be between 400:1 to 500:1. Therefore, based on the half-maximal inhibition molar ratio data, which is a measure of the binding affinity of a molecule, the e26 molecule binds to RSIgE approximately 10-times better than the e25 molecule.

Example 4

Phage Display Example

Introduction:

This example describes specific affinity-improved anti-IgE antibodies generated through monovalent phage display and selection of F(ab) fragments derived from the E25 humanized anti-IgE antibody (Presta et al., *J. Immunol.* 151: 2623 (1993).

Methods:

I. Construction of Monovalent F(ab)-phage Libraries

Several F(ab) libraries were constructed. As a starting vector, an e25 variant containing the VL substitution D32E (to eliminate IsoAsp isomerization) was fused to the C-terminal domain of bacteriophage M13g3p by known techniques, see for example Bass et al., *Proteins* 8: 309 (1990). This plasmid, which was known as p426 appears in FIG. 10. First, the "wild-type" F(ab)-phage, p426 was used as the template for construction of library-specific "stop" templates. By introducing stop codons (TAA or TGA), the original molecule is rendered inactive, thereby reducing background effects and template-specific (hybridization) bias in the mutagenesis steps for constructing the library (Lowman & Wells, *Methods: Comp. Methods Enzymol.* 3: 205 (1991)). These templates were constructed using single-stranded template-directed mutagenesis (Kunkel et al., *Methods Enzymol.* 204: 125 (1991)), with the oligonucleotides listed in Table 10.

Subsequently, these stop-templates were used in a second round of mutagenesis, using the oligos listed in Table 11, to generate libraries in each of the indicated CDR regions. NNS degenerate codons were used to yield all twenty amino acids in each of the indicated CDR regions. (Nucleotide bases are indicated in single-letter IUPAC nomenclature; N=A, G, C or T; S=G or C). NNS degenerate codons were used to yield all twenty amino acids at each randomized positions, using 32 different possible codons. An amber stop codon (TAG) encodes Gln in the suppressor system used here; i.e., the supE suppressor strain XL-1 Blue; Bullock et al. *Biotechniques* 5, 376 (1987). The presence of an amber codon between the heavy-chain antibody domain and the g3p domain on phage permits the expression of the phage-displayed fusion protein only in amber suppressor strains of *E. coli*, while soluble F(ab) protein can be obtained with this same construct in non-suppressor strains of *E. coli*. (Lowman et al. *Biochemistry* 30: 10832 (1991); Lowman and Wells, *Methods Comp. Methods. Enzymol.* 3: 205 (1991); Hoogenboom et al., *Nucl. Acids Res.* 19: 4133 (1991). However, other stop codons for use in other *E. coli* phage expression systems are apparent to those of ordinary skill in the art.

The products of the random mutagenesis reaction were transformed into *E. coli* cells (Stratagene, XL-1 Blue) by electroporation and amplified by growing overnight at 37° C. with M13K07 helper phage (Vierra and Messing, *Methods Enzymol.* 153: (1987)).

TABLE 10

Stop-Template Oligos for First-Round Mutagenesis

| Oligo sequence no. | Region | Sequence | |
|---|---|---|---|
| HL-208 | VL1 | ACC TGC CGT GCC AGT TAA TAA GTC TAA TAA GAA GGT GAT AGC TAC | (SEQ ID NO:27) |
| HL-209 | VH3 | GCC AGT CAG AGC GTC TAA TAA TAA GGT TGA AGC TAC CTG AAC TGG T | (SEQ ID NO:28) |
| HL-210 | VH3 | TGT GCT CGA GGC AGC TAA TAA TAA GGT TAA TGG TAA TTC GCC GTG TGG GG | (SEQ ID NO:29) |

TABLE 10-continued

Stop-Template Oligos for First-Round Mutagenesis

| Oligo sequence no. | Region | Sequence | |
|---|---|---|---|
| HL-220 | VL2 | G AAA CTA CTG ATT TAC TAA TAA TAA TAA CTG GAG TCT GGA GTC | (SEQ ID NO:30) |
| HL-221 | VL3 | CT TAT TAC TGT CAG CAA AGT TAA TAA TAA CCG TAA ACA TTT GGA CAG GGT ACC | (SEQ ID NO:31) |
| HL-222 | VH1 | G TCC TGT GCA GTT TCT TAA TAA TAA TAA TAA TCC GGA TAC AGC TGG | (SEQ ID NO:32) |
| HL-223 | VH1 | GCC TAC TCC ATC ACC TAA TAA TAA AGC TGA AAC TGG ATC CGT CAG | (SEQ ID NO:33) |
| HL-224 | VH2 | GG GTT GCA TCG ATT TAA TAA TAA GGA TAA ACT TAA TAT AAC CCT AGC CTC AAG | (SEQ ID NO:34) |
| HL-225 | VL1 | AAG CCG GTC GAC AGG TAA TAA GAT TAA TAC TAA AAC TGG TAT CAA CAG | (SEQ ID NO:35) |

TABLE 11

Library-Specific, Degenerate Oligos for Second Round Mutagenesis

| | | | |
|---|---|---|---|
| HL-212 | VL1 | ACC TGC CGT GCC AGT NNS NNS GTC NNS NNS GAA GGT GAT AGC TAC | (SEQ ID NO:36) |
| HL-213 | VH3 | GCC AGT CAG AGC GTC NNS NNS NSS GGT NNS AGC TAC CTG AAC TGG | (SEQ ID NO:37) |
| HL-214 | VH3 | TGT GCT CGA GGC AGC NNS NNS NNS GGT NNS TGG NNS TTC GGC GTG TGG GG | (SEQ ID NO:38) |
| HL-231 | VL2 | G AAA CTA CTG ATT TAC NNS NNS NNS NNS CTG GAG TCT GGA GTC | (SEQ ID NO:39) |
| HL-232 | VL3 | CT TAT TAC TGT CAG CAA AGT NNS NNS NNS CCG NNS ACA TTT GGA CAG GGT ACC | (SEQ ID NO:40) |
| HL-233 | VH1 | G TCC TGT GCA GTT TCT NNS NNS NNS NNS NNS TCC GGA TAC AGC TGG | (SEQ ID NO:41) |
| HL-234 | VH1 | GTT TCT GGC TAC TCC ATC ACC NNS NNS NNS AGC NNS AAC TGG ATC CGT CAG | (SEQ ID NO:42) |
| HL-235 | VH1 | GG GTT GCA TCG ATT NNS NNS NNS GGA NNS ACT NNS TAT AAC CCT AGC GTC AAG | (SEQ ID NO:43) |
| HL-236 | VL1 | AAG CCG GTC GAC AGG NNS NNS GAT NNS TAC NNS AAC TGG TAT CAA CAG | (SEQ ID NO:44) |

II. Phage Binding Selections

For affinity-selections of phage particles displaying F(ab) variants, phage were prepared by sodium chloride/polyethylene glycol (NaCl/PEG) precipitation from *E. coli* culture supernatants. The phage were suspended in PBS buffer, then diluted into horse serum (catalog no. A-3311-D, Hyclone, Logan, Utah) containing 0.05% Tween™-20, as well as a non-displaying phage as a negative control. As a positive control, "wild-type" e426 F(ab)-phage were mixed with non-displaying phage and subjected to mock-selections.

Maxisorp 96-well plastic plates (Nunc) were coated with 2 μg/ml IgE (human IgE; Cenentech lot #9957-36) in 50 mM sodium carbonate buffer, pH 9.6, overnight at 4° C. The IgE solution was then removed, and the plates were incubated with a blocking solution of horse serum (without Tween™–20), for 2 hours at ambient temperature.

The blocking solution was removed, and the phage solution was incubated on the plates for 1 hour at room temperature. Thereafter, the phage solution was removed and the plates washed 10 times with PBS/Tween™-20 (0.05%) buffer. The wells were filled with PBS/Tween and allowed to incubate for another 10 minutes, after which the plates were again washed 10 times.

F(ab)-phage remaining bound to the plate were eluted with 20 mM HCl, neutralized with Tris-HCl, pH 8, and propagated with helper phage as described above. An aliquot of phage was serially diluted, mixed with fresh XL-1 Blue cells, plated onto appropriate antibiotic plates, and the number of CFUs (colony-forming units) of F(ab)-displaying (carbenicilin-resistant; CFUa) or non-displaying (chloramphenicol-resistant; CFUc) eluted phage were counted. The enrichment (Emut) of F(ab)-displaying over non-displaying phage at each round was calculated as (CFUa/CFUc) for the eluted pool divided by (CFUa/CFUc) for the starting pool. The enrichment for the wild-type control phage (Ewt) was calculated in the same way.

Subsequent rounds of affinity selections were carried out as described above, except that the incubation period following the first 10 washes was increased in each round. In order to compare the efficiency of phage selection from round to round under increasing stringency conditions, the enrichment factor at each round was normalized to that of the wild-type control. The ratio of binding enrichment for each pool to that of the wild-type (Emut/Ewt) is shown in FIG. 6. Since at equilibrium a greater fraction of a high-affinity variant should be bound to the IgE plate than of a lower affinity variant, higher-affinity variants should be recovered more efficiently, and therefore display greater relative enrichments. Indeed, the VL1 libraries showed successively improved relative enrichments, up to about 10-fold greater relative enrichments than wild-type after 5–6 rounds of selection. By this measure, VL1 libraries showed greater improvement in affinity over wild-type than did the VH3 libraries. The disparity in results between the two sets of CDR libraries could reflect a greater energetic contribution to antigen binding by VL1. Alternatively, the VH3 CDR of e25 may be already more nearly optimized for IgE binding than the VL1 CDR, thus permitting a greater relative improvement in the binding interactions contributed by VL1 through sidechain substitutions.

DNA sequencing showed that most F(ab)-phage variants from the first VL CDR1 library (randomizing positions 27, 28, 39 and 31) had conserved the wild-type residue D30, and preferentially mutated Y31G (table 15, wherein clones from round 3 are designated by 212–3.x, and those from round 6 are designated 212-6.x). Although a variety of substitutions were observed at positions Q27 and S28, one clone, containing Q27K and S28P, dominated the phage pool after 6 rounds of selection. This clone also contained the preferred residues D30 and G31, suggesting that this combination of sidechains might be optimal for IgE-binding.

In the second VL CDR1 library (randomizing positions 30, 31, 32 and 34), most selectants conserved wild-type residues at D30 and E32; only the wild-type D34 was observed among the sequenced clones. In this library, a variety of residue types was observed at Y31. An additional, spurious mutation, G33S, was observed in two clones, 213-6.7 and 213-6.8 (Table 15).

Sequencing analysis of clones from the VH CDR3 library after 3 rounds of selection showed that the library had essentially converged to a single clone, i.e., 214-3.1, having wild-type residues at positions 101–103, with substitutions H105T and H107Y (Table 15).

IV. Phage-ELISA Assays of Selected F(ab) Clones

To evaluate the results of the phage-binding selections, phage were transfected into *E. coli* XL-1 Blue cells and propagated in liquid culture, or plated onto antibiotic containing plates. Clones were randomly picked from these plates for sequencing and binding analysis by competitive-phage-ELISA. (Cunningham et al., *EMBO J.* 13: 2508 (1994); Lowman, Chapter 24, in *Methods in Molecular Biology*, vol. 87, S. Cabilly (ed.), Humana Press Inc., Totawa, N.J. (1997).

To evaluate the relative IgE binding affinities, phage were titrated on a plate coated with IgE as described above to normalize the displayed F(ab) concentrations. Phage were pre-mixed with serial dilutions of IgE, then added to an IgE-coated plate, and incubated for 1 hour at room temperature. The plates were then washed ten times with PBS/Tween, and a solution of rabbit anti-phage antibody mixed with a goat-anti-rabbit conjugate of horseradish peroxidase was added. After 1 hour incubation at room temperature, the plates were developed with a chromogenic substrate, o-phenylenediamine (Sigma). The reaction was stopped with addition of ½ volume of 2.5 M $H_2SO_4$. Optical density at 490 nm was measured on a spectrophotometric plate reader. The IC50 of each variant was determined by fitting a 4-parameter curve to each data set (Lowman, *Methods in Mol. Biol.*, supra). The relative binding affinity of each cloned phage variant was determined as the ratio of its IC50 to that of the starting phage, e426 (Tables 15–16).

In some cases, phage pools from a given round of selection were tested en masse in order to obtain an estimate of the population averaged relative affinity [IC50(wt)/IC50 (mutant)] for IgE. For example, the VL CDR1 library, residues 32, 33, 35 & 37 showed only 3.6-fold improved affinity versus e426 after 5 rounds of selection, eventhough the parental variant of this library (e26) appeared to have 25-fold improved affinity. Therefore, the VL-CDR1 library of these particular residues was not pursued further. On the other hand, the VH CDR2 phage pool showed 6.2 fold improved affinity over its parental e426 phage.

Phage libraries were also created of CDR domains VL CDR2, residues 54–57 and VL CDR3, residues 96–98, 99 & 100. However, amino acid substitutions at these positions failed to generate any enrichment over e426. A phage library generated for VH CDR1, residues 26–30 also failed to generate any enrichment over e26, and was found to be dominated by contaminating e26-phage. This suggests that no variants of higher affinity than e26 were present in the initial libraries.

Phage-libraries of CDR domains VL CDR1, residues 27, 28, 30, 31, 32, 34 as well as VH CDR1, residues 101, 102, 103, 105 & 107 are reported in Table 15, while VH CDR2 is reported in Table 16. In Tables 15 and 16, clone libraries which did not indicate affinity appreciable greater that of e26 were not pursued further and the binding improvement factor was not determined.

TABLE 15

F(ab)-Phage Clones from IgE Binding Selections

| phage | VL CDR1 residue | | | | | | VH CDR3 residue | | | | | fold improved binding (phage |
|---|---|---|---|---|---|---|---|---|---|---|---|---|
| clone | 27 | 28 | 30 | 31 | 32 | 34 | 101 | 102 | 103 | 105 | 107 | ELISA) |
| e426 | Q | S | D | Y | E | D | H | Y | F | H | H | -1- |
| 212-3.1 (x2) | M | R | Y | G | — | — | — | — | — | — | — | not determined |
| 212-3.2 | A | Y | N | G | — | — | — | — | — | — | — | 3.5 |
| 212-3.3 | G | G | Y | G | — | — | — | — | — | — | — | 6.9 |
| 212-3.5 | M | G | E | A | — | — | — | — | — | — | — | not determined |
| 212-6.1 | E | Q | D | W | — | — | — | — | — | — | — | 23 |
| 212-6.2 | E | R | E | S | — | — | — | — | — | — | — | not determined |
| 212-6.4 | E | H | D | W | — | — | — | — | — | — | — | 23 |
| 212-6.5 | S | N | S | G | — | — | — | — | — | — | — | not determined |
| 212-6.6 | K | E | D | S | — | — | — | — | — | — | — | not determined |
| 212-6.7 (x8) | K | P | D | G | — | — | — | — | — | — | — | 25 |

TABLE 15-continued

F(ab)-Phage Clones from IgE Binding Selections

| phage | VL CDR1 residue | | | | | | VH CDR3 residue | | | | | fold improved binding (phage |
|---|---|---|---|---|---|---|---|---|---|---|---|---|
| clone | 27 | 28 | 30 | 31 | 32 | 34 | 101 | 102 | 103 | 105 | 107 | ELISA) |
| (e26) 212-6.15 | R | P | D | T | — | — | — | — | — | — | — | not determined |
| 212-6.16 | R | S | D | G | — | — | — | — | — | — | — | not determined |
| 212-6.17 | V | T | H | S | — | — | — | — | — | — | — | not determined |
| 213-3.1 | — | — | D | D | C | D | — | — | — | — | — | not determined |
| 213-3.2 | — | — | H | D | S | D | — | — | — | — | — | not determined |
| 213-3.3 | — | — | D | W | Q | D | — | — | — | — | — | 8.8 |
| 213-3.4 | — | — | G | D | H | D | — | — | — | — | — | 3.7 |
| 213-6.1 | — | — | E | R | W | D | — | — | — | — | — | not determined |
| 213-6.3 (x2) | — | — | D | T | E | D | — | — | — | — | — | 14 |
| 213-6.4 | — | — | D | W | E | D | — | — | — | — | — | 20 |
| 213-6.7 G33S | — | — | H | N | E | D | — | — | — | — | — | not determined |
| 213-6.8 G33S | — | — | Y | S | N | D | — | — | — | — | — | 14 |
| 213-6.9 | — | — | W | G | E | D | — | — | — | — | — | not determined |
| 213-6.11 | — | — | Y | S | E | D | — | — | — | — | — | not determined |
| 213-6-12 | — | — | E | R | D | D | — | — | — | — | — | not determined |
| 213-6.13 | — | — | H | E | E | D | — | — | — | — | — | not determined |
| 213-6.14 | — | — | D | K | K | D | — | — | — | — | — | not determined |
| 213-6.15 | — | — | D | R | Q | D | — | — | — | — | — | 15 |
| 214-3.1 (x5) | — | — | — | — | — | — | H | Y | F | T | Y | 2.7 |
| 214-3.6 | — | — | — | — | — | — | H | Y | F | S | R | not determined |

TABLE 16

VH CDR2 Phage Clones

| phage | VH CDR2 residue | | | | | fold improved |
|---|---|---|---|---|---|---|
| clone | 53 | 54 | 55 | 57 | 59 | binding |
| e426 | T | Y | D | S | N | -1- |
| 235-5.1 | K | Y | S | E | K | not determined* |
| 235-5.2 | K | W | H | E | M | not determined* |
| 235-5.3 | K | W | W | E | A | not determined* |
| 235-5.4 | H | Y | A | R | K | not determined* |
| 235-5.5 | K | Y | H | G | A | not determined* |

*NOTE:
Population-averaged relative phage affinity was estimated as 6.2-fold improved over e426

V. Combined Mutations from Phase Screening

Mutations at different sites within protein often display additive effect upon protein function (Wells, *Biochemistry* 29: 8509 (1990). Therefore, several mutations from the initial phage libraries described above were combined to improve the binding to IgE.

In order to reduce the probability of increasing immunogenicity of the anti-IgE antibody, the extent of mutations from E-25 needed to be minimized. As a result, only the mutations from the phage variants which displayed the greatest improvement in affinity when measured independently were used. In addition, the frequency with which a given phage clone was observed may be related to expression level and/or proteolytic stability (Lowman & Wells, 1991, supra). One particular clone from the VL1 library, 212-6.7-renamed e26, was chosen because it exhibited an affinity 25-fold improved over e426 in phage-ELISA assays (Table 17).

The VH CDR2 library also showed affinity improvements over e426, although such improvement was only measured to be 6.2 fold as measured for the pooled phage. The pooled phage affinity demonstrated improved binding affinity for at least some members of the pool without having to measure the affinity of all the individual members. Use of the pooled phage also permits the identification of how much affinity enhancement has been obtained after a given round, and whether or not affinity selections should be continued (i.e. once a pool affinity has reached a maximum, subsequent rounds unlikely to confer additional enrichment). As such, use of pooled affinity data is a highly useful screening tool.

It was apparent that mutations in the VH CDR2 region could function additively with those in VL CDR1 because the VH CDR2 loop lies distant from the VL CDR1 loop in both crystal structure and molecular models. However, because some combinations of these mutations might nevertheless be incompatible, we tested four different combination mutants: e26 combined with the mutations found in clones 235-5.1, 235-5.2, 235-5.3, and 235-5.4 (Table 17). These constructs were made by Kunkel mutagenesis (Kunkel et al., *Methods Enzymol*. 204: 125 (1991)) using the e26 F(ab)-phage as a template, with mutagenic oligos encoding the VH2 mutations.

Phage-ELISA assays (Lowman, *Methods in Molecular Biology*, vol 87, Cabilly (ed.), Humana Press Inc., Totawa, N.J. (1997)) were used to compare the final variants from combinations of the VL CDR1 mutations in e26 with the VH CDR2 mutations in clones 235-5.1, 235-5.2, 235-5.3 and 235-5.4. Soluble F(ab) proteins were also prepared and compared in a biotin-IgE plate assay, reported below in Table 17 and in FIG. 7.

TABLE 17

| F(ab) fragment | IC50 (nm) | relative affinity (fold improved) |
|---|---|---|
| e426 | 1.5 | -1- |
| e26 | 0.17 | 8.9 |
| e27 (e26 + 235-5.1) | 0.040 | 38 |
| e695 (e26 + 235-5.2) | 0.050 | 31 |
| e696 (e26 + 235-5.3) | 0.063 | 24 |
| e697 (e26 + 235-5.4) | 0.066 | 23 |

VI. Biotin Plate Assay (FcERI-IgG Chimera Competition Assay)

Introduction: The purpose of this example is to compare how different anti-IgE F(ab)s compete with an immobilized high affinity IgE receptor IgG chimera for binding to biotinylated human IgE in solution phase when anti-IgE F(ab) and biotin-IgE are added simultaneously to a plate coated with the IgE receptor chimera. As the anti-IgE F(ab) concentration increases, the amount of biotin IgE that can bind to the receptor on the plate decreases resulting in a lower optical density value as measured by the spectrophotometer.

Nunc maxisorp plates (catalog no. F96) were coated with 100 ng/well of FcϵRI-IgG (Haak-Frendsho et al., *J. Immunol*. 151, 352 (1993), (Genentech, lot #2148-74 (6.4 mg/ml)) by aliquoting 100 μl of a 1 μg/ml stock solution in 50 nm sodium carbonate buffer (pH 9.6) for 12 to 24 hours at 4° C. Plates were washed 3 times with ELISA wash buffer (0.05% polysorbate 20 (Sigma) in PBS (pH 7.4)) and blocked by incubating with 200 μl ELISA assay buffer (Tris buffered saline, pH 4.45 with 0.5% RIA grade bovine serum albumin, Sigma; 0.05% polysorbate 20 and 4 mM EDTA) for 60 minutes. Following 3 washes with wash buffer, 100 μl of serial 2 fold dilutions of anti-IgE F(ab)s in assay buffer at an initial concentration of 200 nM were added to the ELISA plate in triplicate. Dilutions were performed with a Titertek® multichannel pipet. Biotinylated IgE in assay buffer (100 μl, 1/500 dilution of 0.5 mg/ml stock) was added to all wells and the mixture was incubated on a miniorbital shaker (Bellco) for 60 minutes at 25° C. IgE was affinity purified from U266B 1 myeloma (ATCC TIB 196) culture supernatant and biotinylated using biocytin hydrazide (O'Shannessy et al., *Immunol Lett*. 8: 273 (1984); Pierce Chemical). The samples were washed 5× with wash buffer, and the bound IgE was detected with 100 μl peroxidase-conjugated streptavidin (Zymed) at 1:3000 for 90 minutes. The samples were then washed again 6× with wash buffer followed by addition of 100 μl of substrate solution (400 μg/ml o-phenylenediamine dihydrochloride and 4 mM $H_2O_2$ in PBS), and incubated for 6 minutes. The reaction was then stopped with 4.5 M $H_2SO_4$ (100 μl) and the absorbance read at 490 nm on a Uvmax microplate reader (Molecular Devices). The absorbance at various F(ab) concentration levels of e25, e26 and e27 F(ab) antibody fragments are plotted in FIG. 8.

Conclusion: The plots in FIG. 8 indicate that both E26 and E27 have greater affinity than E25 for IgE and that E27 showed the greatest affinity.

VII. BIAcore Assays of Soluble F(ab) Proteins

The receptor-binding affinities of several F(ab) fragments were calculated (Lofas & Johnson, *J. Chem. Soc. Commun*. 21, 1526–1528 (1990)) from association and dissociation rate constants measured using a BIAcoreTM-2000 surface plasmon resonance system (BIAcore, Inc.). A biosensor chip was activated for covalent coupling of IgE using N-ethyl-N'-(3-dimethylaminopropyl)-carbodiimide hydrochloride (EDC) and N-hydroxysuccinimide (NHS) according to the manufacturer's (BIAcore) instructions. IgE was diluted into 10 nM sodium acetate buffer (pH 4.5) which was further diluted to approximately 30 μg/ml and injected over the chip to obtain a signal of 800 to 12,400 response units (RU) of immobilized material. Since the signal in RU is proportional to the mass of immobilized material, this represents a range of immobilized IgE densities on the matrix of about 0.4 to 6.5 pmol/$cm^2$. Finally, 1M ethanolamine was injected as a blocking agent. Regenerations were carried out with 4.5 M $MgCl_2$.

For kinetics measurements, 1.5 serial dilutions of F(ab) antibody fragments were injected over the IgE chip in PBS/Tween buffer (0.05% Tween-20 in phosphate buffered saline) at 25° C. using a flow rate of 20 μl/min. [FIG. 9].

Dissociation data were fit to a one-site model to obtain koff +/−s.d. (standard deviation of measurements). Pseudo-first order rate constant (ks) were calculated for each association curve, and plotted as a function of protein concentration to obtain kon +/−s.e. (standard error of fit). Equilibrium dissociation constants for Fab:IgE binding, Kd's, were calculated from SPR measurements as koff/kon. In the absence of experimental artefacts, such as re-binding of dissociated F(ab), the observed off-rate is independent of F(ab) concentration. Also, since the equilibrium dissociation constant, Kd, is inversely proportional to koff, an estimate of affinity improvement can be made assuming the association rate (kon) is a constant for all variants. The off-rates, along with calculated half-life of dissociation, are displayed in Table 18.

TABLE 18

Dissociation Kinetics

| F(ab) | $K_{off} \times 10^{-4}$ (sec$^{-1}$) | $t_{1/2}$ (min) | improved (fold) |
|---|---|---|---|
| e25 | 22 ± 4 | 5.3 | -1- |
| e26 | 3.6 ± 0.2 | 41 | 7.7 |
| e27 (e26 + 235-5.1) | 0.98 | 118 | 22 |
| e695 (e26 + 235-5.2) | 0.94 | 122 | 23 |
| e696 (e26 + 235-5.3) | 1.4 | 83 | 16 |
| e697 (e26 + 235-5.4) | 1.5 | 77 | 15 |

VIII. F(ab) Expression and Purification:

Anti-IgE F(ab) E-25 (Presta et al. *J. Immunol*. 151: 2623–2632 (1993)) and variants in phagemids derived from p426 (FIG. 10) were expressed in *E. coli* strain 34B8. Toothpick cultures (10 ml) in 2YT media with 50 μg/ml carbenicillin were incubated 8 hours at 37° C. and then transferred to 1 liter of modified AP-5 containing 50 μg/ml carbenicillin and incubated for 24 hours at 37° C. Cultures were centrifuged in 500 ml bottles at 7,000 rpm for 15 minutes at 4° C. The pellet was frozen for at least 3 hours at −20° C. Each 500 ml pellet was suspended in 12.5 ml cold 25% sucrose in 50 mM Tris pH 8.0 containing 1 mM benzamidine (Sigma) at 4° C. Suspension was solubilized by stirring at 4° C. for 3 hours. Suspension was centrifuged at 18,000 rpm for 15 minutes at 4° C. and the F(ab)s expressed in the supernatant were purified by protein G (Pharmacia) affinity chromotography. The column was washed with a solution of 10 mM Tris (pH 7.6) and 1 mM EDTA (pH 8.0) and the F(ab)s were eluted with 2.5× column volumes of 100 mM acetic acid (pH 3.0) and immediately returned to neutral pH with 0.5 volumes of 1M Tris pH 8.0. Eluates were concentrated and buffer exchanged against PBS with centricon 30 microcentrators (Amicon). Protein concentration was determined by absorbance at 280 nM with a spectrophotometer (Beckman DU 64) and sample purity was evaluated using 4–20% SDS PAGE gels (Novex) under reducing conditions with 5% β-mercaptoethanol.

IX. Results and Conclusion:

The results of phage-ELISA competition experiments show that while e26 F(ab)-phage was about 9-fold improved in affinity over e426, the combination variants e695, e696 and e697 were 20–40 fold improved over e426-phage. Additional combinations of phage-derived mutations could yield antibody variants with similarly improved affinities.

When F(ab) soluble proteins were tested in a biotin-IgE plate assay, e26 F(ab) and e27 F(ab) were about 10-fold and 30-fold improved, respectively, over e25, for inhibiting IgE binding to FcεR1-IgG. The off-rate determination by BIAcore analysis support these relative affinities. In particular, e26 and e27 showed 7.7 fold and 22-fold slower off-rates than e25. Longer half-lives imply that the IgE is "occupied" or rendered incapable of binding to the high affinity receptor for a longer period, thus resulting in improved potency of the anti-IgE therapeutic.

Thus, both equilibrium and kinetic binding data support the conclusion that e26 and e27 F(ab)s bind IgE about 10-fold and 30-fold more tightly, respectively, than e25. The full-length antibodies (IgGs) containing the corresponding F(ab) mutations are expected to display similar relative affinities to e25 IgG.

The invention claimed is:

1. A method of inhibiting the binding of IgE to the high affinity receptor FcϵRI to treat an IgE-mediated disorder comprising administering a therapeutically effective amount of an humanized anti-IgE antibody or IgE binding fragment thereof selected from the group consisting of:

(a) a molecule comprising the variable heavy and variable light chains of E26 (SEQ ID NOS:12 and 8);

(b) a molecule comprising the variable heavy and variable light chains of E27 (SEQ ID NOS:11 and 8) or (c) antigen binding fragments of (a) or (b).

2. The method of claim 1, wherein the IgE mediated disorder is hypersensitivity.

3. The method of claim 2, wherein the IgE mediated disorder is anaphylactic hypersensitivity.

4. The method of claim 3, wherein the anaphylaxis is caused by bee sting.

5. The method of claim 3, wherein the anaphylaxis is caused by snake bite.

6. The method of claim 3, wherein the anaphylaxis is caused by the administration of parental medication.

7. The method of claim 3, wherein the anaphylactic hypersensitivity results from exposure to an allergen selected from the group consisting of: pollen, food, dust mites, animal dander, fungal spores and insect venom.

8. The method of claim 1, wherein the IgE-mediated disorder is selected from the group consisting of asthma, allergic rhinitis, eczema, urticaria and food allergy.

9. The method of claim 7, wherein the allergen is pollen.

10. The method of claim 7, wherein the allergen is food.

11. The method of claim 7, wherein the allergen is dust mites.

12. The method of claim 7, wherein the allergen is animal dander.

13. The method of claim 7, wherein the allergen is fungal spores.

14. The method of claim 7, wherein the allergen is insect venom.

15. The method of claim 8, wherein the IgE-mediated disorder is asthma.

16. The method of claim 8, wherein the IgE-mediate disorder is allergic rhinitis.

17. The method of claim 8, wherein the IgE-mediated disorder is urticaria.

18. The method of claim 8, wherein the IgE-mediated disorder is food allergy.

* * * * *